US011052075B2

(12) United States Patent
Verwijs et al.

(10) Patent No.: US 11,052,075 B2
(45) Date of Patent: *Jul. 6, 2021

(54) PHARMACEUTICAL COMPOSITIONS OF 3-(6-(1-(2,2-DIFLUOROBENZO[D][1,3] DIOXOL-5-YL) CYCLOPROPANECARBOXAMIDO)-3-METHYLPYRIDIN-2-YL) BENZOIC ACID AND ADMINISTRATION THEREOF

(71) Applicant: Vertex Pharmaceuticals Incorporated, Boston, MA (US)

(72) Inventors: Marinus Jacobus Verwijs, Framingham, MA (US); Rossitza Gueorguieva Alargova, Brighton, MA (US); Ritu Rohit Kaushik, Long Island City, NY (US); Irina Nikolaevna Kadiyala, Newton, MA (US); Christopher Young, Waltham, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/530,240

(22) Filed: Aug. 2, 2019

(65) Prior Publication Data
US 2020/0197380 A1 Jun. 25, 2020

Related U.S. Application Data

(63) Continuation of application No. 16/050,029, filed on Jul. 31, 2018, now abandoned, which is a continuation of application No. 15/001,036, filed on Jan. 19, 2016, now Pat. No. 10,076,513, which is a continuation of application No. 14/542,396, filed on Nov. 14, 2014, now Pat. No. 9,241,934, which is a continuation of application No. 14/031,360, filed on Sep. 19, 2013, now abandoned, which is a continuation of application No. 13/081,750, filed on Apr. 7, 2011, now Pat. No. 8,552,034.

(60) Provisional application No. 61/366,562, filed on Jul. 22, 2010, provisional application No. 61/321,748, filed on Apr. 7, 2010, provisional application No. 61/321,729, filed on Apr. 7, 2010.

(51) Int. Cl.
| A61K 31/443 | (2006.01) |
| A61K 9/20 | (2006.01) |
| A61K 31/47 | (2006.01) |
| C07D 451/02 | (2006.01) |
| A61K 9/16 | (2006.01) |
| C07D 405/12 | (2006.01) |
| C07D 405/14 | (2006.01) |
| A61K 9/28 | (2006.01) |
| A61K 9/14 | (2006.01) |
| A61K 45/06 | (2006.01) |
| A61K 9/00 | (2006.01) |

(52) U.S. Cl.
CPC .......... *A61K 31/443* (2013.01); *A61K 9/0053* (2013.01); *A61K 9/141* (2013.01); *A61K 9/1623* (2013.01); *A61K 9/1652* (2013.01); *A61K 9/1682* (2013.01); *A61K 9/2009* (2013.01); *A61K 9/2013* (2013.01); *A61K 9/2027* (2013.01); *A61K 9/2054* (2013.01); *A61K 9/2077* (2013.01); *A61K 9/2095* (2013.01); *A61K 9/28* (2013.01); *A61K 9/2866* (2013.01); *A61K 31/47* (2013.01); *A61K 45/06* (2013.01); *C07D 405/12* (2013.01); *C07D 405/14* (2013.01); *C07D 451/02* (2013.01)

(58) Field of Classification Search
None
See application file for complete search history.

(56) References Cited

U.S. PATENT DOCUMENTS

| 3,758,475 A | 9/1973 | Hardtmann et al. |
| 4,501,729 A | 2/1985 | Boucher et al. |
| 5,739,345 A | 4/1998 | Fujita et al. |
| 5,876,700 A | 3/1999 | Boucher, Jr. et al. |
| 5,948,814 A | 9/1999 | Hwang et al. |
| 5,981,714 A | 11/1999 | Cheng et al. |
| 6,046,211 A | 4/2000 | Hansen, Jr. et al. |

(Continued)

FOREIGN PATENT DOCUMENTS

| AU | 2006311650 B2 | 2/2012 |
| CA | 2539250 A1 | 4/2005 |

(Continued)

OTHER PUBLICATIONS

Abadi, A. et al. (1999) Synthesis of 4-alkyl (aryl)-6-aryl-3-cyano-2(1H)-pyridinones and their 2-imino isosteres as nonsteroidal cardiotonic agents *Il Farmaco*, 54:195-201.

(Continued)

Primary Examiner — Robert A Wax
Assistant Examiner — Randeep Singh
(74) *Attorney, Agent, or Firm* — Finnegan, Henderson, Farabow, Garrett & Dunner LLP

(57) ABSTRACT

A pharmaceutical composition comprising Compound 1, (3-(6-(1-(2,2-difluorobenzo [d][1,3]dioxol-5-yl) cyclopropanecarboxamido)-3-methylpyridin-2-yl)benzoic acid), and at least one excipient selected from: a filler, a diluent, a disintegrant, a surfactant, a binder, a glidant and a lubricant, the composition being suitable for oral administration to a patient in need thereof to treat a CFTR mediated disease such as Cystic Fibrosis. Methods for treating a patient in need thereof include administering an oral pharmaceutical formulation of Compound 1 to the patient.

22 Claims, 27 Drawing Sheets

(56) References Cited

U.S. PATENT DOCUMENTS

| | | |
|---|---|---|
| 6,063,260 A | 5/2000 | Olesen et al. |
| 6,426,331 B1 | 7/2002 | McKinney et al. |
| 6,479,483 B2 | 11/2002 | Bös et al. |
| 6,499,984 B1 | 12/2002 | Ghebre-Sellassie et al. |
| 6,627,646 B2 | 9/2003 | Bakale et al. |
| 6,770,637 B2 | 8/2004 | Godel et al. |
| 7,005,436 B2 | 2/2006 | Lloyd et al. |
| 7,223,778 B2 | 5/2007 | Ping et al. |
| 7,297,700 B2 | 11/2007 | Kelly et al. |
| 7,407,976 B2 | 8/2008 | Miller et al. |
| 7,446,117 B2 | 11/2008 | Beswick et al. |
| 7,476,744 B2 | 1/2009 | Ferro et al. |
| 7,482,469 B2 | 1/2009 | Palin et al. |
| 7,495,103 B2 | 2/2009 | Hadida-Ruah et al. |
| 7,553,855 B2 | 6/2009 | Young et al. |
| 7,585,885 B2 | 9/2009 | Shepherd et al. |
| 7,598,412 B2 | 10/2009 | Hadida-Ruah et al. |
| 7,645,789 B2 | 1/2010 | Hadida-Ruah et al. |
| 7,659,268 B2 | 2/2010 | Hadida-Ruah et al. |
| 7,671,221 B2 | 3/2010 | Hadida-Ruah et al. |
| 7,691,902 B2 | 4/2010 | Hadida-Ruah et al. |
| 7,741,321 B2 | 6/2010 | Hadida-Ruah et al. |
| 7,754,739 B2 | 7/2010 | Hadida-Ruah et al. |
| 7,776,905 B2 | 8/2010 | Hadida-Ruah et al. |
| 7,846,951 B2 | 12/2010 | Miller et al. |
| 7,893,094 B2 | 2/2011 | Pollard et al. |
| 7,956,052 B2 | 6/2011 | Hadida-Ruah et al. |
| 7,973,038 B2 | 7/2011 | Hadida-Ruah et al. |
| 7,973,169 B2 | 7/2011 | Hadida-Ruah et al. |
| 7,977,322 B2 | 7/2011 | Ruah et al. |
| 7,999,113 B2 | 8/2011 | Hadida-Ruah et al. |
| 8,012,999 B2 | 9/2011 | Hadida-Ruah et al. |
| 8,039,491 B2 | 10/2011 | Hadida-Ruah et al. |
| 8,076,357 B2 | 12/2011 | Young et al. |
| 8,101,767 B2 | 1/2012 | Ruah et al. |
| 8,124,781 B2 | 2/2012 | Siesel |
| 8,163,772 B2 | 4/2012 | DeMattei et al. |
| 8,188,283 B2 | 5/2012 | Binch et al. |
| 8,227,615 B2 | 7/2012 | Hadida-Ruah et al. |
| 8,232,302 B2 | 7/2012 | Miller et al. |
| 8,242,149 B2 | 8/2012 | Ruah et al. |
| 8,299,099 B2 | 10/2012 | Ruah et al. |
| 8,314,239 B2 | 11/2012 | Binch et al. |
| 8,314,256 B2 | 11/2012 | Ruah et al. |
| 8,318,733 B2 | 11/2012 | Hadida-Ruah et al. |
| 8,324,207 B2 | 12/2012 | Hadida-Ruah et al. |
| 8,324,242 B2 | 12/2012 | Ruah et al. |
| 8,344,147 B2 | 1/2013 | Ambhaikar et al. |
| 8,354,427 B2 | 1/2013 | Van Goor |
| 8,362,253 B2 | 1/2013 | DeMattei et al. |
| 8,367,660 B2 | 2/2013 | Binch et al. |
| 8,389,727 B2 | 3/2013 | Zhang et al. |
| 8,399,479 B2 | 3/2013 | Binch et al. |
| 8,404,849 B2 | 3/2013 | Sun et al. |
| 8,404,865 B2 | 3/2013 | Ambhaikar et al. |
| 8,410,132 B2 | 4/2013 | Binch et al. |
| 8,410,274 B2 | 4/2013 | Hurter et al. |
| 8,415,387 B2 | 4/2013 | Ruah et al. |
| 8,431,605 B2 | 4/2013 | Hadida-Ruah et al. |
| 8,436,014 B2 | 5/2013 | Zhang et al. |
| 8,461,156 B2 | 6/2013 | Hadida-Ruah et al. |
| 8,461,342 B2 | 6/2013 | Siesel |
| 8,461,352 B2 | 6/2013 | Ambhaikar et al. |
| 8,471,029 B2 | 6/2013 | Arekar et al. |
| 8,476,442 B2 | 7/2013 | DeMattei et al. |
| 8,507,524 B2 | 8/2013 | Ruah et al. |
| 8,507,534 B2 | 8/2013 | Keshavarz-Shokri et al. |
| 8,507,687 B2 | 8/2013 | Keshavarz-Shokri et al. |
| 8,513,282 B2 | 8/2013 | Binch et al. |
| 8,524,767 B2 | 9/2013 | Miller et al. |
| 8,524,910 B2 | 9/2013 | Hadida-Ruah et al. |
| 8,541,453 B2 | 9/2013 | Hadida-Ruah et al. |
| 8,552,006 B2 | 10/2013 | Binch et al. |
| 8,552,034 B2 | 10/2013 | Verwijs et al. |
| 8,563,573 B2 | 10/2013 | Ruah et al. |
| 8,563,593 B2 | 10/2013 | Alargova et al. |
| 8,575,209 B2 | 11/2013 | Ruah et al. |
| 8,586,615 B2 | 11/2013 | Hadida-Ruah et al. |
| 8,592,602 B2 | 11/2013 | Siesel |
| 8,598,181 B2 | 12/2013 | Hadida-Ruah et al. |
| 8,598,205 B2 | 12/2013 | Binch et al. |
| 8,604,203 B2 | 12/2013 | Binch et al. |
| 8,609,703 B2 | 12/2013 | Ruah et al. |
| 8,614,325 B2 | 12/2013 | Yang et al. |
| 8,614,327 B2 | 12/2013 | Sheth et al. |
| 8,623,894 B2 | 1/2014 | DeMattei et al. |
| 8,623,905 B2 | 1/2014 | Ruah et al. |
| 8,629,162 B2 | 1/2014 | Hadida-Ruah et al. |
| 8,633,189 B2 | 1/2014 | Binch et al. |
| 8,642,609 B2 | 2/2014 | Makings et al. |
| 8,653,103 B2 | 2/2014 | Keshavarz-Shokri et al. |
| 8,674,108 B2 | 3/2014 | Luisi et al. |
| 8,710,075 B2 | 4/2014 | Binch et al. |
| 8,716,338 B2 | 5/2014 | Young |
| 8,722,704 B2 | 5/2014 | Hadida-Ruah et al. |
| 8,741,922 B2 | 6/2014 | Zhang et al. |
| 8,741,925 B2 | 6/2014 | Hadida-Ruah et al. |
| 8,741,933 B2 | 6/2014 | Hadida-Ruah et al. |
| 8,741,939 B2 | 6/2014 | Hadida-Ruah et al. |
| 8,742,122 B2 | 6/2014 | Keshavarz-Shokri et al. |
| 8,748,612 B2 | 6/2014 | Binch et al. |
| 8,754,222 B2 | 6/2014 | Ambhaikar et al. |
| 8,754,224 B2 | 6/2014 | Hurter et al. |
| 8,759,335 B2 | 6/2014 | Hadida-Ruah et al. |
| 8,765,957 B2 | 7/2014 | DeMattei et al. |
| 8,785,476 B2 | 7/2014 | Arekar et al. |
| 8,785,640 B2 | 7/2014 | Binch et al. |
| 8,796,308 B2 | 8/2014 | Yang et al. |
| 8,796,312 B2 | 8/2014 | Hadida-Ruah et al. |
| 8,802,700 B2 | 8/2014 | Sheth et al. |
| 8,802,844 B2 | 8/2014 | Gallardo-Godoy et al. |
| 8,802,868 B2 | 8/2014 | Keshavarz-Shokri et al. |
| 8,816,093 B2 | 8/2014 | Siesel |
| 8,822,451 B2 | 9/2014 | Ruah et al. |
| 8,829,204 B2 | 9/2014 | Hadida-Ruah et al. |
| 8,835,639 B2 | 9/2014 | DeMattei et al. |
| 8,846,718 B2 | 9/2014 | Keshavarz-Shokri et al. |
| 8,846,753 B2 | 9/2014 | Hadida-Ruah et al. |
| 8,853,254 B2 | 10/2014 | Hadida-Ruah et al. |
| 8,853,415 B2 | 10/2014 | Hadida-Ruah et al. |
| 8,883,206 B2 | 11/2014 | Doukou et al. |
| 8,884,018 B2 | 11/2014 | Ambhaikar et al. |
| 8,889,875 B2 | 11/2014 | Ruah et al. |
| 8,912,199 B2 | 12/2014 | Hadida-Ruah et al. |
| 8,952,049 B2 | 2/2015 | Ruah et al. |
| 8,952,050 B2 | 2/2015 | Ruah et al. |
| 8,962,856 B2 | 2/2015 | Hadida-Ruah et al. |
| 8,969,382 B2 | 3/2015 | Binch et al. |
| 8,969,386 B2 | 3/2015 | Hadida-Ruah et al. |
| 8,969,574 B2 | 3/2015 | Keshavarz-Shokri et al. |
| 8,993,600 B2 | 3/2015 | Hadida-Ruah et al. |
| 8,999,976 B2 | 4/2015 | Binch et al. |
| 9,012,473 B2 | 4/2015 | Hadida-Ruah et al. |
| 9,012,496 B2 | 4/2015 | Alargova et al. |
| 9,012,652 B2 | 4/2015 | Siesel |
| 9,035,072 B2 | 5/2015 | Belmont et al. |
| 9,045,425 B2 | 6/2015 | Luisi et al. |
| 9,051,303 B2 | 6/2015 | Keshavarz-Shokri et al. |
| 9,051,324 B2 | 6/2015 | Binch et al. |
| 9,079,916 B2 | 7/2015 | Hadida-Ruah et al. |
| 9,090,619 B2 | 7/2015 | Hadida-Ruah et al. |
| 9,102,672 B2 | 8/2015 | Hadida-Ruah et al. |
| 9,139,530 B2 | 9/2015 | Hurter et al. |
| 9,150,552 B2 | 10/2015 | Keshavarz-Shokri et al. |
| 9,192,606 B2 | 11/2015 | Young |
| 9,216,969 B2 | 12/2015 | Ruah et al. |
| 9,241,934 B2 | 1/2016 | Verwijs et al. |
| 9,249,131 B2 | 2/2016 | Hadida-Ruah et al. |
| 9,254,291 B2 | 2/2016 | Looker et al. |
| 9,255,865 B2 | 2/2016 | Kennedy et al. |
| 9,314,455 B2 | 4/2016 | Keshavarz-Shokri et al. |
| 9,321,725 B2 | 4/2016 | Miller et al. |
| 9,351,962 B2 | 5/2016 | Hadida-Ruah et al. |
| 9,371,287 B2 | 6/2016 | DeMattei et al. |

(56) References Cited

U.S. PATENT DOCUMENTS

| | | |
|---|---|---|
| 9,399,648 B2 | 7/2016 | Gallardo-Godoy |
| 9,434,717 B2 | 9/2016 | Keshavarz-Shokri et al. |
| 9,504,683 B2 | 11/2016 | Hadida-Ruah et al. |
| 9,522,145 B2 | 12/2016 | Hadida-Ruah et al. |
| 9,550,761 B2 | 1/2017 | Hadida-Ruah et al. |
| 9,670,163 B2 | 6/2017 | Hurter et al. |
| 9,701,639 B2 | 7/2017 | Strohmeier et al. |
| 9,725,440 B2 | 8/2017 | Hadida-Ruah et al. |
| 9,732,080 B2 | 8/2017 | Hadida-Ruah et al. |
| 9,751,839 B2 | 9/2017 | DeMattei et al. |
| 9,751,890 B2 | 9/2017 | Hadida-Ruah et al. |
| 9,758,510 B2 | 9/2017 | Hadida-Ruah et al. |
| 9,776,968 B2 | 10/2017 | Siesel |
| 9,840,499 B2 | 12/2017 | Keshavarz-Shokri et al. |
| 9,931,334 B2 | 4/2018 | Hurter et al. |
| 9,974,781 B2 | 5/2018 | Hadida-Ruah et al. |
| 10,022,352 B2 | 7/2018 | Hadida Ruah et al. |
| 10,058,546 B2 | 8/2018 | Alargova et al. |
| 10,071,979 B2 | 9/2018 | Tanoury et al. |
| 10,076,513 B2 | 9/2018 | Verwijs et al. |
| 10,081,621 B2 | 9/2018 | Keshavarz-Shokri et al. |
| 10,206,877 B2 | 2/2019 | Phenix et al. |
| 10,231,932 B2 | 3/2019 | Swinney et al. |
| 10,239,867 B2 | 3/2019 | Hadida Ruah et al. |
| 10,272,046 B2 | 4/2019 | Dokou et al. |
| 10,302,602 B2 | 5/2019 | Borsje et al. |
| 10,537,565 B2 | 1/2020 | Hurter et al. |
| 10,597,384 B2 | 3/2020 | Keshavarz-Shokri et al. |
| 10,626,111 B2 | 4/2020 | Hadida Ruah et al. |
| 10,646,481 B2 | 5/2020 | Rowe et al. |
| 10,662,192 B2 | 5/2020 | Hadida-Ruah et al. |
| 2002/0115619 A1 | 8/2002 | Rubenstein et al. |
| 2003/0125315 A1 | 7/2003 | Mjalli et al. |
| 2004/0110832 A1 | 6/2004 | Mjalli et al. |
| 2004/0220191 A1 | 11/2004 | Schwink et al. |
| 2005/0013861 A1 | 1/2005 | Sherwood et al. |
| 2005/0059687 A1 | 3/2005 | Makings et al. |
| 2005/0070718 A1 | 3/2005 | Lubisch et al. |
| 2005/0113379 A1 | 5/2005 | Ge et al. |
| 2005/0113423 A1 | 5/2005 | Van Goor et al. |
| 2005/0130970 A1 | 6/2005 | Miller et al. |
| 2005/0148648 A1 | 7/2005 | Hadida-Ruah et al. |
| 2005/0176789 A1 | 8/2005 | Hadida-Ruah et al. |
| 2006/0003005 A1 | 1/2006 | Cao et al. |
| 2006/0052358 A1 | 3/2006 | Ruah et al. |
| 2006/0069110 A1 | 3/2006 | Andersen et al. |
| 2006/0074075 A1 | 4/2006 | Hadida-Ruah et al. |
| 2006/0173050 A1 | 8/2006 | Liu et al. |
| 2006/0217448 A1 | 9/2006 | Kelly et al. |
| 2007/0078120 A1 | 4/2007 | Ban et al. |
| 2007/0105833 A1 | 5/2007 | Ruah et al. |
| 2007/0142411 A1 | 6/2007 | Hagan et al. |
| 2007/0238775 A1 | 10/2007 | Ruah et al. |
| 2007/0244159 A1 | 10/2007 | Hadida-Ruah et al. |
| 2007/0264196 A1 | 11/2007 | Ruah et al. |
| 2008/0009524 A1 | 1/2008 | Hadida-Ruah et al. |
| 2008/0019915 A1 | 1/2008 | Hadida-Ruah et al. |
| 2008/0044355 A1 | 2/2008 | Ruah et al. |
| 2008/0071095 A1 | 3/2008 | Hadida-Ruah et al. |
| 2008/0090864 A1 | 4/2008 | Young et al. |
| 2008/0113985 A1 | 5/2008 | Ruah et al. |
| 2008/0138803 A1 | 6/2008 | Galvan-Goldman (nee Galvan) et al. |
| 2008/0161371 A1 | 7/2008 | Hadida-Ruah et al. |
| 2008/0176899 A1 | 7/2008 | Ruah et al. |
| 2008/0260820 A1 | 10/2008 | Borrelly et al. |
| 2008/0286204 A1 | 11/2008 | Hadida-Ruah et al. |
| 2008/0306062 A1 | 12/2008 | Hadida-Ruah et al. |
| 2009/0018140 A1 | 1/2009 | Miller et al. |
| 2009/0099230 A1 | 4/2009 | DeMattei et al. |
| 2009/0105272 A1 | 4/2009 | Grootenhuis et al. |
| 2009/0131492 A1 | 5/2009 | Hadida-Ruah et al. |
| 2009/0143381 A1 | 6/2009 | Hadida-Ruah et al. |
| 2009/0170905 A1 | 7/2009 | Keshavarez-Shokri et al. |
| 2009/0176839 A1 | 7/2009 | Keshavarez-Shokri et al. |
| 2009/0176989 A1 | 7/2009 | Siesel |
| 2009/0221597 A1 | 9/2009 | Hadida-Ruah et al. |
| 2009/0227797 A1 | 9/2009 | Hadida-Ruah et al. |
| 2009/0246137 A1 | 10/2009 | Hadida-Ruah et al. |
| 2009/0246820 A1 | 10/2009 | Singh et al. |
| 2009/0253736 A1 | 10/2009 | Hadida-Ruah et al. |
| 2009/0298876 A1 | 12/2009 | Hadida-Ruah et al. |
| 2010/0036130 A1 | 2/2010 | Siesel |
| 2010/0069434 A1 | 3/2010 | Young et al. |
| 2010/0074949 A1 | 3/2010 | Rowe et al. |
| 2010/0087435 A1 | 4/2010 | Hadida-Ruah et al. |
| 2010/0087490 A1 | 4/2010 | Young |
| 2010/0105739 A1 | 4/2010 | Hadida-Ruah et al. |
| 2010/0113508 A1 | 5/2010 | Binch et al. |
| 2010/0113509 A1 | 5/2010 | Binch et al. |
| 2010/0113555 A1 | 5/2010 | Hadida-Ruah et al. |
| 2010/0125090 A1 | 5/2010 | Hadida-Ruah et al. |
| 2010/0130547 A1 | 5/2010 | Zhang et al. |
| 2010/0144798 A1 | 6/2010 | Van Goor et al. |
| 2010/0168094 A1 | 7/2010 | Binch et al. |
| 2010/0168158 A1 | 7/2010 | Binch et al. |
| 2010/0184739 A1 | 7/2010 | Sheth et al. |
| 2010/0210638 A1 | 8/2010 | Ruah et al. |
| 2010/0227888 A1 | 9/2010 | Hadida-Ruah et al. |
| 2010/0249113 A1 | 9/2010 | Hadida-Ruah et al. |
| 2010/0249180 A1 | 9/2010 | Gallardo-Godoy |
| 2010/0256184 A1 | 10/2010 | Rowe et al. |
| 2010/0261750 A1 | 10/2010 | Binch et al. |
| 2010/0267768 A1 | 10/2010 | DeMattei et al. |
| 2010/0299058 A1 | 11/2010 | Nortrup et al. |
| 2010/0331344 A1 | 12/2010 | Hadida-Ruah et al. |
| 2011/0008259 A1 | 1/2011 | Binch et al. |
| 2011/0060024 A1 | 3/2011 | Hadida-Ruah et al. |
| 2011/0064811 A1 | 3/2011 | Hurter et al. |
| 2011/0065928 A1 | 3/2011 | Bhalchandra et al. |
| 2011/0071206 A1 | 3/2011 | Hadida-Ruah et al. |
| 2011/0098311 A1 | 4/2011 | Van Goor et al. |
| 2011/0123449 A1 | 5/2011 | Zhang et al. |
| 2011/0124869 A1 | 5/2011 | Bhalchandra et al. |
| 2011/0144123 A1 | 6/2011 | Miller et al. |
| 2011/0172229 A1 | 7/2011 | Hadida-Ruah et al. |
| 2011/0177999 A1 | 7/2011 | Singh et al. |
| 2011/0230519 A1 | 9/2011 | Arekar et al. |
| 2011/0251253 A1 | 10/2011 | Keshavarz-Shokri et al. |
| 2011/0256220 A1 | 10/2011 | Verwijs et al. |
| 2011/0257223 A1 | 10/2011 | Goor et al. |
| 2011/0263654 A1 | 10/2011 | Keshavarz-Shokri et al. |
| 2011/0288121 A1 | 11/2011 | Sun et al. |
| 2011/0288122 A1 | 11/2011 | Van Goor et al. |
| 2011/0306637 A1 | 12/2011 | Hadida-Ruah et al. |
| 2011/0312958 A1 | 12/2011 | Hadida Ruah et al. |
| 2012/0004216 A1 | 1/2012 | Hadida Ruah et al. |
| 2012/0010257 A1 | 1/2012 | Hadida-Ruah et al. |
| 2012/0015999 A1 | 1/2012 | Alargova et al. |
| 2012/0035179 A1 | 2/2012 | Hadida-Ruah et al. |
| 2012/0046330 A1 | 2/2012 | Alargova et al. |
| 2012/0061869 A1 | 3/2012 | Boeckx et al. |
| 2012/0064157 A1 | 3/2012 | Dokou et al. |
| 2012/0071504 A1 | 3/2012 | Yang et al. |
| 2012/0165372 A1 | 3/2012 | DeMattei et al. |
| 2012/0122921 A1 | 5/2012 | DeMattei et al. |
| 2012/0122922 A1 | 5/2012 | Young et al. |
| 2012/0184583 A1 | 7/2012 | Van Goor et al. |
| 2012/0190856 A1 | 7/2012 | Siesel |
| 2012/0203006 A1 | 8/2012 | Siesel |
| 2012/0208841 A1 | 8/2012 | Binch et al. |
| 2012/0214841 A1 | 8/2012 | Hurter et al. |
| 2012/0220625 A1 | 8/2012 | Rowe et al. |
| 2012/0232059 A1 | 9/2012 | Hadida-Ruah et al. |
| 2012/0258983 A1 | 10/2012 | Rowe et al. |
| 2012/0259129 A1 | 10/2012 | Bhalchandra et al. |
| 2012/0270869 A1 | 10/2012 | Hadida Ruah et al. |
| 2012/0277268 A1 | 11/2012 | Keshavarz-Shokri et al. |
| 2012/0309758 A1 | 12/2012 | Sheth et al. |
| 2012/0322798 A1 | 12/2012 | Hadida Ruah et al. |
| 2013/0011923 A1 | 1/2013 | Ruah et al. |
| 2013/0012536 A1 | 1/2013 | Hadida-Ruah et al. |
| 2013/0018070 A1 | 1/2013 | Binch et al. |
| 2013/0018071 A1 | 1/2013 | Arekar et al. |

(56) References Cited

U.S. PATENT DOCUMENTS

| | | |
|---|---|---|
| 2013/0023538 A1 | 1/2013 | Hadida Ruah et al. |
| 2013/0035327 A1 | 2/2013 | Hadida-Ruah et al. |
| 2013/0040986 A1 | 2/2013 | Binch et al. |
| 2013/0072522 A1 | 3/2013 | DeMattei et al. |
| 2013/0072687 A1 | 3/2013 | Ambhaikar et al. |
| 2013/0079367 A1 | 3/2013 | Arekar et al. |
| 2013/0085158 A1 | 4/2013 | Keshavarz-Shokri et al. |
| 2013/0090354 A1 | 4/2013 | Van Goor et al. |
| 2013/0095181 A1 | 4/2013 | Verwijs et al. |
| 2013/0109717 A1 | 5/2013 | DeMattei et al. |
| 2013/0116238 A1 | 5/2013 | Looker et al. |
| 2013/0131107 A1 | 5/2013 | Van Goor et al. |
| 2013/0137722 A1 | 5/2013 | Zhang et al. |
| 2013/0143918 A1 | 6/2013 | Keshavarz-Shokri et al. |
| 2013/0143919 A1 | 6/2013 | Van Goor et al. |
| 2013/0158071 A1 | 6/2013 | Van Goor et al. |
| 2013/0165442 A1 | 6/2013 | Sheth et al. |
| 2013/0178471 A1 | 7/2013 | Hadida Ruah et al. |
| 2013/0178496 A1 | 7/2013 | Binch et al. |
| 2013/0184276 A1 | 7/2013 | Hadida-Ruah et al. |
| 2013/0186801 A1 | 7/2013 | Verwijs et al. |
| 2013/0196983 A1 | 8/2013 | Binch et al. |
| 2013/0224293 A1 | 8/2013 | Dokou et al. |
| 2013/0231364 A1 | 9/2013 | Binch et al. |
| 2013/0231368 A1 | 9/2013 | Zhang et al. |
| 2013/0237568 A1 | 9/2013 | Hadida Ruah et al. |
| 2013/0237569 A1 | 9/2013 | Hadida Ruah et al. |
| 2013/0245010 A1 | 9/2013 | Hadida-Ruah et al. |
| 2013/0245011 A1 | 9/2013 | Hadida-Ruah et al. |
| 2013/0252333 A1 | 9/2013 | Hadida Ruah et al. |
| 2013/0274477 A1 | 10/2013 | Siesel |
| 2013/0281487 A1 | 10/2013 | Luisi et al. |
| 2013/0296306 A1 | 11/2013 | Hadida Ruah et al. |
| 2013/0296364 A1 | 11/2013 | Hadida Ruah et al. |
| 2013/0296379 A1 | 11/2013 | Keshavarz-Shokri et al. |
| 2013/0303484 A1 | 11/2013 | Grootenhuis et al. |
| 2013/0303570 A1 | 11/2013 | Binch et al. |
| 2013/0317020 A1 | 11/2013 | Hadida Ruah et al. |
| 2013/0317060 A1 | 11/2013 | Hurter et al. |
| 2013/0324743 A1 | 12/2013 | Belmont et al. |
| 2013/0331567 A1 | 12/2013 | Hadida-Ruah et al. |
| 2014/0011846 A1 | 1/2014 | Keshavarz-Shokri et al. |
| 2014/0012003 A1 | 1/2014 | DeMattei et al. |
| 2014/0023706 A1 | 1/2014 | Verwijs et al. |
| 2014/0024672 A1 | 1/2014 | Hadida-Ruah et al. |
| 2014/0051724 A1 | 2/2014 | Hadida-Ruah et al. |
| 2014/0057906 A1 | 2/2014 | Hadida-Ruah et al. |
| 2014/0072995 A1 | 3/2014 | Hadida-Ruah et al. |
| 2014/0073653 A1 | 3/2014 | Binch et al. |
| 2014/0080823 A1 | 3/2014 | Varasi et al. |
| 2014/0080825 A1 | 3/2014 | Hadida-Ruah et al. |
| 2014/0080826 A1 | 3/2014 | Ruah et al. |
| 2014/0088141 A1 | 3/2014 | Binch et al. |
| 2014/0088160 A1 | 3/2014 | Rossitza Gueorguieva et al. |
| 2014/0094499 A1 | 4/2014 | Alargova et al. |
| 2014/0112988 A1 | 4/2014 | Rowe et al. |
| 2014/0121208 A1 | 5/2014 | Van Goor et al. |
| 2014/0121379 A1 | 5/2014 | Siesel |
| 2014/0121381 A1 | 5/2014 | Hadida-Ruah et al. |
| 2014/0142138 A1 | 5/2014 | Van Goor et al. |
| 2014/0142312 A1 | 5/2014 | Luisi et al. |
| 2014/0155431 A1 | 6/2014 | Hadida-Ruah et al. |
| 2014/0155626 A1 | 6/2014 | Hadida-Ruah et al. |
| 2014/0163011 A1 | 6/2014 | Hadida-Ruah et al. |
| 2014/0163068 A1 | 6/2014 | Verwijs et al. |
| 2014/0187787 A1 | 7/2014 | Ambhaikar et al. |
| 2014/0206689 A1 | 7/2014 | Hadida-Ruah et al. |
| 2014/0206720 A1 | 7/2014 | Young |
| 2014/0088142 A1 | 8/2014 | Yang et al. |
| 2014/0221424 A1 | 8/2014 | Zha |
| 2014/0221430 A1 | 8/2014 | Keshavarz-Shokri et al. |
| 2014/0235625 A1 | 8/2014 | Binch et al. |
| 2014/0235668 A1 | 8/2014 | Binch et al. |
| 2014/0242172 A1 | 8/2014 | Hurter et al. |
| 2014/0243289 A1 | 8/2014 | Grootenhuis et al. |
| 2014/0255483 A1 | 9/2014 | Dokou et al. |
| 2014/0256770 A1 | 9/2014 | DeMattei et al. |
| 2014/0303204 A1 | 10/2014 | Binch et al. |
| 2014/0303205 A1 | 10/2014 | Yang et al. |
| 2014/0315948 A1 | 10/2014 | Rowe et al. |
| 2014/0323521 A1 | 10/2014 | Van Goor et al. |
| 2014/0329855 A1 | 11/2014 | Arekar et al. |
| 2014/0330023 A1 | 11/2014 | Siesel |
| 2014/0336393 A1 | 11/2014 | Ambhaikar et al. |
| 2014/0343098 A1 | 11/2014 | Sheth et al. |
| 2014/0343315 A1 | 11/2014 | Hadida-Ruah et al. |
| 2014/0350281 A1 | 11/2014 | DeMattei et al. |
| 2014/0371230 A1 | 12/2014 | Hadida-Ruah et al. |
| 2014/0371275 A1 | 12/2014 | Keshavarz-Shokri et al. |
| 2015/0005344 A1 | 1/2015 | Keshavarz-Shokri et al. |
| 2015/0010628 A1 | 1/2015 | Dokou et al. |
| 2015/0024047 A1 | 1/2015 | Dokou et al. |
| 2015/0025076 A1 | 1/2015 | Hadida Ruah et al. |
| 2015/0031708 A1 | 1/2015 | Hadida-Ruah et al. |
| 2015/0031720 A1 | 1/2015 | Gallardo-Godoy |
| 2015/0031722 A1 | 1/2015 | Hadida-Ruah et al. |
| 2015/0065487 A1 | 3/2015 | Hadida-Ruah et al. |
| 2015/0065497 A1 | 3/2015 | Hadida-Ruah et al. |
| 2015/0065500 A1 | 3/2015 | Hadida-Ruah et al. |
| 2015/0080431 A1 | 3/2015 | Van Goor et al. |
| 2015/0094304 A1 | 4/2015 | Ruah et al. |
| 2015/0119441 A1 | 4/2015 | Hadida-Ruah et al. |
| 2015/0126566 A1 | 5/2015 | Hadida-Ruah et al. |
| 2015/0140094 A1 | 5/2015 | Verwijs et al. |
| 2015/0141459 A1 | 5/2015 | Van Goor et al. |
| 2015/0150879 A2 | 6/2015 | Van Goor et al. |
| 2015/0164881 A1 | 6/2015 | Van Goor et al. |
| 2015/0164883 A1 | 6/2015 | Van Goor et al. |
| 2015/0166516 A1 | 6/2015 | Hadida-Ruah et al. |
| 2015/0174098 A1 | 6/2015 | Ruah et al. |
| 2015/0182517 A1 | 7/2015 | Alargova et al. |
| 2015/0190390 A1 | 7/2015 | Hadida Ruah et al. |
| 2015/0196539 A1 | 7/2015 | Keshavarz-Shokri et al. |
| 2015/0203478 A1 | 7/2015 | Keshavarz-Shokri et al. |
| 2015/0218122 A1 | 8/2015 | Tanoury et al. |
| 2015/0231142 A1 | 8/2015 | Van Goor et al. |
| 2015/0246031 A1 | 9/2015 | Dokou et al. |
| 2015/0265612 A1 | 9/2015 | Hadida Ruah et al. |
| 2015/0293078 A1 | 10/2015 | Singh et al. |
| 2015/0320736 A1 | 11/2015 | Phenix et al. |
| 2015/0336898 A1 | 11/2015 | Grootenhuis et al. |
| 2015/0336956 A1 | 11/2015 | Hadida-Ruah et al. |
| 2016/0022664 A2 | 1/2016 | Van Goor et al. |
| 2016/0022665 A2 | 1/2016 | Van Goor et al. |
| 2016/0039800 A1 | 2/2016 | Young |
| 2016/0052916 A1 | 2/2016 | Keshavarz-Shokri et al. |
| 2016/0067239 A9 | 3/2016 | Van Goor et al. |
| 2016/0095858 A1 | 4/2016 | Miller et al. |
| 2016/0096807 A1 | 4/2016 | Strohmeier et al. |
| 2016/0143898 A1 | 5/2016 | Hadida-Ruah et al. |
| 2016/0166540 A1 | 6/2016 | Looker et al. |
| 2016/0200712 A1 | 7/2016 | Siesel |
| 2016/0213648 A1 | 7/2016 | Duncton et al. |
| 2016/0221952 A1 | 8/2016 | Yang et al. |
| 2016/0221995 A1 | 8/2016 | Keshavarz-Shokri et al. |
| 2016/0228414 A1 | 8/2016 | Hadida-Ruah et al. |
| 2016/0229806 A1 | 8/2016 | Hurter et al. |
| 2016/0237079 A1 | 8/2016 | Hadida-Ruah et al. |
| 2016/0271105 A1 | 9/2016 | Hadida-Ruah et al. |
| 2016/0303096 A1 | 10/2016 | Verwijs et al. |
| 2016/0318931 A1 | 11/2016 | Hadida-Ruah et al. |
| 2016/0324788 A1 | 11/2016 | Verwijs |
| 2016/0324846 A1 | 11/2016 | Verwijs et al. |
| 2016/0332997 A1 | 11/2016 | Hadida-Ruah et al. |
| 2017/0087144 A1 | 3/2017 | Rowe et al. |
| 2017/0096396 A1 | 4/2017 | DeMattei et al. |
| 2017/0100340 A1 | 4/2017 | Dokou et al. |
| 2017/0107205 A1 | 4/2017 | Hadida-Ruah et al. |
| 2017/0107206 A1 | 4/2017 | Hadida-Ruah et al. |
| 2017/0107225 A1 | 4/2017 | Hadida-Ruah et al. |
| 2017/0231970 A1 | 8/2017 | Hurter et al. |
| 2017/0266176 A1 | 9/2017 | Alargova et al. |
| 2018/0008546 A1 | 1/2018 | Verwijs et al. |
| 2018/0127398 A1 | 5/2018 | Keshavarz-Shokri et al. |

(56) References Cited

U.S. PATENT DOCUMENTS

| | | | |
|---|---|---|---|
| 2018/0153874 | A1 | 6/2018 | Van Goor et al. |
| 2018/0162842 | A1 | 6/2018 | Hadida-Ruah et al. |
| 2018/0280349 | A1 | 10/2018 | Van Goor et al. |
| 2019/0038615 | A1 | 2/2019 | Van Goor et al. |
| 2019/0070155 | A1 | 3/2019 | Verwijs et al. |
| 2019/0076419 | A1 | 3/2019 | Hadida Ruah et al. |
| 2019/0144450 | A1 | 5/2019 | Hadida Ruah et al. |
| 2019/0210991 | A1 | 7/2019 | Tanoury et al. |
| 2019/0270728 | A1 | 9/2019 | Keshavarz-Shokri et al. |
| 2019/0274959 | A1 | 9/2019 | Dokou et al. |
| 2020/0085750 | A1 | 3/2020 | Verwijs |
| 2020/0115366 | A1 | 4/2020 | Hadida Ruah et al. |

FOREIGN PATENT DOCUMENTS

| | | | |
|---|---|---|---|
| CA | 2605300 | A1 | 10/2006 |
| CA | 2736545 | A1 | 4/2010 |
| CN | 1335771 | A | 2/2002 |
| CN | 1356988 | A | 7/2002 |
| CN | 1938279 | A | 3/2007 |
| CN | 101006076 | A | 7/2007 |
| CN | 101198333 | A | 6/2008 |
| CN | 101287732 | A | 10/2008 |
| CN | 101460489 | A | 6/2009 |
| CN | 101910156 | A | 12/2010 |
| CN | 101912344 | A | 12/2010 |
| CN | 102058889 | A | 5/2011 |
| CN | 102164587 | A | 8/2011 |
| CN | 102203588 | A | 9/2011 |
| CN | 102231990 | A | 11/2011 |
| CN | 102438578 | A | 5/2012 |
| CN | 102507770 | A | 6/2012 |
| CN | 103743826 | A | 4/2014 |
| CN | 104122345 | A | 10/2014 |
| CN | 104122346 | A | 10/2014 |
| CN | 105890945 | A | 8/2016 |
| CN | 103822976 | A | 5/2019 |
| CN | 104090038 | A | 10/2019 |
| EP | 0081756 | A1 | 6/1983 |
| EP | 0574174 | A2 | 12/1993 |
| EP | 0591830 | A1 | 4/1994 |
| EP | 0635713 | B1 | 10/1997 |
| EP | 1026149 | A1 | 8/2000 |
| EP | 2231606 | B1 | 2/2013 |
| EP | 2615085 | A1 | 7/2013 |
| JP | 58-121274 | A | 7/1983 |
| JP | 5-78356 | A | 3/1993 |
| JP | 8-301870 | A | 11/1996 |
| JP | 2002-114777 | A | 4/2002 |
| JP | 2003-501420 | A | 1/2003 |
| JP | 2003-155285 | A | 5/2003 |
| JP | 2003-519698 | A | 6/2003 |
| JP | 2003-221386 | A | 8/2003 |
| JP | 2004-520394 | A | 7/2004 |
| JP | 2005-053902 | A | 3/2005 |
| JP | 2005-508904 | A | 4/2005 |
| JP | 2005-187464 | A | 7/2005 |
| JP | 2005-525389 | A | 8/2005 |
| JP | 2005-529114 | A | 9/2005 |
| JP | 2006-507247 | A | 3/2006 |
| JP | 2006-508016 | A | 3/2006 |
| JP | 2006-512338 | A | 4/2006 |
| JP | 2006-117535 | A | 5/2006 |
| JP | 2007-511572 | A | 5/2007 |
| JP | 2007-518791 | A | 7/2007 |
| JP | 2007-519740 | A | 7/2007 |
| JP | 2007-533740 | A | 11/2007 |
| JP | 2008-504097 | A | 2/2008 |
| JP | 2008-516639 | A | 5/2008 |
| JP | 2008-150364 | A | 7/2008 |
| JP | 2009-514962 | A | 4/2009 |
| JP | 2011-506330 | A | 3/2011 |
| JP | 2011-529101 | A | 12/2011 |
| JP | 2011-530598 | A | 12/2011 |
| JP | 2012-233011 | A | 11/2012 |
| JP | 5165586 | B2 | 3/2013 |
| JP | 5317184 | B2 | 10/2013 |
| JP | 2013-253790 | A | 12/2013 |
| JP | 5497633 | B2 | 5/2014 |
| JP | 2015-504920 | A | 2/2015 |
| JP | 5666525 | B2 | 2/2015 |
| JP | 5702149 | B2 | 2/2015 |
| RU | 96121599 | A | 2/1999 |
| RU | 2154064 | C2 | 8/2000 |
| WO | WO 1995/06046 | A1 | 3/1995 |
| WO | WO 1996/10027 | A1 | 4/1996 |
| WO | WO 1996/19444 | A1 | 6/1996 |
| WO | WO 1997/36876 | A1 | 10/1997 |
| WO | WO 1998/07420 | A1 | 2/1998 |
| WO | WO 1998/28980 | A1 | 7/1998 |
| WO | WO 1998/35681 | A1 | 8/1998 |
| WO | WO 1998/47868 | A1 | 10/1998 |
| WO | WO 1999/41405 | A1 | 8/1999 |
| WO | WO 1999/64394 | A1 | 12/1999 |
| WO | WO 2000/16798 | A1 | 3/2000 |
| WO | WO 2000/35452 | A1 | 6/2000 |
| WO | WO 2000/50398 | A2 | 8/2000 |
| WO | WO 2000/50401 | A1 | 8/2000 |
| WO | WO 2000/75120 | A1 | 12/2000 |
| WO | WO 2001/46165 | A2 | 6/2001 |
| WO | WO 2001/51919 | A2 | 7/2001 |
| WO | WO 2001/54690 | A1 | 8/2001 |
| WO | WO 2001/56989 | A2 | 8/2001 |
| WO | WO 2001/81317 | A1 | 11/2001 |
| WO | WO 2001/83517 | A1 | 11/2001 |
| WO | WO 2001/92235 | A1 | 12/2001 |
| WO | WO 2002/16324 | A1 | 2/2002 |
| WO | WO 2002/22601 | A1 | 3/2002 |
| WO | WO 2002/30875 | A1 | 4/2002 |
| WO | WO 2002/34739 | A1 | 5/2002 |
| WO | WO 2002/38107 | A2 | 5/2002 |
| WO | WO 2002/44183 | A2 | 6/2002 |
| WO | WO 2002/62804 | A1 | 8/2002 |
| WO | WO 2002/79134 | A1 | 10/2002 |
| WO | WO 2002/85458 | A2 | 10/2002 |
| WO | WO 2002/96421 | A1 | 12/2002 |
| WO | WO 2003/006016 | A2 | 1/2003 |
| WO | WO 2003/007888 | A2 | 1/2003 |
| WO | WO 2003/007945 | A1 | 1/2003 |
| WO | WO 2003/022852 | A2 | 3/2003 |
| WO | WO 2003/042191 | A1 | 5/2003 |
| WO | WO 2003/055482 | A1 | 7/2003 |
| WO | WO 2003/063797 | A2 | 8/2003 |
| WO | WO 2002/071033 | A3 | 9/2003 |
| WO | WO 2003/082186 | A2 | 10/2003 |
| WO | WO 2003/084997 | A1 | 10/2003 |
| WO | WO 2003/088908 | A2 | 10/2003 |
| WO | WO 2003/105788 | A2 | 12/2003 |
| WO | WO 2004/024691 | A1 | 3/2004 |
| WO | WO 2004/035571 | A1 | 4/2004 |
| WO | WO 2004/040295 | A1 | 5/2004 |
| WO | WO 2004/041163 | A2 | 5/2004 |
| WO | WO 2004/047974 | A1 | 6/2004 |
| WO | WO 2004/054505 | A2 | 7/2004 |
| WO | WO 2004/063179 | A1 | 7/2004 |
| WO | WO 2004/072038 | A1 | 8/2004 |
| WO | WO 2004/099168 | A2 | 11/2004 |
| WO | WO 2005/000300 | A1 | 1/2005 |
| WO | WO 2005/023806 | A2 | 3/2005 |
| WO | WO 2005/026137 | A2 | 3/2005 |
| WO | WO 2005/030702 | A1 | 4/2005 |
| WO | WO 2005/030755 | A1 | 4/2005 |
| WO | WO 2005/039589 | A2 | 5/2005 |
| WO | WO 2005/044797 | A1 | 5/2005 |
| WO | WO 2005/049018 | A1 | 6/2005 |
| WO | WO 2005/049034 | A2 | 6/2005 |
| WO | WO 2005/075435 | A1 | 8/2005 |
| WO | WO 2005/080348 | A1 | 9/2005 |
| WO | WO 2005/080381 | A1 | 9/2005 |
| WO | WO 2005/100353 | A1 | 10/2005 |
| WO | WO 2005/108391 | A1 | 11/2005 |
| WO | WO 2005/115399 | A2 | 12/2005 |
| WO | WO 2005/123569 | A1 | 12/2005 |
| WO | WO 2006/002421 | A2 | 1/2006 |

(56) References Cited

FOREIGN PATENT DOCUMENTS

| | | |
|---|---|---|
| WO | WO 2006/003504 A1 | 1/2006 |
| WO | WO 2006/014012 A2 | 2/2006 |
| WO | WO 2006/040520 A1 | 4/2006 |
| WO | WO 2006/051394 A1 | 5/2006 |
| WO | WO 2006/063999 A1 | 6/2006 |
| WO | WO 2006/067931 A1 | 6/2006 |
| WO | WO 2006/080884 A1 | 8/2006 |
| WO | WO 2006/082952 A1 | 8/2006 |
| WO | WO 2006/108127 A2 | 10/2006 |
| WO | WO 2006/108695 A2 | 10/2006 |
| WO | WO 2006/113704 A2 | 10/2006 |
| WO | WO 2006/113919 A2 | 10/2006 |
| WO | WO 2006/115834 A1 | 11/2006 |
| WO | WO 2006/116218 A1 | 11/2006 |
| WO | WO 2006/129199 A1 | 12/2006 |
| WO | WO 2006/130403 A1 | 12/2006 |
| WO | WO 2006/136829 A2 | 12/2006 |
| WO | WO 2007/021982 A2 | 2/2007 |
| WO | WO 2007/028654 A1 | 3/2007 |
| WO | WO 2007/039420 A1 | 4/2007 |
| WO | WO 2007/045462 A2 | 4/2007 |
| WO | WO 2007/054480 A1 | 5/2007 |
| WO | WO 2007/056341 A1 | 5/2007 |
| WO | WO 2007/067506 A | 6/2007 |
| WO | WO 2007/075946 A1 | 7/2007 |
| WO | WO 2007/079139 A2 | 7/2007 |
| WO | WO 2007/079257 A2 | 7/2007 |
| WO | WO 2007/087066 A2 | 8/2007 |
| WO | WO 2007/117715 A2 | 10/2007 |
| WO | WO 2007/134279 A2 | 11/2007 |
| WO | WO 2008/065068 A2 | 6/2008 |
| WO | WO 2008/127399 A2 | 10/2008 |
| WO | WO 2008/137787 A2 | 11/2008 |
| WO | WO 2008/141119 A2 | 11/2008 |
| WO | WO 2008/147952 A1 | 12/2008 |
| WO | WO 2009/006315 A1 | 1/2009 |
| WO | WO 2009/023509 A2 | 2/2009 |
| WO | WO 2009/033561 A1 | 3/2009 |
| WO | WO 2009/036412 A1 | 3/2009 |
| WO | WO 2009/038683 A2 | 3/2009 |
| WO | WO 2009/038913 A2 | 3/2009 |
| WO | WO 2009/073757 A1 | 6/2009 |
| WO | WO 2009/074749 A2 | 6/2009 |
| WO | WO 2009/076141 A2 | 6/2009 |
| WO | WO 2009/076142 A2 | 6/2009 |
| WO | WO 2009/076593 A1 | 6/2009 |
| WO | WO 2009/111228 A2 | 9/2009 |
| WO | WO 2009/123896 A1 | 10/2009 |
| WO | WO 2010/013035 A1 | 2/2010 |
| WO | WO 2010/019239 A2 | 2/2010 |
| WO | WO 2010/037066 A2 | 4/2010 |
| WO | WO 2010/048526 A2 | 4/2010 |
| WO | WO 2010/048564 A1 | 4/2010 |
| WO | WO 2010/053471 A1 | 5/2010 |
| WO | WO 2010/054138 A2 | 5/2010 |
| WO | WO 2010/128359 A1 | 11/2010 |
| WO | WO 2010/138484 A2 | 12/2010 |
| WO | WO 2011/127241 A2 | 10/2011 |
| WO | WO 2011/127290 A2 | 10/2011 |
| WO | WO 2011/133951 A1 | 10/2011 |
| WO | WO 2011/133953 A1 | 10/2011 |
| WO | WO 2011/133956 A1 | 10/2011 |
| WO | WO 2013/112804 A1 | 8/2013 |
| WO | WO 2013/185112 A1 | 12/2013 |
| WO | WO 2014/014841 A1 | 1/2014 |
| WO | WO 2014/055501 A1 | 4/2014 |
| WO | WO 2014/071122 A1 | 5/2014 |
| WO | WO 2015/073231 A1 | 5/2014 |
| WO | WO 2014/089216 A1 | 6/2014 |
| WO | WO 2016/081556 A1 | 5/2016 |
| WO | WO 2016/086103 A1 | 6/2016 |
| WO | WO 2016/086136 A1 | 6/2016 |
| WO | WO 2016/087665 A2 | 6/2016 |
| WO | WO 2016/185423 A1 | 11/2016 |

OTHER PUBLICATIONS

Abramzon, A.A. (1981) *Surfactant Active Agents: Properties and Applications*. 2nd ed. , p. 3 (Russian).

Amaral, M. D. and C.M. Farinha (2013) "Rescuing Mutant CFTR: A Multi-task Approach to a Better Outcome in Treating Cystic Fibrosis" *Curr Pharm Des*, 19:3497-3508.

Andrews, J. et al. (1999) *An Introduction to Environmental Chemistry*. Blackwell Science; p. 117 (Russian).

Aventis Pharmaceuticals, Inc. (May 12, 2003) Prescribing Information for Allegra® (10 pages).

Batt, D.G. and G.C. Houghton (May 1995) "Polyfunctional pyridines from nitroacetamidine and β-diketones. A useful synthesis of substituted imidazo [4,5-b] pyridines and related compounds" *J Heterocycl Chem*, 32(3):963-969.

Bauer, K.H. et al. (1999) *Lehrbuch der Pharmazeutischen Technologie*. Stuttgart: Wissenschaftliche Verlagsgesellschaft mbH; pp. 313-316, with English translation (13 pages total).

Bavin, M. (Aug. 1989) "Polymorphism in Process Development" *Chemistry & Industry*, 16:527-529.

Bazant, V. et al. (Jan. 1968) "Properties of sodium-bis-(2-methoxyethoxy)aluminumhydride. I. Reduction of some organic functional groups" *Tetrahedron Letters*, 9(29):3303-3306.

Becq, F. et al. (2009) "Pharmacological therapy for cystic fibrosis: From bench to bedside" *J. Cystic Fibrosis*, vol. 10 supplement, 2:S129-S145.

Bell, T.W. et al. (Oct. 16, 1995) "Highly Effective Hydrogen-Bonding Receptors for Guanine Derivatives" *Angewandte Chemie—International Edition*, 34(19):2163-2165.

Bernstein, J. (2002) *Polymorphism in Molecular Crystals*. Oxford: Oxford Science Publications; Chapters 1 and 7, pp. 1-28 and 240-256.

Bernstein, J. (2002) *Polymorphism in Molecular Crystals*. Oxford: Oxford Science Publications; pp. 9-10.

Bhalerao, U.T. et al. (Jul. 1995) "A mild and efficient method for the dehydrogenation of dihydropyrido-pyrimidinones and related compounds by using active $MnO_2$" *Indian J Chem*, 34B:587-590.

Bhattacharya, S. et al. (2009) "Thermoanalytical and Crystallographic Methods" in *Polymorphism in Pharmaceutical Solids*. 2nd edition. Harry G. Brittain (ed.) New York, NY: Informa Healthcare USA, Inc.; pp. 318-335.

Bombieri, C. et al. (1998) "Complete mutational screening of the CFTR gene in 120 patients with pulmonary disease" *Hum Genet*, 103:718-722.

Bombieri et al., "Recommendations for the classification of diseases of CFTR-related disorders," *J. Cyst Fibros* 10:2 S86-S102 (2011).

Boyle, M.P. et al. (Oct. 1, 2011) "VX-809, an Investigational CFTR Corrector, in Combination With VX-770, an Investigational CFTR Potentiator, in Subjects With CF and Homozygous for the F508del-CFTR Mutation" *Pediatric Pulmonology*, 46:287, Abstract 212.

Braga, D. et al. (2009) "Crystal Polymorphism and Multiple Crystal Forms" *Struct Bond*, 132:25-27.

Brittain (Ed.) (1999) *Polymorphism on Pharmaceutical Science*. NY:Marcel Dekker, Inc.; pp. 1-2, 183-226, 235-238.

Byrn, S. et al. (1995) "Pharmaceutical Solids: A Strategic Approach to Regulatory Considerations" *Pharmaceutical Research*, 12(7):945-954.

Cabeza, J. A. et al. (2004) "Triruthenium, Hexaruthenium, and Triosmium Carbonyl Derivatives of 2-Amino-6-phenylpyridine" *Organometallics*, 23(5):1107-1115.

Caira, M.R. (1998) "Crystalline Polymorphism of Organic Compounds" in *Topics in Current Chemistry*, vol. 198, pp. 163-208.

CAPLUS Database Accession No. 1960:17025; Document No. 54:17025. Ridi, M. (1959) *Annali di Chimica*, 49:944-957 (2 pages).

CAPLUS Database Accession No. 1970:435253; Document No. 73:352253. Van Allan, J.A. et al. (1970) *J Heterocycl Chem*, 7(3):495-507 (1 page).

CAPLUS Database Accession No. 1979:420373; Document No. 91:20373. Nantka-Namirski, P. et al. (1978) *Polish Journal of Pharmacology and Pharmacy*, 30(4):569-572 (2 pages).

CAPLUS Database Accession No. 1988:186521; Document No. 108:186521. Mertens, H. et al. (1987) *Archiv der Pharmazie*, 320(11):1143-1149 (2 pages).

(56) References Cited

OTHER PUBLICATIONS

CAPLUS Database Accession No. 1991:6375; Document No. 114:6375. Jure, M. et al. (1990) *Latvijas PSR Zinatnu Akademijas Vestis, Kimijas Serija*, 4:439-444 (3 pages).
CAPLUS Database Accession No. 1994:244582; Document No. 120:244582. Troscheutz, R. et al. (1994) *Archiv der Pharmazie*, 327(2):85-89 (1 page).
CAPLUS Database Accession No. 2005:406839; Document No. 143:248209; RN 134643-28-0. Spitzner (2005) *Science of Synthesis*, 15:11-284 (1 page).
Carnegie Mellon, Dept. Of Physics (2002) "CMU Seed Fund Project on Detection and Control of Pharmaceutical Polymorphism" [online]. Retrieved from the Internet: http://andrew.cmu.edu/user/suter/polymorph.html: on Apr. 3, 2008, 3 pages.
Cerny, M. et al. (Mar. 1969) "Properties of sodium bis(2-methoxyethoxy)aluminum hydride. III. Reduction of carboxylic acids and their derivatives" *Collection of Czechoslovak Chemical Communications, Institute of Organic Chemistry & Biochemistry*, 34(3):1025-1032.
Chueshov V.I. (2002) *Promyslenaya technologya lekarstv [Industrial technology of medicaments]*, vol. 2, Kharkov, NFAU Publishing House, MTK-Kniga, pp. 336-337.
Clancy, J.P. et al. (Jan. 2012) "Results of a phase IIa study of VX-809, an investigational CFTR corrector compound, in subjects with cystic fibrosis homozygous for the F508del-CFTR mutation" *Thorax*, 67(1):12-18. NIH Public Access Author Manuscript; available in PMC Aug. 19, 2013 (16 pages).
*Concise Encyclopedia Chemistry*, NY: Walter de Gruyter, 1993, pp. 872-873.
Corning Inc. (2013) "Corning® Gentest™ ATPase Assay Kit. Colorimetric Reagent Kit for ABC Transporter Membrane ATPase Assays" Product information, 2 pages.
Costa, M. et al. (Jun. 2005) "Diabetes: a major co-morbidity of cystic fibrosis" *Diabetes Metab*, 31(3 Pt 1):221-232 (French; English summary on p. 221).
Cowart, M. et al. (Jan. 2001) "Structure-activity studies of 5-substituted pyridopyrimidines as adenosine kinase inhibitors" *Bioorg Med Chem Lett*, 11(1):83-86.
Cystic Fibrosis Foundation (2006) *Annual Report*. (58 pages).
Dahl, M. et al. (Oct. 9, 2005) "Asthma and COPD in cystic fibrosis intron-8 5T carriers. A population-based study" *Respiratory Research*, 6:113, doi:10.1186/1465-9921-6-113, 9 pages.
Dahl, M. and B.G. Nordestgaard (2009) "Markers of early disease and prognosis in COPD" *Intl J COPD*, 4:157-167.
Damasio, A.R. (1996) "Alzheimer's Disease and Related Dementias" in *Cecil Textbook of Medicine*. 20th edition. J. Claude Bennett and F. Plum (Eds.). Philadelphia: W.B. Saunders Co.; vol. 2, pp. 1992-1996.
Danswan, G. et al. (1989) "Synthesis of (imidazo[1,2-C]pyrimidin-2-yl)phenylmethanones and 6-benzoylpyrrolo[2,3-D]pyrimidinones" *J Heterocyclic Chem*, 26(2):293-299.
Davidovich et al. (2004) "Detection of Polymorphism by Powder X-Ray Diffraction: Interference by Preferred Orientation" *American Pharmaceutical Review*, 7(1):10, 12, 14, 16 and 100.
Dhenge, R.M. et al. (2010) "Twin screw wet granulation: Granule properties" *Chemical Engineering Journal*, 164:322-329.
Doelker, E. (2002) "Modifications Cyrisallines et Transformations Polymorphes au Cours des Operations Galeniques (Crystalline Modifications and Polymorphous Changes During Drug Manufacture" English translation of *Ann. Pharm. Fr.*, 60:161-176 (40 pages).
Doelker, E. (1999) "Physicochemical Behaviors of Active Substances Their Consequences for the Feasibility and the Stability of Pharmaceutical Forms" *S.T.P. Pharma Pratiques*, 9(5):399-409. French with English translation.
Dornow, A. and P. Karlson (1940) "Über eine neue Synthese von 2-Amino-pyridin-Derivaten" *Berichte der Deutschen Chemischen Gesellschaft A/B*, 73(5):542-546.
Dornow, A. and E. Neuse (1951) "Über die Reaktion von Amidinen mit β-Dicarbonyl-Verbindungen" *Chemische Berichte*, 84:296-304 (German).
Dörwald, F.Z. (2005) *Side Reactions in Organic Synthesis*. Weinheim, Germany: Wiley-VCH; Preface, pp. 1-15 and Chapter 8, pp. 279-308.
Elkady, M. et al. (1980) "Some reactions of β-aroylacrylic acids" *Revue Roumanie de Chimie*, 25:1361-1366.
European Medicines Agency (Sep. 24, 2015) "Orkambi" *Assessment Report*. Procedure No. EMEA/H/C/003954/0000 (104 pages).
European Patent Application No. 11715637.2 (Patent No. 2555755), filed Apr. 7, 2011, by Vertex Pharmaceuticals Inc.: Notice of Opposition by Alfred E. Tiefenbacher (GmbH & Co. KG), May 18, 2017 (19 pages).
European Patent Application No. 11715637.2 (Patent No. 2555755), filed Apr. 7, 2011, by Vertex Pharmaceuticals Inc.: Response to Notice of Opposition, by Carpmaels & Ransford, Nov. 8, 2017 (18 pages).
Evens, G. and P. Caluwe (1975) "Pyrido[2,3-d]pyrimidines. Latent 2-Aminonicotinaldehydes" *J Org Chem*, 40(10):1438-1439.
Farhanullah et al. (2003) "Synthesis of Aminonicotinonitriles and Diaminopyridines through Base-Catalyzed Ring Transformation of 2H-Pyran-2-ones" *J Org Chem*, 68(7):2983-2985.
Ferec, C. et al. (2012) "Assessing the Disease-Liability of Mutations in CFTR" *Cold Spring Harbor Perspect Med*, 2:a009480 (13 pages).
Florence, A.T. (2011) *Physicochemical Principles of Pharmacy*. Chapter 1, pp. 7-42.
Flume, P.A. (2012) "Ivacaftor in Subjects With Cystic Fibrosis Who Are Homozygous for the F508del-CFTR Mutation" *Chest*, 142(3):718-724.
Galietta, L.J.V. and O. Moran (2004) "Identification of CFTR activators and inhibitors: chance or design?" *Curr Opin Pharmacol*, 4:497-503.
Genomembrane Co. Ltd. (2015) "ABC Transporter and Assay" [online]. Retrieved from: http://www.genomembrane.com/E_ABC_Transporter_and_Assay.html; on Aug. 4, 2015 (3 pages).
Giardina, G.A.M. et al. (1999) "Replacement of the quinoline system in 2-phenyl-4-quinolinecarboxamide NK-3 receptor antagonists" *Il Farmaco*, 54:364-374.
Giron, D. (2001) "Investigations of polymorphism and pseudopolymorphism in pharmaceuticals by combined thermoanalytical techniques" *J Thermal Analysis Calorimetry*, 64:37-60.
Google.com (2016) "'new assay' cystic fibrosis transmembrane conductance regulator" Partial results of Internet search [online]. Retrieved from https://www.google.com; on Feb. 2, 2016 (2 pages).
Goshayev, M. et al. (1973) "Amination of 2-phenylpyridine under different conditions" *Izvestiya Akademii Nauk Turkmenskoi SSR, Seriya Giziko-Tekhnicheskikh, Khimicheskikh I Geologicheskikh Nauk*, 1973:108-109 (English abstract on p. 109).
Haleblian et al. (1969) "Pharmaceutical applications of polymorphism" *J Pharm Sci*, 58(8):911-929.
Hancock, B.C. and M. Parks (Apr. 2000) "What is the true solubility advantage for amorphous pharmaceuticals?" *Pharm Res*, 17(4):397-404.
HCAPLUS Database Accession No. 2005:823671 (2011) "Preparation of mainly N-thiazolyl carboxamides as modulators of ATP-binding cassette transporters" (3 pages).
Hirayama (Jul. 25, 2008) Yuuki kagoubutsu no kettshou sakusei handobuttku—genri to nouhou—(Handbook of preparation of crystal of organic compound—principle and know-how). Maruzen Co., Ltd, pp. 59-60 (Japanese).
Hisano, T. et al. (1982) "Reaction of Aromatic N-Oxides with Dipolarophiles. V. 1,3-Cycloaddition of 2-Substituted Pyridine N-Oxides with Phenyl Isocyanates" *Chem Pharm Bull*, 30(10):3776-3781.
International Patent Application No. PCT/US2006/043289, filed Nov. 8, 2006, by Vertex Pharmaceuticals Inc.: International Search Report and Written Opinion, dated Mar. 9, 2007.
International Patent Application No. PCT/US2006/049412, filed Dec. 28, 2006, by Vertex Pharmaceuticals Inc.: International Search Report and Written Opinion, dated Sep. 4, 2007.
International Patent Application No. PCT/US2008/063144, filed May 9, 2008, by Vertex Pharmaceuticals Inc.: International Search Report and Written Opinion, dated Mar. 24, 2009.

(56) References Cited

OTHER PUBLICATIONS

International Patent Application No. PCT/US2008/083517, filed Nov. 14, 2008, by Vertex Pharmaceuticals Inc.: International Search Report and Written Opinion dated Feb. 19, 2009.
International Patent Application No. PCT/US2008/085456, filed Dec. 4, 2008, by Vertex Pharmaceuticals Inc.: International Search Report and Written Opinion, dated Feb. 26, 2009.
International Patent Application No. PCT/US2008/085458, filed Dec. 4, 2008, by Vertex Pharmaceuticals Inc.: International Search Report and Written Opinion, dated Aug. 7, 2009.
International Patent Application No. PCT/US2009/035064, filed Feb. 25, 2009, by Vertex Pharmaceuticals Inc.: International Search Report and Written Opinion, dated Oct. 12, 2009.
International Patent Application No. PCT/US2009/038203, filed Mar. 25, 2009, by Vertex Pharmaceuticals Inc.: International Search Report and Written Opinion, dated Jul. 9, 2009.
International Patent Application No. PCT/US2009/058677, filed Sep. 29, 2009, by Vertex Pharmaceuticals Inc.: International Search Report and Written Opinion, dated Mar. 23, 2010.
International Patent Application No. PCT/US2011/031519, filed Apr. 7, 2011, by Vertex Pharmaceuticals Inc.: International Search Report and Written Opinion, dated Dec. 16, 2011.
International Patent Application No. PCT/US2011/031588, filed Apr. 7, 2011, by Vertex Pharmaceuticals Inc.: International Search Report and Written Opinion, dated Dec. 16, 2011.
International Patent Application No. PCT/US2011/033687, filed Apr. 22, 2011, by Vertex Pharmaceuticals Inc.: International Search Report and Written Opinion dated Aug. 30, 2011.
International Patent Application No. PCT/US2011/033689, filed Apr. 22, 2011, by Vertex Pharmaceuticals Inc.: International Search Report and Written Opinion dated Aug. 30, 2011.
International Patent Application No. PCT/US2013/023100, filed Jan. 25, 2013, by Vertex Pharmaceuticals Inc.: International Search Report and Written Opinion, dated May 7, 2013.
International Patent Application No. PCT/US2013/067952, filed Nov. 1, 2013, by Vertex Pharmaceuticals Inc.: International Search Report and Written Opinion, dated Feb. 5, 2014.
International Patent Application No. PCT/US2014/063506, filed Oct. 31, 2014, by Vertex Pharmaceuticals Inc.: International Search Report and Written Opinion, dated Jan. 21, 2015.
Ito, K. et al. (1989) "A New Route to 2-Amino- or 2-Hydroxy-3-pyridinecarboxylic Acid Derivatives" *J Heterocyclic Chem*, 26:773-778.
Itoh, T. and T. Mase (May 16, 2005) "Direct synthesis of heterobiaryl compounds containing an unprotected $NH_2$ group via Suzuki—Miyaura reaction" *Tetrahedron Lett*, 46(20):3573-3577.
Ivanisevic, I. et al. (Aug./Sep. 2011) "Uses of X-Ray Powder Diffraction in the Pharmaceutical Industry" *Pharmaceutical Formulation & Quality*, pp. 30-33.
Ivanova, L.A. (1991) English translation of: *Dosage form technology: a guide in 2 volumes*. vol. 2—M: Medicine, pp. 144-146 (translation 4 pages).
Jalgaonkar, S.V. et al. (2010) "ABC Membrane Transporters: Target for Drugs and Diseases" *Global J Pharmc*, 4(2):75-82.
Jain, N.K. and M.N. Mohammedi (1986) "Polymorphism in Pharmacy" *Indian Drugs*, 23(6):315-329.
Jonat, S. (2004) "Investigation of Compacted Hydrophilic and Hydrophobic Colloidal Silicon Dioxides As Glidants for Pharmaceutical Excipients" *Powder Technology*, 141:31-43.
Jones, P.M. and A.M. George (2004) "The ABC transporter structure and mechanism: perspectives on recent research" *Cell Mol Life Sci*, 61(6):682-699.
Jones, A.M. and J.M. Helm (2009) "Emerging Treatments in Cystic Fibrosis" *Drugs*, 69(14):1903-1910.
Jure, M. et al. (1990) "Synthesis of 3-Alkyl-5-Phenyl-7-Trifluoromethylimidazo[4,5-b]pyridin-2-ones" *Latvijas PSR Zinatnu Akademijas Vestis, Kimijas Serija*, 1990(4):439-444 (English summary on p. 444).

Kaczmarek, L. et al. (Aug. 1, 1992) "An Excellent Method for the Mild and Safe Oxidation of N-Heteroaromatic Compounds and Tertiary Amines" *Chem Ber*, 125(8):1965-1966.
*Kagaku Zikken Sosaho Jokan (Chemical Experimental Procedures)*, vol. 1. Nankodo Co., Ltd., Nov. 20, 1963; pp. 366-399.
Kaminski, W. et al. (2006) "ABC A-subfamily transporters: Structure, function and disease" *Biochim Biophys Acta*, 1762(5):510-524.
Kanth, S. et al. (2005) "Multistep Synthesis of Pyrido[3',2':4,5]pyrrolo[3,2-d][1,3]oxazin-4(5H)-one from 2-Aminonicotinonitriles" *Heterocycles*, 65(6):1415-1423.
Katoh, A. et al. (1984) "Ring Transformation Reactions of 1-Substituted 2(1H)-Pyrimidinones and Related compounds with Active Methylene Compounds" *Chem Pharm Bull*, 32(8):2942-2946.
Kazuhide, A. (Sep. 20, 2002) *Iyakuhin no Takei Gensyo to Syouseki no Kagaku (Science of Polymorphisms and Crystallization of Drugs)*. Maruzen Planet Co., Ltd.; p. 273 (Japanese).
Kazuhide, A. (Sep. 20, 2002) *Iyakuhin no Takei Gensyo to Syouseki no Kagaku (Science of Polymorphisms and Crystallization of Drugs)*. Maruzen Planet Co., Ltd.; p. 273, 278, 305-317 (Japanese).
Keleb, E.I. et al. (2004) "Twin screw granulation as a simple and efficient tool for continuous wet granulation" *Intl J Pharmaceutics*, 273:183-194.
Kharkevich, D.A. (2006) *Pharmacology: Textbook*. 9th edition. M: GEOTAR-Media; p. 66 (Russian).
*Kirk-Othmer Encyclopedia of Chemical Technology*. vol. 8. John Wiley & Sons, Inc., 2002; pp. 95-147.
Koitz, G. et al. (1981) "Synthese und Fluoreszenzeigenschaften von cyansubstituierten 2-Aminopyridinen" *Monatshefte für Chemie*, 112:973-985. (German; English abstract on p. 973). Abstract p. 973.
Lachman, L. et al. (1990) *The Theory and Practice of Industrial Pharmacy*. 3rd Edition. Bombay, India: Varghese Publication House; pp. 221-222.
Layzer, R.B. (1996) "Section Five—Degenerative Diseases of the Nervous System" in *Cecil Textbook of Medicine*. 20th edition. J. Claude Bennett and F. Plum (Eds.). Philadelphia: W.B. Saunders Co.; vol. 2, pp. 2050-2057.
Levin, M.H. et al. (Apr. 2005) "CFTR-Regulated Chloride Transport at the Ocular Surface in Living Mice Measured by Potential Differences" *Invest Ophthalmol Vis Sci*, 46(4):1428-1434.
Lin, S. et al. (Dec. 2010) "Identification of Synergistic Combinations of F508del Cystic Fibrosis Transmembrane Conductance Regulator (CFTR) Modulators" *ASSAY Drug Dev Tech*, 8(6):669-684.
Liu, X. et al. (2011) "Progress in the Study on Physical Stability and Anti-aging of Solid Dispersion" *Chin JMAP*, 28(8):710-717. Chinese with English abstract on p. 710.
Liu, Y. et al. (2005) "Expression Profiling of ABC Transporters in a Drug-Resistant Breast Cancer Cell Line Using AmpArray" *Mol Pharmacol*, 68(2):430-438.
Mertens, H. et al. (1986) "Synthese von 2-Amino-3-nitropyridinen und -1,4-dihydropyridinen" *Liebigs Ann Chem*, 1986:380-383 (German; English abstract on p. 380).
Mertens, H. and R. Troschütz (1987) "Synthese von $N^2$-substituierten 2-Amino-3-nitropyridinen als Vorstufen von Pyrido[2,3-b]pyrazinen (3-Desazapteridinen)" *Arch Pharm (Weinheim)*, 320:1143-1149 (German; English abstract on p. 1143).
Muzaffar, N.A. and M.A. Sheikh (1979) "Polymorphism and Drug Availability. A Review" *J Pharmacy (Lahore)*, 1(1):59-66.
Narsaiah, B. et al. (1994) "A novel synthetic route to 2-amino-3-cyano-4-trifluoromethyl-6-substituted pyridines" *J Fluorine Chem*, 67:87-90.
Ngiam, N.S.P. et al. (2006) "Cystic fibrosis transmembrane conductance regulator (CFTR) gene mutations in Asians with chronic pulmonary disease: A pilot study" *J Cystic Fibrosis*, 5:159-164.
Nitta, M. et al. (1991) "On the Reaction of (Vinylimino)phosphoranes. Part 17. Preparation of N-Vinylcarbodiimides and Their [4+2] Cycloaddition with Several Dienophiles to Give Pyridine Ring System" *Bull Chem Soc Japan*, 64(4):1325-1331.
Noone, P.G. et al. (2001) "'CFTR-opathies': disease phenotypes associated with cystic fibrosis transmembrane regulator gene mutations" *Respiratory Research*, 2(6):328-332.
Notice of Allowance and Fee(s) Due for U.S. Appl. No. 12/114,935. Issued As U.S. Pat. No. 8,993,600.

(56) References Cited

OTHER PUBLICATIONS

Notice of Allowance and Fee(s) Due for U.S. Appl. No. 13/290,491, dated Oct. 25, 2012.
Notice of Allowance and Fee(s) Due for U.S. Appl. No. 13/871,349, dated Aug. 12, 2014.
Notice of Allowance and Fee(s) Due for U.S. Appl. No. 13/871,349, dated Apr. 17, 2015.
Notice of Allowance and Fee(s) Due for U.S. Appl. No. 13/871,349, dated Oct. 13, 2015.
Notice of Allowance and Fee(s) Due for U.S. Appl. No. 13/887,839, dated Jul. 7, 2014.
Notice of Allowance and Fee(s) Due for U.S. Appl. No. 13/887,839, dated Oct. 16, 2014.
Notice of Allowance and Fee(s) Due for U.S. Appl. No. 13/887,839, dated Feb. 2, 2015.
Notice of Allowance and Fee(s) Due for U.S. Appl. No. 13/887,839, dated Sep. 30, 2015.
Notice of Allowance and Fee(s) Due for U.S. Appl. No. 13/933,223, dated May 23, 2014.
Notice of Allowance and Fee(s) Due for U.S. Appl. No. 13/972,151, dated May 16, 2016.
Notice of Allowance and Fee(s) Due for U.S. Appl. No. 13/972,151, dated Sep. 8, 2016.
Notice of Allowance and Fee(s) Due for U.S. Appl. No. 14/027,791, dated Jul. 31, 2015.
Notice of Allowance and Fee(s) Due for U.S. Appl. No. 14/031,360, dated Aug. 14, 2014.
Notice of Allowance and Fee(s) Due for U.S. Appl. No. 14/286,708, dated Feb. 19, 2016.
Notice of Allowance and Fee(s) Due for U.S. Appl. No. 14/298,245, dated Jul. 21, 2015.
Notice of Allowance and Fee(s) Due for U.S. Appl. No. 14/298,245, dated Nov. 12, 2015.
Notice of Allowance and Fee(s) Due for U.S. Appl. No. 14/317,277, dated Feb. 24, 2016.
Notice of Allowance and Fee(s) Due for U.S. Appl. No. 14/326,930, dated Aug. 14, 2015.
Notice of Allowance and Fee(s) Due for U.S. Appl. No. 14/326,930, dated Dec. 8, 2015.
Notice of Allowance and Fee(s) Due for U.S. Appl. No. 14/334,902, dated Oct. 19, 2015.
Notice of Allowance and Fee(s) Due for U.S. Appl. No. 14/334,902, dated Feb. 18, 2016.
Notice of Allowance and Fee(s) Due for U.S. Appl. No. 14/532,791, dated Jul. 24, 2015.
Notice of Allowance and Fee(s) Due for U.S. Appl. No. 14/532,791, dated Nov. 6, 2015.
Notice of Allowance and Fee(s) Due for U.S. Appl. No. 14/532,791, dated Mar. 1, 2016.
Notice of Allowance and Fee(s) Due for U.S. Appl. No. 14/567,475, dated Sep. 21, 2015.
Notice of Allowance and Fee(s) Due for U.S. Appl. No. 14/567,475, dated Jan. 5, 2016.
Notice of Allowance and Fee(s) Due for U.S. Appl. No. 14/579,098, dated Feb. 1, 2016.
Notice of Allowability for U.S. Appl. No. 14/579,098, dated Apr. 18, 2016.
Notice of Allowance and Fee(s) Due for U.S. Appl. No. 14/579,098, dated May 12, 2016.
Notice of Allowance and Fee(s) Due for U.S. Appl. No. 14/598,560, dated Jan. 21, 2016.
Notice of Allowance and Fee(s) Due for U.S. Appl. No. 14/601,608, dated Dec. 15, 2015.
Notice of Allowance and Fee(s) Due for U.S. Appl. No. 14/656,043, dated Aug. 4, 2016.
Notice of Allowance and Fee(s) Due for U.S. Appl. No. 14/687,286, dated Feb. 10, 2016.
Notice of Allowance and Fee(s) Due for U.S. Appl. No. 14/687,286, dated May 19, 2016.
Notice of Allowance and Fee(s) Due for U.S. Appl. No. 14/687,286, dated Sep. 28, 2016.
Notice of Allowance and Fee(s) Due for U.S. Appl. No. 14/687,286, dated Dec. 1, 2017.
Notice of Allowance and Fee(s) Due for U.S. Appl. No. 14/687,286, dated May 9, 2018.
Notice of Allowance and Fee(s) Due for U.S. Appl. No. 14/730,726, dated Apr. 12, 2016.
Notice of Allowance and Fee(s) Due for U.S. Appl. No. 14/841,163, dated Jan. 11, 2016, Issue Fee paid Apr. 8, 2016.
Notice of Allowance and Fee(s) Due for U.S. Appl. No. 14/877,914, dated Jul. 27, 2016.
Notice of Allowance and Fee(s) Due for U.S. Appl. No. 14/877,914, dated Nov. 14, 2016.
Notice of Allowance and Fee(s) Due for U.S. Appl. No. 14/920,041, dated Jul. 21, 2017.
Notice of Allowance and Fee(s) Due for U.S. Appl. No. 14/925,804, dated May 17, 2016.
Notice of Allowance and Fee(s) Due for U.S. Appl. No. 15/001,036, dated Feb. 10, 2017.
Notice of Allowance and Fee(s) Due for U.S. Appl. No. 15/001,036, dated May 1, 2018.
Notice of Allowance and Fee(s) Due for U.S. Appl. No. 15/073,591, dated Sep. 28, 2016.
Notice of Allowance and Fee(s) Due for U.S. Appl. No. 15/078,800, dated Mar. 16, 2018.
Notice of Allowance and Fee(s) Due for U.S. Appl. No. 15/152,092, dated May 17, 2018.
Notice of Allowance and Fee(s) Due for U.S. Appl. No. 15/160,100, dated May 3, 2017.
Notice of Allowance and Fee(s) Due for U.S. Appl. No. 15/162,887, dated Apr. 28, 2017.
Notice of Allowance and Fee(s) Due for U.S. Appl. No. 15/152,092, dated Oct. 3, 2018.
Notice of Allowance and Fee(s) Due for U.S. Appl. No. 15/234,877, dated Jan. 11, 2018.
Notice of Allowance and Fee(s) Due for U.S. Appl. No. 15/297,983, dated May 18, 2017.
Notice of Allowance and Fee(s) Due for U.S. Appl. No. 15/342,999, dated Apr. 17, 2018.
Notice of Allowance and Fee(s) Due for U.S. Appl. No. 15/584,324, dated Nov. 20, 2017.
Notice of Allowance and Fee(s) Due for U.S. Appl. No. 14/676,205, dated May 24, 2018.
Notice of Allowance and Fee(s) Due for U.S. Appl. No. 14/686,117, dated Oct. 1, 2018.
Notice of Allowance and Fee(s) Due for U.S. Appl. No. 15/659,926, dated Nov. 15, 2018.
Notice of Opposition for EP U.S. Pat. No. 2555755, mailed May 18, 2017.
Ochiai, Michiko et al., United States Court of Appeals for the Federal Circuit 71 F.3d 1565; 1995, U.S. Patent and Trademark Office Board of Patent Appeals and Interferences. (U.S. Appl. No. 07/462,492).
Ogata, A. (Nov. 20, 1963) *Process of Chemical Experiment. First Volume.* 27th Ed. Nankodo Co., Ltd.; pp. 366-399 (Japanese).
Okiyoneda, T. and G.L. Lukacs (Oct. 15, 2012) "Fixing cystic fibrosis by correcting CFTR domain assembly" *J Cell Biol*, 199(2):199-204.
Otsuka, M. et al. (1999) "Effect of Polymorphic Forms of Bulk Powders on Pharmaceutical Properties of Carbamazepine Granules" *Chem Pharm Bull*, 47(6):852-856.
Paranjape, S.M. et al. (2008) "Atypical Cystic fibrosis and CFTR-Related Diseases" *Clinic Rev Allerg Immunol*, 35(3):116-123.
Patani, G. et al. (1996) "Bioisosterism: A Rational Approach in Drug Design" *Chem Rev*, 96(8):3147-3176.
Pettit, R.S. (2012) "Cystic Fibrosis Transmembrane Conductance Regulator-Modifying Medications: The Future of Cystic Fibrosis Treatment" *Ann Pharmacother*, 46(7/8):1065-1075.
Qiao, J. X. et al. (Nov. 2, 2004) "5-Amidinobenzo[b]thiophenes as dual inhibitors of factors IXa and Xa" *Bioorg Med Chem Lett*, 15(1):29-35.

(56) References Cited

OTHER PUBLICATIONS

Rathore, A.S. et al. (May 18, 2010) "Process analytical technology (PAT) for biopharmaceutical products" *Anal Bioanal Chem*, 398(1):137-154.
Registry Database RN 477866-05-0 (Dec. 31, 2002) "3-Pyridinecarboxylic acid, 5-cyano-2-phenyl-6-[(phenylmethyl)amino]—" Retrieved from STN [online]; retrieved on Nov. 28, 2016 (1 page).
Registry Database RN 478068-14-3 (Jan. 3, 2003) "3,4,5-Pyridinetricarbonitrile, 2-amino-6-(4-bromophenyl)—" Retrieved from STN [online]; retrieved on Nov. 28, 2016 (1 page).
Registry Database RN 478068-16-5 (Jan. 3, 2003) "3,4,5-Pyridinetricarbonitrile, 2-amino-6-[4-(trifluoromethyl)phenyl]—" Retrieved from STN [online]; retrieved on Nov. 28, 2016 (1 page).
Registry Database RN 478081-23-1 (Jan. 3, 2003) "3,4,5-Pyridinetricarbonitrile, 2-amino-6-(4-methylphenyl)—" Retrieved from STN [online]; retrieved on Nov. 28, 2016 (1 page).
Registry Database RN 881299-60-1 (Apr. 20, 2006) "3-Pyridinecarbonitrile, 6-(4-methoxyphenyl)-2-[(1-phenylethyl)amino]—" Retrieved from STN [online]; retrieved on Nov. 28, 2016 (1 page).
Registry Database RN 881300-29-4 (Apr. 20, 2006) "3-Pyridinecarbonitrile, 6-(4-methoxyphenyl)-2-(phenylamino)—" Retrieved from STN [online]; retrieved on Nov. 28, 2016 (1 page).
Registry Database RN 912772-80-6 (Nov. 9, 2006) "2,5 Pyridinediamine, 6-phenyl—" Retrieved from STN [online]; retrieved on Nov. 28, 2016 (1 page).
Registry Database RN 912772-97-5 (Nov. 9, 2006) "2-Pyridinamine, 5-nitro-6-phenyl—" Retrieved from STN [online]; retrieved on Nov. 28, 2016 (1 page).
Registry Database RN 925921-90-0 (Mar. 9, 2007) "2-Pyridinamine, 4-chloro-6-(2-methoxyphenyl)—" Retrieved from STN [online]; retrieved on Nov. 28, 2016 (1 page).
Registry Database RN 929400-78-2 (Apr. 8, 2007) "3-Pyridinecarbonitrile, 2-(cyclohexyllamino)-6-(4-methoxyphenyl)—" Retrieved from STN [online]; retrieved on Nov. 28, 2016 (1 page).
Registry Database RN 929443-65-2 (Apr. 9, 2007) "3-Pyridinecarbonitrile, 2-(cycloheptylamino)-6-(4-methoxyphenyl)—" Retrieved from STN [online]; retrieved on Nov. 28, 2016 (1 page).
Registry Database RN 929443-63-0 (Apr. 9, 2007) "3-Pyridinecarbonitrile, 6-(4-methoxyphenyl)-2-(4-piperidinylamino)—" Retrieved from STN [online]; retrieved on Nov. 28, 2016 (1 page).
Ridi, M. (1959) "Richerch sopra derivati della piridina. Nota II. Richerche sopra sistemi 3 H-1,2,6,7,9-pentaazafenalenci, piri-do(3,4-d)piridazinici e pirido(2,3-d)pirimidinici" *Annali di Chimica*, 49:944-957 (Italian).
Robins, R.K. and G.H. Hitchings (1958) "Studies on Condensed Pyrimidine Systems. XIX. A New Synthesis of Pyrido [2,3-d] pyrimidines. The Condensation of 1,3-Diketones and 3-Ketoaldehydes with 4-Aminopyrimidines" *J Am Chem*, 80(13):3449-3457.
Rodon, J. et al. (2010) "Combining Targeted Therapies: Practical Issues to Consider at the Bench and Bedside" *The Oncologist*, 15:37-50.
Rodríguez-Spong, B. et al. (2004) "General principles of a pharmaceutical solid polymorphism: a supramolecular perspective" *Adv Drug Delivery Reviews*, 56:241-274.
Rouhi, A.M. (2003) "The Right Stuff. From research and development to the clinic, getting drug crystals right is full of pitfalls" *Chem Eng News*, 81(8):32-35.
Rowland, M. and T.N. Tozer (1995) *Clinical Pharmacokinetics. Concepts and Applications*. p. 123.
Saito, T. et al. (1993) "Lewis Acid-Induced Hetero Diels-Alder Reaction of Conjugated Carbodiimides" *Chem Lett*, pp. 1127-1130.
Saito, T. et al. (1998) "Thermal or Lewis acid-promoted electrocyclisation and hetero Diels-Alder cycloaddition of α,β-unsaturated (conjugated) carbodiimides: a facile synthesis of nitrogen-containing heterocycles" *J Chem Soc Perkin Trans*, 1:3065-3080.

Santa Cruz Biotechnology, Inc. "Polyvinylpyrrolidone" Material Safety Data Sheet, Catalog No. sc-203204; Issue Date: Apr. 5, 2009, Print Date: Feb. 17, 2011 (8 pages).
Schmidt, H-W. et al. (1980) "Synthesen mit Nitrilen; 59[1]. Ein einfacher Weg zu 2-Amino-3,4,5-tricyanopyridinen" *Synthesis*, 1980(6):471-472. (German).
Schultheiss, N. et al. (2009) "Pharmaceutical Cocrystals and Their Physiochemical Properties" *Crystal Growth & Design*, 9(6):2950-2967.
Shadan Houjin Nihon Kagakukai Edi., Shin-Jikkenn Kagaku Kouza 14, Yukikagoubutsu no Gousei to Hannou I, Maruzen Corp., 1977, p. 477.
Shah, U. and L. Augsburger (2002) "Multiple Sources of Sodium Starch Glycolate, NF: Evaluation of Functional Equivalence and Development of Standard Performance Tests" *Pharmaceutical Development and Technology*, 7(3):345-359.
Shin Iyakuhin no Kikaku Oyobi Shikenhouhou no Settei (translator's note: translated as Setting of Standards and Testing Methods of New Medicaments) (Pharmaceutical Affairs Bureau Notification No. 568).
Silverman, R.B. (1993) *The Organic Chemistry of Drug Design and Drug Action*. Academic Press Inc.; pp. 72-76.
Silverman, R.B (2004) *The Organic Chemistry of Drug Design and Drug Action*. 2nd Ed. Elsevier Academic Press; pp. 26 and 29-32.
Singhal, D. and W. Curatolo (2004) "Drug Polymorphism and dosage form design: a practical perspective" *Advanced Drug Delivery Reviews*, 56:335-347.
Stankovic, M. et al. (2008) "The CFTR M470V gene variant as a potential modifier of COPD severity: study of Serbian population" *Genetic Testing*, 12(3):357-362.
Suloeva, E. et al. (2001) "Synthesis of 5-Phenyl-7-trifluoromethyl-2,3-dihydroimidazo[1,2-a]pyridines" *Chem Heterocyclic Compounds*, 37:329-337.
Taday, P.F. et al. (2003) "Using Terahertz Pulse Spectroscopy to Study the Crystalline Structure of a Drug: A Case Study of the Polymorphs of Ranitidine Hydrochloride" *J Pharm Sci*, 92(4):831-838.
Takata, N. (2007) "Active pharmaceutical ingredient form screening and selection at the stage of drug discovery" *Pharm Stage*, 6(10):20-25 (Japanese).
The Associated Press (Sep. 24, 2003) "FDA mulls drug to slow late-stage Alzheimer's" CNN.com/HEALTH [online]. Retrieved from: http://www.cnn.com/2003/HEALTH/conditions/09/24/alzheimers.drug.ap/index.html, on Sep. 24, 2003 (2 pages).
The Chemical Society of Japan (1991) Jittuken kagaku kouza (Experimental Chemistry Course) 1, Fourth edition, Basic operation I, Nov. 5, 1990, Maruzen Co., Ltd, pp. 184-186 (Japanese).
Third Party Observation for EP Patent Application No. 20130792149, filed Jun. 13, 2018.
Troschütz, R. (1979) "6-Substituierte 2-Aminonicotinsäure-ethylester" *Archiv der Pharmazie*, 312:455-457 (German).
Troschütz, R. and A. Lückel (1992) "Synthese von substituierten 2-Amino-3-nitropyridinen aus 1,3-Biselektrophilen and 2-Nitroethen-1,1-diamin" *Archiv der Pharmazie*, 325(12):785-789 (German; English abstract on p. 785).
Troschütz, R. and T. Dennstedt (1994) "Synthese von substituierten 2-Aminonicotinonitrilen" *Archiv der Pharmazie*, 327:33-40 (German; English abstract on p. 33).
Troschütz, R. and T. Dennstedt (1994) "Substituierte 2-Aminonicotinonitrile" *Archiv der Pharmazie*, 327:85-89 (German; English abstract on p. 85).
Tzetis, M. et al. (2001) "CFTR gene mutations—including three novel nucleotide substitutions—and haplotype background in patients with asthma, disseminated bronchiectasis and chronic obstructive pulmonary disease" *Hum. Genet.*, 108:216-221.
U.S. Department of Health and Human Services, Food and Drug Administration (FDA) (May 1999) *Guideline for Industry. Container Closure Systems for Packaging Human Drugs and Biologics*. (56 pages).
U.S. Appl. No. 11/804,726, filed May 18, 2007, by Sara Hadida•Ruah.
U.S. Appl. No. 12/117,941, filed May 9, 2008.
U.S. Appl. No. 13/091,411, filed Apr. 21, 2011, by Tanoury et al.
U.S. Appl. No. 13/632,835, filed Oct. 1, 2012.

(56) References Cited

OTHER PUBLICATIONS

U.S. Appl. No. 14/077,885, filed Nov. 12, 2013, by Sheth et al.
U.S. Appl. No. 14/179,762, filed Feb. 13, 2014.
U.S. Appl. No. 14/444,451, filed Jul. 28, 2014.
U.S. Appl. No. 14/817,633.
U.S. Appl. No. 14/818,698.
U.S. Appl. No. 14/852,892, filed Sep. 14, 2015.
U.S. Appl. No. 14/870,592, filed Sep. 30, 2015, by Zha.
U.S. Appl. No. 14/876,525, filed Oct. 6, 2015.
U.S. Appl. No. 14/877,860, filed Oct. 7, 2015, by Strohmeier et al.
U.S. Appl. No. 14/877,914.
U.S. Appl. No. 14/920,041, filed Oct. 22, 2015.
U.S. Appl. No. 14/920,836, filed Oct. 22, 2015, by Rowe et al.
U.S. Appl. No. 14/925,804, filed Oct. 28, 2015.
U.S. Appl. No. 14/935,777, filed Nov. 9, 2015, by Alargova et al.
U.S. Appl. No. 14/951,142, filed Nov. 24, 2015, by Dokou et al.
U.S. Appl. No. 14/982,973, filed Dec. 29, 2015, by Hadida-Ruah et al.
U.S. Appl. No. 14/985,650, filed Dec. 31, 2015.
U.S. Appl. No. 14/992,132, filed Jan. 11, 2016.
U.S. Appl. No. 14/994,487, filed Jan. 13, 2016, by Hadida-Ruah et al.
U.S. Appl. No. 14/996,781, filed Jan. 15, 2016, Van Goor et al.
U.S. Appl. No. 15/001,036, filed Jan. 19, 2016.
U.S. Appl. No. 15/010,542, filed Jan. 29, 2016.
U.S. Appl. No. 15/035,969, filed May 11, 2016, by Swinney et al.
U.S. Appl. No. 15/043,049, filed Feb. 12, 2016.
U.S. Appl. No. 15/056,313, filed Feb. 29, 2016.
U.S. Appl. No. 15/056,436, filed Feb. 29, 2016.
U.S. Appl. No. 15/064,222, filed Mar. 8, 2016, by Bhalchandra Ambhaikar et al.
U.S. Appl. No. 15/073,591, filed Mar. 17, 2016.
U.S. Appl. No. 15/078,800, filed Mar. 23, 2016.
U.S. Appl. No. 15/093,582, filed Apr. 7, 2016.
U.S. Appl. No. 15/097,252, filed Apr. 12, 2016.
U.S. Appl. No. 15/136,159, filed Apr. 22, 2016.
U.S. Appl. No. 15/152,092, filed May 11, 2016.
U.S. Appl. No. 15/160,100, filed May 20, 2016, by Demattei et al. (published).
U.S. Appl. No. 15/162,887, filed May 24, 2016.
U.S. Appl. No. 15/170,263, filed Jun. 1, 2016, by Hadida-Ruah et al. (published).
U.S. Appl. No. 15/173,325, filed Jun. 3, 2016, by Hadida-Ruah et al. (published).
U.S. Appl. No. 15/181,114, filed Jun. 13, 2016, by Dokou et al. (published).
U.S. Appl. No. 15/234,877, filed Aug. 11, 2016, by Hadida-Ruah et al.
U.S. Appl. No. 15/253,636, filed Aug. 31, 2016, by Rowe et al.
U.S. Appl. No. 15/297,983, filed Oct. 19, 2016, by Hadida-Ruah et al. (published).
U.S. Appl. No. 15/342,999, filed Nov. 3, 2016, by Alargova et al.
U.S. Appl. No. 15/643,182, filed Jul. 6, 2017, by Frederick F. Van Goor, et al.
U.S. Appl. No. 15/898,683, filed Feb. 19, 2018, by Frederick F. Van Goor, et al.
U.S. Appl. No. 15/937,564, filed Mar. 27, 2018, by Frederick F. Van Goor, et al.
U.S. Appl. No. 15/949,404, filed Apr. 10, 2018, by Sara Sabina Hadida-Ruah et al.
U.S. Appl. No. 15/659,926, filed Jul. 26, 2017, by Sara S. Hadida-Ruah et al.
U.S. Appl. No. 16/035,938, filed Jul. 16, 2018, by Rossitza Gueorguieva Alargova et al.
U.S. Appl. No. 16/059,724, filed Aug. 9, 2018, by Tanoury et al.
U.S. Appl. No. 16/109,931, filed Aug. 23, 2018, by Keshavarz-Shokri et al.
*U.S. Pharmacopeia #28, National Formulary #23* (2005), p. 2711.
*U.S. Pharmacopia #23, National Formulary #18*, (1995), pp. 1843-1844.

Ulicky, L and T.J. Kemp (Eds.) (1992) *Comprehensive Dictionary of Physical Chemistry*. Czecho-Slovakia: ALFA/Ellis Horwood Ltd.; p. 21.
Van Goor, F. et al. (2011) "Correction of the F508del-CFTR protein processing defect in vitro by the investigational drug VX-809" *Proc Natl Acad Sci USA*, 108(46):18843-18848.
Van Goor, F. et al. (2006) "Rescue of $\Delta F580$-CFTR trafficking and gating in human cystic fibrosis airway primary cultures by small molecules" *Am J Physiol Lung Cell Mol Physiol*, 290(6):L1117-L1130.
Vanallan, J.A. et al. (Jun. 1970) "Reactions of Some 4-Methylene-4H-pyran Derivatives with Primary and Secondary Amines" *J Heterocyclic Chem*, 7:495-507.
Vertex Pharmaceuticals, Inc. (May 17, 2006) "Vertex Pharmaceuticals Initiates Phase I Development for VX-770 in Cystic Fibrosis. FDA Grants Fast Track Designation to VX-770" Press Release [online]. Retrieved from: http://investors.vrtx.com/releasedetail.cfm?ReleaseID=233045; on Jan. 19, 2015 (2 pages).
Vertex Pharmaceuticals, Inc. (Jun. 25, 2015) Summary Review of Regulatory Action for Lumacaftor/ivacaftor Tablets. U.S. FDA, Center for Drug Evaluation and Research, Division of Pulmonary, Allergy, and Rheumatology, Products, CDER; Director Badrul A. Chowdhury, MD, PhD.; Application No. 206038Orig1s000 (18 pages).
Vertex Pharmaceuticals, Inc. (2016) "ORKAMBI® (lumacaftor/ivacaftor tablets" Highlights of Prescribing Information, Revised Sep. 2016 (16 pages).
Wang, Y. et al. (2006) "Specific Rescue of Cystic Fibrosis Transmembrane Conductance Regulator Processing Mutants Using Pharmacological Chaperones" *Mol Pharmacol*, 70(1):297-302.
Wikipedia (Jul. 13, 2008) "ATP-binding cassette transporter" [online]. [Retrieved on Sep. 24, 2008]; Retrieved from the Internet: http://en.wikipedia.org/wiki/ATP-binding_cassette_transporter (6 pages).
Wikipedia (2009) "ATP-binding cassette transporter" [online]. Retrieved on Jul. 10, 2009, from the Internet: http://en.wikipedia.org/wiki/ATP-binding_cassette_transporter (20 pages).
Wikipedia (Aug. 6, 2009) "Pharmaceutical formulation" [online]. Retrieved on Jan. 22, 2010, from the Internet: http://en.wikipedia.org/w/index.php?title.Pharmaceutical_formulation&oldid-30640... (3 pages).
Wikipedia (2011) "Solid solution" [online]. Retrieved on Sep. 20, 2011, from the Internet: http://www.wikipedia.com (3 pages).
Xu, L. et al. (Feb. 2, 2009) "Multiple compounds determination and fingerprint analysis of *Lidanpaishi* tablet and keli by high-performance liquid chromatography" *Anal Chim Acta*, 633(1):136-148.
Yin, J. et al. (Jun. 2007) "A general and efficient 2-amination of pyridines and quinolines" *J Org Chem*, 72(12):4554-4557.
Yogi, S. et al. (1986) "Synthesis of Stable 1,2-Diazocines, 4,7-Disubstituted 3,8-Diaryl-1,2-diazacycloocta-2,4,6,8-tetraenes, and Their Termolysis" *Bull Chem Soc Jpn*, 59:1087-1094.
Yurugi, S. et al. (1972) "Studies on the Synthesis of N-Heterocyclic Compounds. XII. Syntheses of® Pyrido[3,4-d]pyridazine and Pyrido[2,3-d]pyridazine Derivatives" *Yakugaku Zasshi (Journal of the Pharmaceutical Society of Japan)*, 92(11):1333-1338. Japanese with English abstract on p. 1333.
Zhang, W. et al. (Mar. 2012) "Recent advances and new perspectives in targeting CFTR for therapy of cystic fibrosis and enterotoxin-induced secretory diarrheas" *Future Med Chem*, 4(3):329-345. NIH Author Manuscript; available in PMC Jan. 1, 2013 (28 pages).
"Material Safety Data Sheet—Croscamellose Sodium," *Spectrum*; 6 pages.
"Material Safety Data Sheet—Lauryl Sulfate Sodium," *Sigma-Aldrich*; 9 pages.
Aljaberi, A. et al., "Understanding and Optimizing the Dual Excipient Functionality of Sodium Lauryl Sulfate in Tablet Formulation of Poorly Water Soluble Drug: Wetting and Lubrication," *Pharmaceutical Development and Technology*, 2013, 18(2):490-503; © 2013 Informa Healthcare USA, Inc.
Esezobo, S., "The Effect of Some Excipients on the Physical Properties of a Paracetamol Tablet Formulation," *J. Pharm. Pharmacol*. 1985, 37:193-195; © 1985 J. Pharm. Pharmacol.

(56) References Cited

OTHER PUBLICATIONS

Bauer J.F. et al. (Sep. 2008) "Polymorphism—a critical consieration in pharmaceutical development, manufacturing, and stability"; *Journal of Validation Technology*, 14(5): 15-23.

Brittain, Harry G., "Polymorphism in Pharmaceutical Solids," 2008, pp. 334 and 338. 3 pages.

Cheng Yunzhang, "Engineering Principles and Equipment of Pharmaceutical Preparations", Southeast University Press, 1st edition, 2009, pp. 106-107.

Declaration of Jonathan Miller filed with the Response to Notice of Opposition of European Patent 2 914 248 B1 on Dec. 4, 2019, 7 pages.

Declaration of Patrick Connelly filed with the Response to Notice of Opposition of European Patent 2 914 248 B1 on Dec. 4, 2019, 3 pages.

Lachman, Leon et al., "The Theory and Practice of Industrial Pharmacy," Special Edition 2009, Copyright © Leon Lachman, PhD & Herbert A. Lieberman, PhD, p. 318. 4 pages.

Lieberman, Herbert A. et al., "Pharmaceutical Dosage Forms: Tablets, vol. 1," Second Edition, Revised, and Expanded; Copyright © 1989 by Marcel Dekker, Inc., 7 pages.

Marciel, Kristen K. et al., "Cell Phone Intervention to Improve Adherence: Cystic Fibrosis Care Team, Patient, and Parent Perspectives," National Institutes of Health, NIH Public Access, Pediatric Pulmonology Feb. 2010; 45(2): 157-164; © 2010 Wiley-Liss, Inc.; 13 pages.

Mathe, S. and A. Rassat (Jan. 29, 1998) "Synthesis of 1,1,1-Ethanetriacetonitrile, Precursor of 6-Substituted-4-methyl-2-aminopyridines" *Tetrahedron Lett*, 39:383-384.

Notice of Opposition for EP Patent No. 2555755, mailed May 18, 2017.

European Patent Application No. 13792149.0 (Patent No. 2914248), filed Nov. 1, 2013, by Vertex Pharmaceuticals Inc.: Response to Notice of Opposition, by Carpmaels & Ransford, Dec. 4, 2019 (211 pages).

European Patent Application No. 13792149.0 (Patent No. 2914248), filed Nov. 1, 2013, by Vertex Pharmaceuticals Inc.: Preliminary Opinion from European Opposition Division, Feb. 4, 2020 (21 pages).

Rowe, S.M. et al. (2005) "Cystic Fibrosis" *N Engl J Med*, 352(19):1992-2001.

Takata, N. (2009) "Cocrystal" *Pharm Tech Japan*, 25(12):155-166 (Japanese with English abstract).

U.S. Appl. No. 16/530,240, filed Aug. 2, 2019, by Marinus Jacobus Verwijs et al.

U.S. Appl. No. 16/704,713, filed Dec. 5, 2019, by Patricia Hurter et al.

U.S. Appl. No. 16/783,338, filed Feb. 6, 2020, by Ali Keshavarz-Shokri et al.

U.S. Appl. No. 16/789,945, filed Feb. 13, 2020, by Sara S. Hadida Ruah et al.

U.S. Appl. No. 16/842,480, filed Apr. 7, 2020, by William Rowe et al.

Vertex Pharmaceuticals, Inc. (Mar. 2011) "Study of VX-809 Alone and in Combination With VX-770 in Cystic Fibrosis (CF) Patients Homozygous for the F508del-CFTR Mutation" *ClinicalTrials.gov*[online]. Retrieved from: https://clinicaltrials.gov/archive/NCT01225211/2011_03_01; Identifier: NCT01225211.

Vertex Pharmaceuticals, Inc., Kalydeco® SmPC, published on Jul. 25, 2012, 33 pages.

Vertex Pharmaceuticals, Inc., Orkambi® SmPC, 98 pages.

Vertex Pharmaceuticals, Inc., Chowdhury, Badrul A., KALYDECO® FDA Summary Review, dated Jan. 27, 2019, 11 pages.

Vertex Pharmaceuticals, Inc., "Final Data from Phase 2 Combination Study of VX-809 and KALYDECO ™ (ivacaftor) Showed Statistically Significant Improvements in Lung Function in People with Cystic Fibrosis Who Have Two Copies of F508del Mutation," Press Release of Jun. 28, 2012, 5 pages.

Zhu, J. et al. (2006) "Solid-phase synthesis of 4-biaryl-piperidine-4-carboxamides" *Tetrahedron Lett*, 47:7267-7270.

Zhao, H., "New Technology for Modern Chinese Medicine Preparation," *Jiangsu Science and Technology Press*, Feb. 2007, 45 pgs. (Chinese followed by an English translation).

PHARMACEUTICAL COMPOSITIONS OF 3-(6-(1-(2,2-DIFLUOROBENZO[D][1,3]DIOXOL-5-YL)CYCLOPROPANECARBOXAMIDO)-3-METHYLPYRIDIN-2-YL) BENZOIC ACID AND ADMINISTRATION THEREOF

CROSS REFERENCE TO RELATED APPLICATIONS

This application is a Continuation of U.S. patent application Ser. No. 16/050,029 filed Jul. 31, 2018, which is now abandoned, which is a Continuation of U.S. patent application Ser. No. 15/001,036 filed Jan. 19, 2016, which is now U.S. patent Ser. No. 10/076,513, which is a Continuation of U.S. patent application Ser. No. 14/542,396 filed Nov. 14, 2014, which is now U.S. Pat. No. 9,241,934, which is a Continuation of U.S. patent application Ser. No. 14/031,360 filed Sep. 19, 2013, which is now abandoned, which is a Continuation of U.S. patent application Ser. No. 13/081,750 filed Apr. 7, 2011, which is now U.S. Pat. No. 8,552,034, and claims the benefit of priority under 35 U.S.C. § 119 to U.S. provisional patent application Ser. Nos. 61/321,748, filed Apr. 7, 2010; 61/321,729, filed Apr. 7, 2010; and 61/366,562, filed Jul. 22, 2010, the entire contents of both applications are incorporated herein by reference.

TECHNICAL FIELD OF INVENTION

The invention relates to pharmaceutical compositions comprising 3-(6-(1-(2,2-difluorobenzo[d][1,3]dioxol-5-yl)cyclopropanecarboxamido)-3-methylpyridin-2-yl)benzoic acid (Compound 1), methods for manufacturing such compositions and methods for administering pharmaceutical compositions comprising same.

BACKGROUND

CFTR is a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia lead to reduced apical anion secretion causing an imbalance in ion and fluid transport. The resulting decrease in anion transport contributes to enhance mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease-causing mutations (Cutting, G. R. et al. (1990) Nature 346:366-369; Dean, M. et al. (1990) Cell 61:863:870; and Kerem, B-S. et al. (1989) Science 245:1073-1080; Kerem, B-S et al. (1990) Proc. Natl. Acad. Sci. USA 87:8447-8451). To date, greater than 1000 disease-causing mutations in the CF gene have been identified as reported by the scientific and medical literature. The most prevalent mutation is a deletion of phenylalanine at position 508 of the CFTR amino acid sequence, and is commonly referred to as ΔF508-CFTR. This mutation occurs in approximately 70 percent of the cases of cystic fibrosis and is associated with a severe disease. Other mutations include the R117H and G551D.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl— channels expressed on the basolateral surface of the cell. Secondary active transport of chloride from the luminal side leads to the accumulation of intracellular chloride, which can then passively leave the cell via channels, resulting in a vectorial transport. Arrangement of $Na^+/2Cl^-/K^+$ co-transporter, $Na^+$—$K^+$-ATPase pump and the basolateral membrane K⁺ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective endoplasmic reticulum (ER) processing of ATP-binding cassette (ABC) transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)].

3-(6-(1-(2,2-Difluorobenzo[d][1,3]dioxol-5-yl) cyclopropanecarboxamido)-3-methylpyridin-2-yl)benzoic acid in salt form is disclosed in International PCT Publication WO 2007056341 as a modulator of CFTR activity and thus as a useful treatment for CFTR-mediated diseases such as cystic fibrosis. Form I of 3-(6-(1-(2,2-Difluorobenzo[d][1,3]dioxol-5-yl) cyclopropanecarboxamido)-3-methylpyridin-2-yl)benzoic acid, which is a substantially crystalline and salt-free form known as Compound 1 Form I, is disclosed in U.S. patent application Ser. No. 12/327,902, filed Dec. 4, 2008. Form II and HCl salt Form A of 3-(6-(1-(2,2-difluorobenzo[d][1,3]dioxol-5-yl) cyclopropanecarboxamido)-3-methylpyridin-2-yl)benzoic acid, Compound 1 Form II and Compound 1 HCl salt Form A, respectively, are disclosed in U.S. Provisional Patent Application 61/321,729, filed Apr. 7, 2010. All applications are incorporated in their entirety by reference herein. A need remains, however, for pharmaceutical compositions comprising Compound 1 Form I, Form II, or HCl salt Form A that are readily prepared and that are suitable for use as therapeutics.

SUMMARY

The invention relates to pharmaceutical compositions, pharmaceutical preparations, and solid dosage forms comprising 3-(6-(1-(2,2-difluorobenzo[d][1,3]dioxol-5-yl) cyclopropanecarboxamido)-3-methylpyridin-2-yl)benzoic acid (Compound 1) which has the structure below:

1

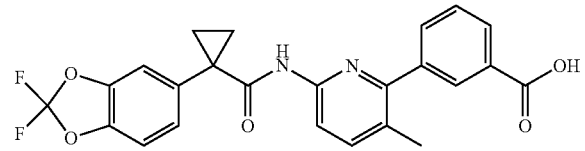

In one aspect, the invention provides a pharmaceutical composition comprising:
a. Compound 1;
b. a filler;
c. a disintegrant;
d. a surfactant;
e. a diluent;
f. a lubricant; and
g. at least one of a glidant and a binder.

In other embodiments, Compound 1 is in substantially one of its crystalline solid forms. In one embodiment, Compound 1 is in substantially crystalline Form I (Compound 1 Form I). In one embodiment, Compound 1 is in substantially crystalline Form II (Compound 1 Form II). In one embodiment, Compound 1 is in substantially crystalline HCl salt form (Compound 1 HCl Salt Form A). It is understood that the term "Compound 1," as used throughout, includes, amongst other forms, including non-crystalline forms, the following solid state forms: Compound 1 Form I, Compound 1 Form II, and/or Compound 1 HCl Salt Form A.

In some embodiments, the pharmaceutical composition comprises 25 mg to 400 mg. In some embodiments, the pharmaceutical composition comprises 25 mg of Compound 1. In some embodiments, the pharmaceutical composition comprises 50 mg of Compound 1. In some embodiments, the pharmaceutical composition comprises 100 mg of Compound 1. In some embodiments, the pharmaceutical composition comprises 125 mg of Compound 1. In some embodiments, the pharmaceutical composition comprises 150 mg of Compound 1. In some embodiments, the pharmaceutical composition comprises 200 mg of Compound 1. In some embodiments, the pharmaceutical composition comprises 250 mg of Compound 1. In some embodiments, the pharmaceutical composition comprises 400 mg of Compound 1.

In one aspect, the invention provides a pharmaceutical composition comprising the following components:

|  | (% w/w) |
| --- | --- |
| Roller Compaction Granule Blend | |
| Compound 1 | 20-40 |
| Microcrystalline cellulose | 30-50 |
| Mannitol | 10-30 |
| Croscarmellose Sodium | 1-5 |
| Sodium Lauryl Sulfate | 0.1-2 |
| Colloidal Silica | 0.1-1 |
| Magnesium Stearate | 1-3 |
| Tablet Composition (100 mg dose) | |
| Roller Compaction Granule Blend | 99-99.9 |
| Magnesium Stearate | 0.1-1 |

In another embodiment, the invention provides a pharmaceutical composition comprising the following components:

|  | (% w/w) |
| --- | --- |
| Roller Compaction Granule Blend | |
| Compound 1 Form I | 30 |
| Microcrystalline cellulose | 42.3 |
| Mannitol | 21.2 |
| Croscarmellose Sodium | 3 |
| Sodium Lauryl Sulfate | 1 |

-continued

|  | (% w/w) |
|---|---|
| Colloidal Silica | 0.5 |
| Magnesium Stearate | 2 |
| Tablet Composition (100 mg dose, 335 mg image) | |
| Roller Compaction Granule Blend | 99.5 |
| Magnesium Stearate | 0.5 |

In another aspect, the invention provides a pharmaceutical composition comprising the following components:

|  | (% w/w) |
|---|---|
| High Shear Granule Blend | |
| Compound 1 Form I | 40-80 |
| Microcrystalline cellulose | 20-40 |
| Mannitol | 10-15 |
| Croscarmellose Sodium | 1-5 |
| Polyvinylpyrrolidone | 1-10 |
| Sodium Lauryl Sulfate | 0.1-2 |
| Water (removed during drying) | 25-40% solids |
| Tablet Composition (100 mg dose) | |
| High Shear Granule Blend | 95-99 |
| Croscarmellose Sodium | 1-4 |
| Magnesium Stearate | 0.1-1 |

In another embodiment, the invention provides a pharmaceutical composition comprising the following components:

|  | (% w/w) |
|---|---|
| High Shear Granule Blend | |
| Compound 1 Form I | 50 |
| Microcrystalline cellulose | 30 |
| Mannitol | 13 |
| Croscarmellose Sodium | 2 |
| Polyvinylpyrrolidone | 4 |
| Sodium Lauryl Sulfate | 1 |
| Water (removed during drying) | 25-40% solids |
| Tablet Composition (100 mg dose, 205 mg image) | |
| High Shear Granule Blend | 97.5 |
| Croscarmellose Sodium | 2.0 |
| Magnesium Stearate | 0.5 |

In another embodiment, the invention provides a pharmaceutical composition comprising the following components:

|  | (% w/w) |
|---|---|
| High Shear Granule Blend | |
| Compound 1 Form I | 60 |
| Microcrystalline cellulose | 20 |
| Mannitol | 13 |
| Croscarmellose Sodium | 2 |
| Polyvinylpyrrolidone | 4 |
| Sodium Lauryl Sulfate | 1 |
| Water (removed during drying) | 25-40% solids |
| Tablet Composition (100 mg dose, 171 mg image) | |
| High Shear Granule Blend | 97.5 |
| Croscarmellose Sodium | 2.0 |
| Magnesium Stearate | 0.5 |

In another embodiment, the invention provides a pharmaceutical composition comprising the following components:

|  | (% w/w) |
|---|---|
| High Shear Granule Blend | |
| Compound 1 Form I | 60 |
| Microcrystalline cellulose | 20 |
| Mannitol | 13 |
| Croscarmellose Sodium | 2 |
| Polyvinylpyrrolidone | 4 |
| Sodium Lauryl Sulfate | 1 |
| Water (removed during drying) | 25-40% solids |
| Tablet Composition (200 mg dose, 402 mg image) | |
| High Shear Granule Blend | 83 |
| Microcrystalline cellulose | 14 |
| Croscarmellose Sodium | 2 |
| Magnesium Stearate | 1 |

In another embodiment, the invention provides a pharmaceutical composition comprising the following components:

|  | mg |
|---|---|
| High Shear Granule Blend | |
| Compound 1 Form I | 200 |
| Microcrystalline cellulose | 66 |
| Mannitol | 43 |
| Croscarmellose Sodium | 7 |
| Polyvinylpyrrolidone | 13 |
| Sodium Lauryl Sulfate | 3 |
| Core Tablet Composition (200 mg dose, 400 mg image) | |
| High Shear Granule Blend | 332 |
| Microcrystalline cellulose | 56 |
| Croscarmellose Sodium | 8 |
| Magnesium Stearate | 4 |
| Film Coated Tablet (200 mg dose, 412 mg image) | |
| Core Tablet Composition | 400 |
| Film Coat | 12 |
| Wax | 0.04 |

In another embodiment, the invention provides a pharmaceutical composition comprising the following components:

|  | mg |
|---|---|
| High Shear Granule Blend | |
| Compound 1 Form I | 200 |
| Microcrystalline cellulose | 67 |
| Mannitol | 45 |
| Croscarmellose Sodium | 7 |
| Polyvinylpyrrolidone | 10.4 |
| Sodium Lauryl Sulfate | 2.6 |
| Core Tablet Composition (200 mg dose, 400 mg image) | |
| High Shear Granule Blend | 332 |
| Microcrystalline cellulose | 56 |
| Croscarmellose Sodium | 8 |
| Magnesium Stearate | 4 |
| Film Coated Tablet (200 mg dose, 412 mg image) | |
| Core Tablet Composition | 400 |
| Film Coat | 12 |
| Wax | 0.04 |

In another embodiment, the invention provides a pharmaceutical composition comprising the following components:

|  | (% w/w) |
| --- | --- |
| High Shear Granule Blend | |
| Compound 1 Form I | 70 |
| Microcrystalline cellulose | 12 |
| Mannitol | 11 |
| Croscarmellose Sodium | 2 |
| Polyvinylpyrrolidone | 4 |
| Sodium Lauryl Sulfate | 1 |
| Water (removed during drying) | 25-40% solids |
| Tablet Composition (100 mg dose, 147 mg image) | |
| High Shear Granule Blend | 97.5 |
| Croscarmellose Sodium | 2.0 |
| Magnesium Stearate | 0.5 |

In another embodiment, the invention provides a pharmaceutical composition comprising the following components:

|  | (% w/w) |
| --- | --- |
| High Shear Granule Blend | |
| Compound 1 Form I or Form II | 61 |
| Microcrystalline cellulose | 20.3 |
| Mannitol | 13.2 |
| Croscarmellose Sodium | 2 |
| Polyvinylpyrrolidone | 2.7 |
| Sodium Lauryl Sulfate | 0.7 |
| Tablet Composition (100 mg dose, 197 mg image) | |
| High Shear Granule Blend | 83 |
| Microcrystalline cellulose | 14 |
| Croscarmellose Sodium | 2 |
| Magnesium Stearate | 1 |

In another embodiment, the invention provides a pharmaceutical composition comprising the following components:

|  | mg |
| --- | --- |
| High Shear Granule Blend | |
| Compound 1 Form I or Form II | 100 |
| Microcrystalline cellulose | 33.3 |
| Mannitol | 21.7 |
| Croscarmellose Sodium | 3.3 |
| Polyvinylpyrrolidone | 4.4 |
| Sodium Lauryl Sulfate | 1.1 |
| Core Tablet Composition (100 mg dose, 197 mg image) | |
| High Shear Granule Blend | 163.9 |
| Microcrystalline cellulose | 27.6 |
| Croscarmellose Sodium | 3.9 |
| Magnesium Stearate | 2.0 |

In another aspect, the invention provides a pharmaceutical composition in the form of a tablet that comprises Compound 1, and one or more pharmaceutically acceptable excipients, for example, a filler, a disintegrant, a surfactant, a diluent, a binder, a glidant, and a lubricant and any combination thereof, where the tablet has a dissolution of at least about 50% in about 30 minutes. In another embodiment, the dissolution rate is at least about 75% in about 30 minutes. In another embodiment, the dissolution rate is at least about 90% in about 30 minutes.

In another aspect, the invention provides a pharmaceutical composition consisting of a tablet that comprises a powder blend or granules comprising Compound 1; and, one or more pharmaceutically acceptable excipients, for example, a filler, a disintegrant, a surfactant, a diluent, a binder, a glidant, and a lubricant, wherein the tablet has a hardness of at least about 5 kP (kP=kilo Ponds; 1 kP=~9.8 N). In another embodiment, the tablet has a target friability of less than 1.0% after 400 revolutions. In another aspect, the invention provides a pharmaceutical composition consisting of a tablet that comprises a powder blend or granules comprising Compound 1 Form II, Compound 1; and, one or more pharmaceutically acceptable excipients, for example, a filler, a disintegrant, a surfactant, a diluent, a binder, a glidant, and a lubricant, wherein the tablet has a hardness of at least about 5 kP (kP=kilo Ponds; 1 kP=~9.8 N). In another embodiment, the tablet has a target friability of less than 1.0% after 400 revolutions.

In another aspect, the invention provides a pharmaceutical composition as described herein further comprising an additional therapeutic agent. In some embodiments, the additional therapeutic agent is N-(5-hydroxy-2,4-ditert-butyl-phenyl)-4-oxo-1H-quinoline-3-carboxamide.

In another aspect, the invention provides a method of treating a CFTR mediated disease in a mammal comprising administering to the mammal an effective amount of a pharmaceutical composition as described herein. In some embodiments, the CFTR mediated disease is cystic fibrosis, emphysema, COPD, or osteoporosis. In other embodiments, the CFTR mediated disease is cystic fibrosis. This method may further comprise administering an additional therapeutic agent, wherein in some embodiments, the additional therapeutic agent is N-(5-hydroxy-2,4-ditert-butyl-phenyl)-4-oxo-1H-quinoline-3-carboxamide.

In another aspect, the invention provides a process for making the pharmaceutical compositions described herein by a roller compaction process comprising the steps of screening and weighing Compound 1 and excipients; blending Compound 1 and excipients for a suitable amount of time; roller compacting the blend into ribbons and milling the ribbons into granules; blending the granules with extra-granular excipients for a suitable amount of time; compressing the blend into tablets; coating the tablets; and, optionally, printing a monogram on one or both tablet faces.

In another aspect, the invention provides a process for making the pharmaceutical compositions described herein by a high shear granulation process comprising the steps of screening and weighing Compound 1 and excipients; mixing Compound 1 and excipients while adding a granulation fluid comprising surfactant and a binder at a suitable mixing speed for a suitable amount of time and chopping the mixture into granules; drying the granules; blending the granules with extra-granular excipients for a suitable amount of time; compressing the blend into tablets; coating the tablets; and, optionally, printing a monogram on one or both tablet faces.

BRIEF DESCRIPTION OF DRAWINGS

FIG. 4 provides X-ray diffraction patterns of Compound 1 Form II's selected from:

1) Compound 1 Form II, Methanol Solvate;
2) Compound 1 Form II, Ethanol Solvate;
3) Compound 1 Form II, Acetone Solvate;
4) Compound 1 Form II, 2-Propanol Solvate;
5) Compound 1 Form II, Acetonitrile Solvate;
6) Compound 1 Form II, Tetrahydrofuran Solvate;
7) Compound 1 Form II, Methyl Acetate Solvate;
8) Compound 1 Form II, 2-Butanone Solvate;
9) Compound 1 Form II, Ethyl Formate Solvate; and
10) Compound 1 Form II, 2-Methyltetrahydrofuran Solvate.

Figure 5:
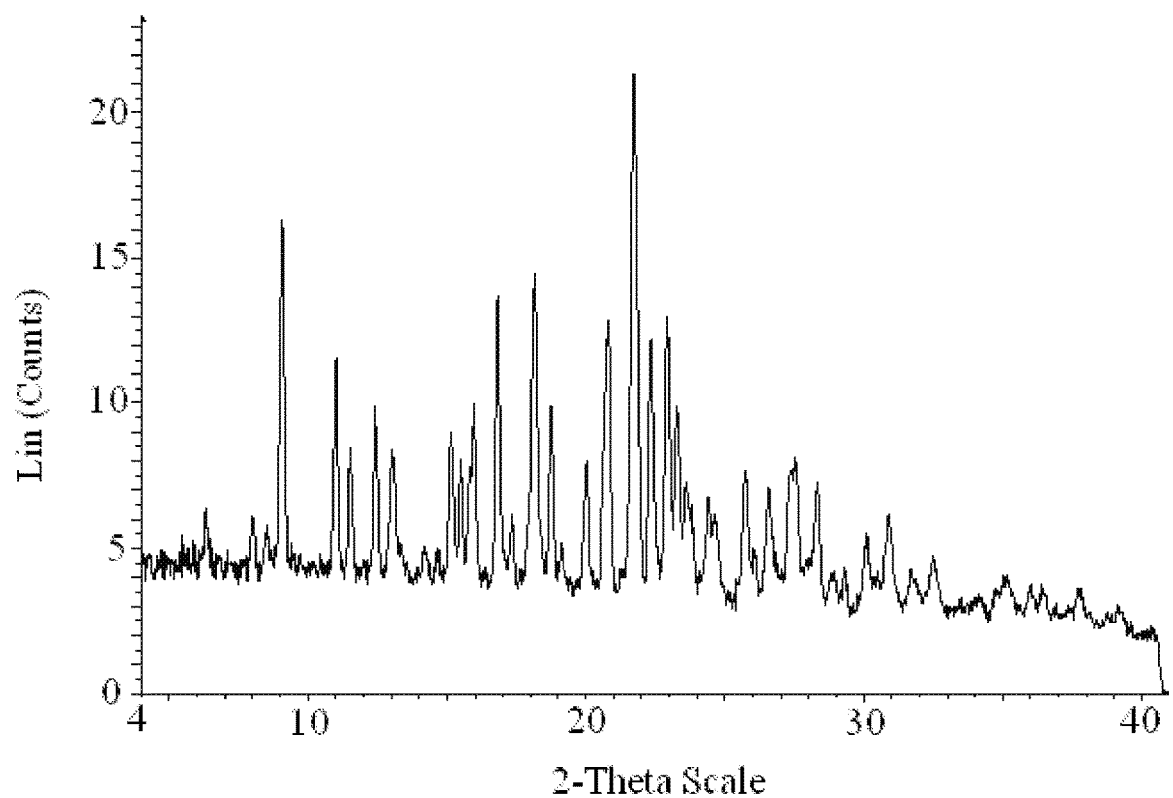

FIG. 5 provides an X-ray diffraction pattern of Compound 1 Form II, Methanol Solvate.

Figure 6:
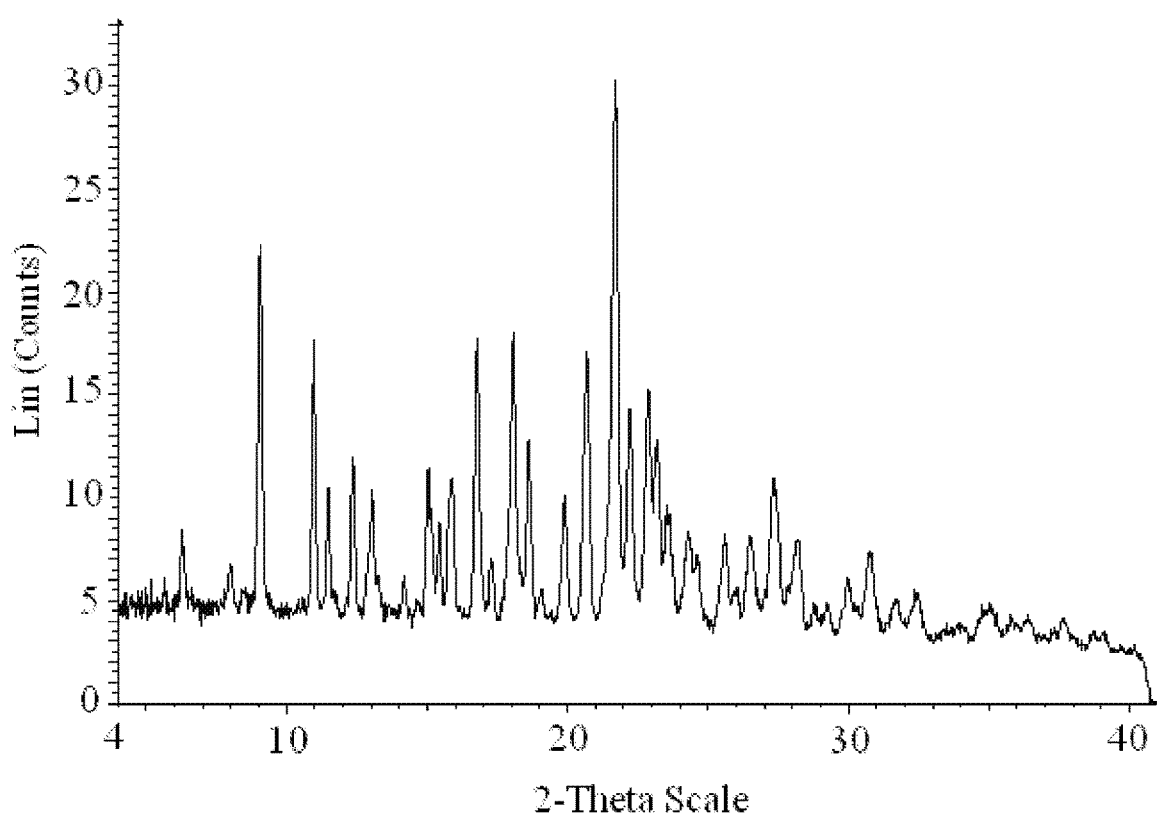

FIG. 6 provides an X-ray diffraction pattern of Compound 1 Form II, Ethanol Solvate.

Figure 7:
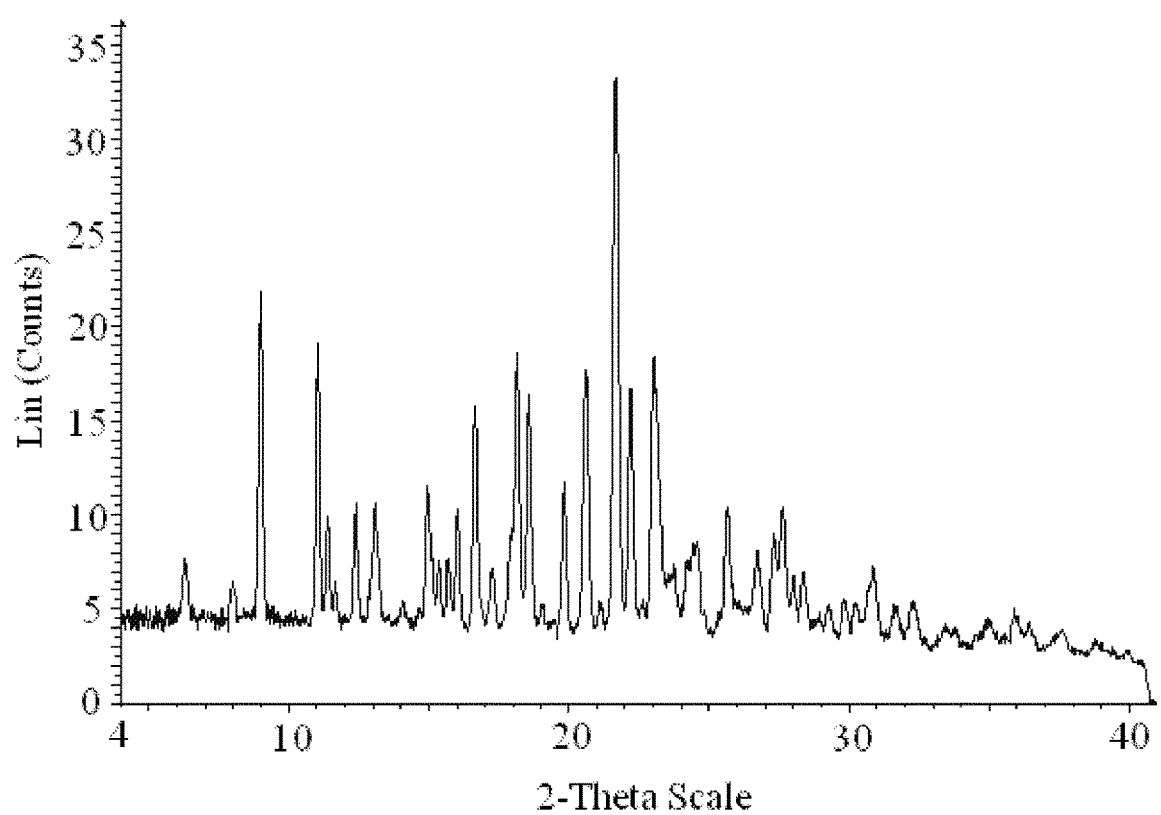

FIG. 7 provides an X-ray diffraction pattern of Compound 1 Form II, Acetone Solvate.

Figure 8:
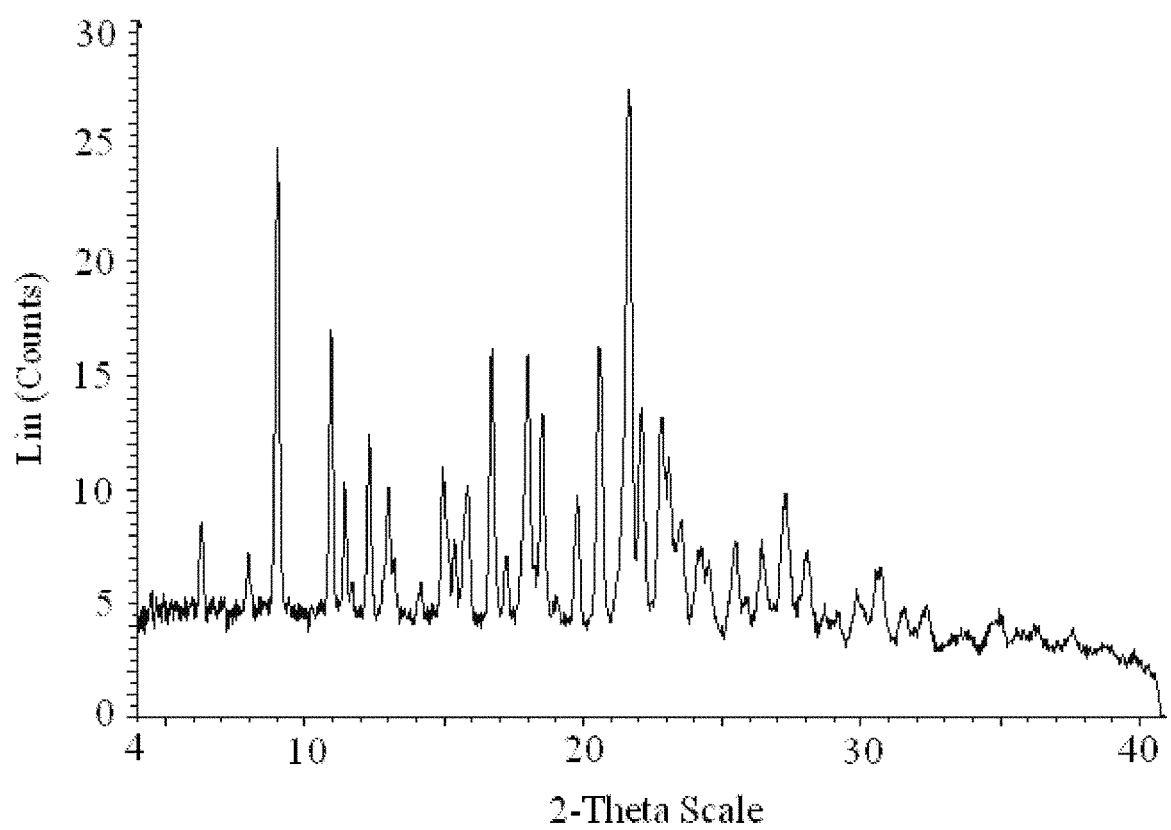

FIG. 8 provides an X-ray diffraction pattern of Compound 1 Form II, 2-Propanol Solvate.

Figure 9:
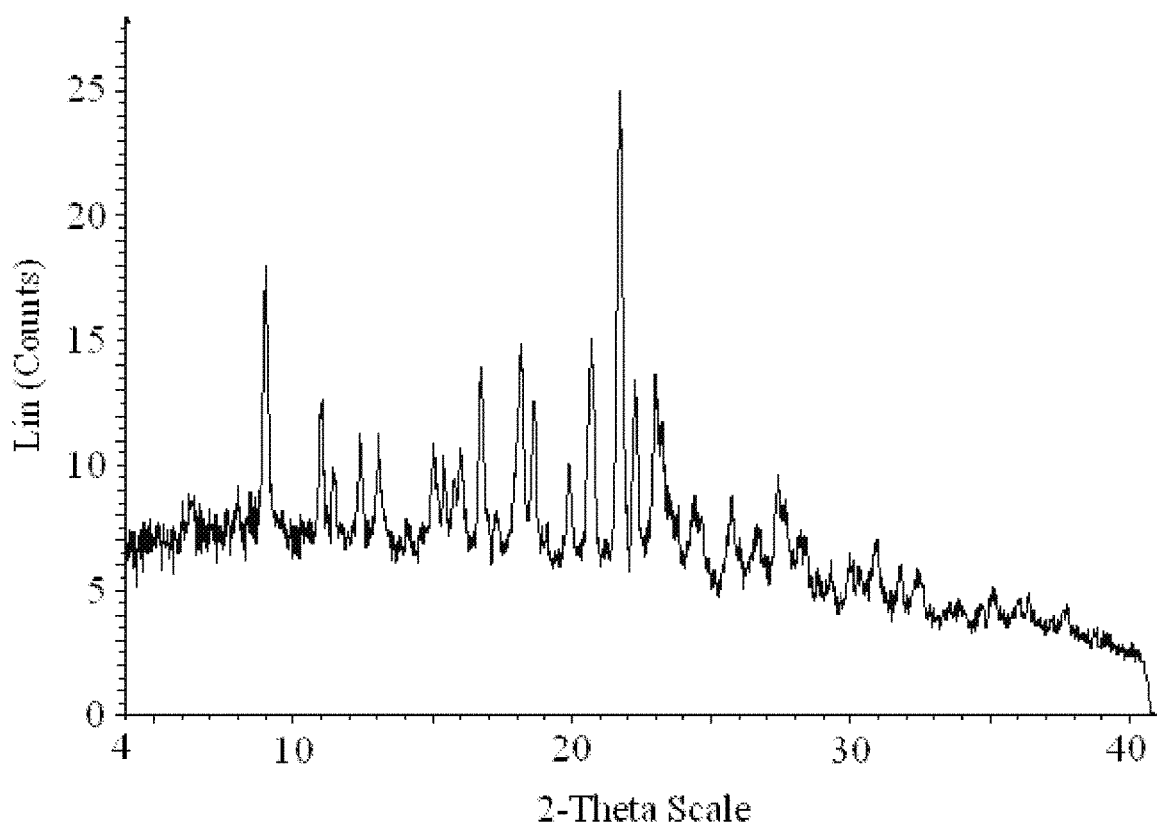

FIG. 9 provides an X-ray diffraction pattern of Compound 1 Form II, Acetonitrile Solvate.

Figure 10:
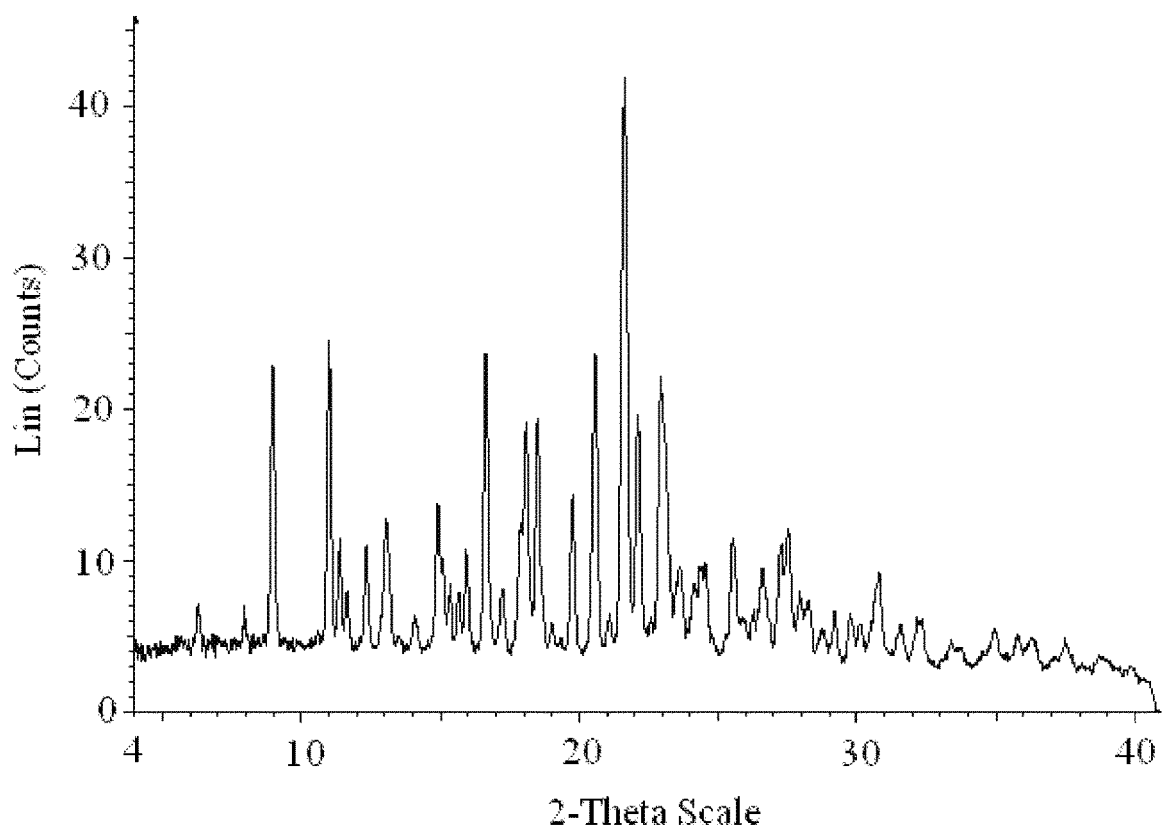

FIG. 10 provides an X-ray diffraction pattern of Compound 1 Form II, Tetrahydrofuran Solvate.

Figure 11:
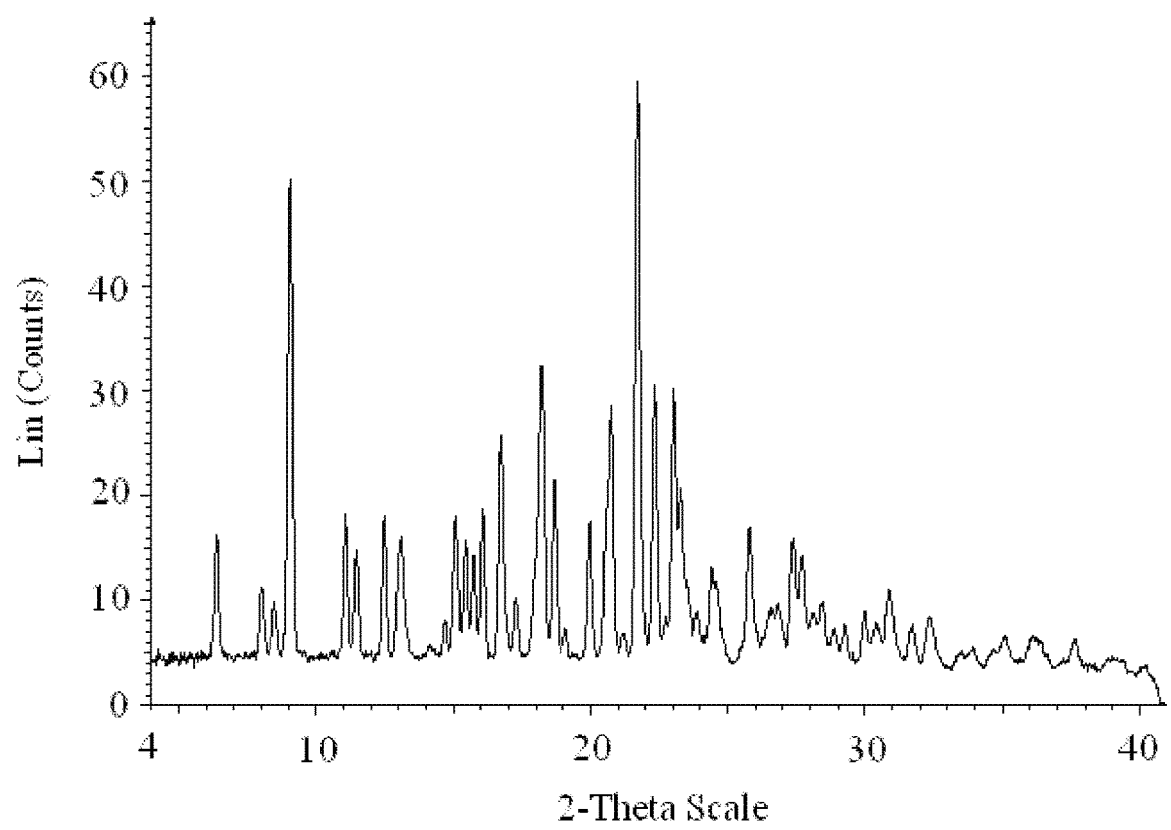

FIG. 11 provides an X-ray diffraction pattern of Compound 1 Form II, Methyl Acetate Solvate.

Figure 12:
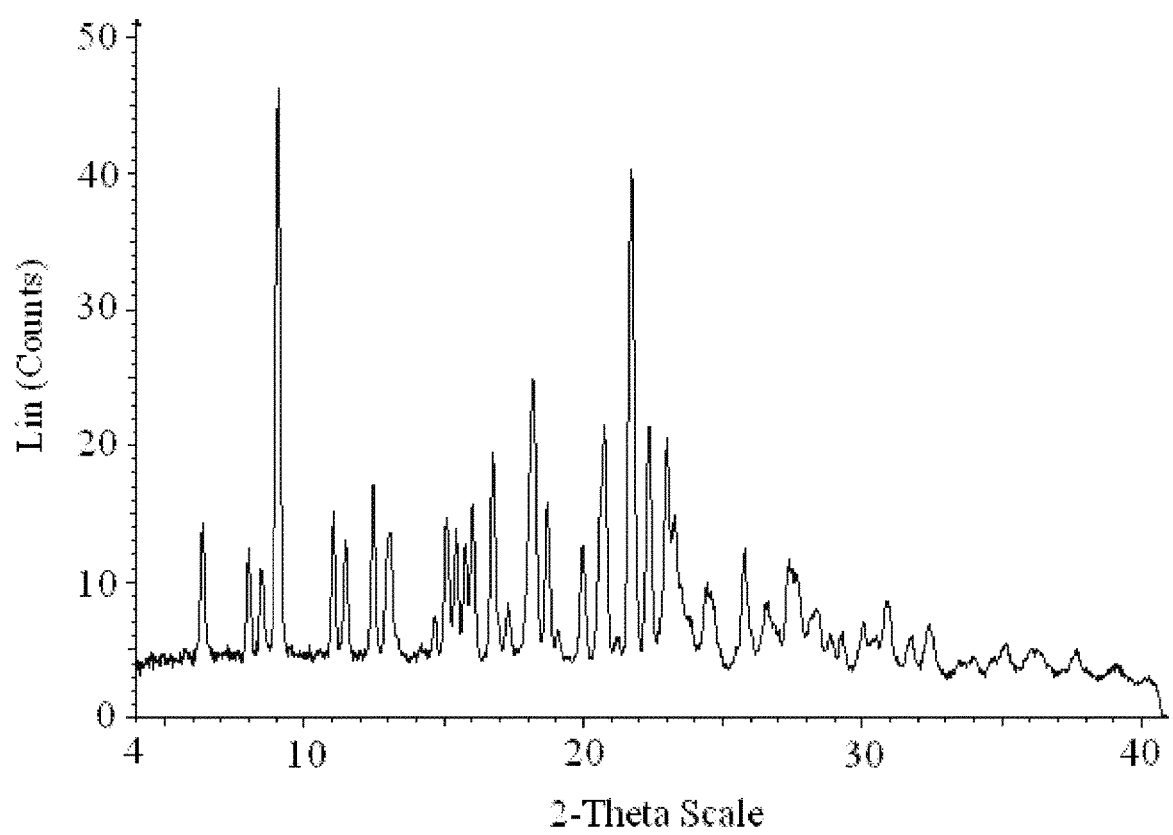

FIG. 12 provides an X-ray diffraction pattern of Compound 1 Form II, 2-Butanone Solvate.

Figure 13:
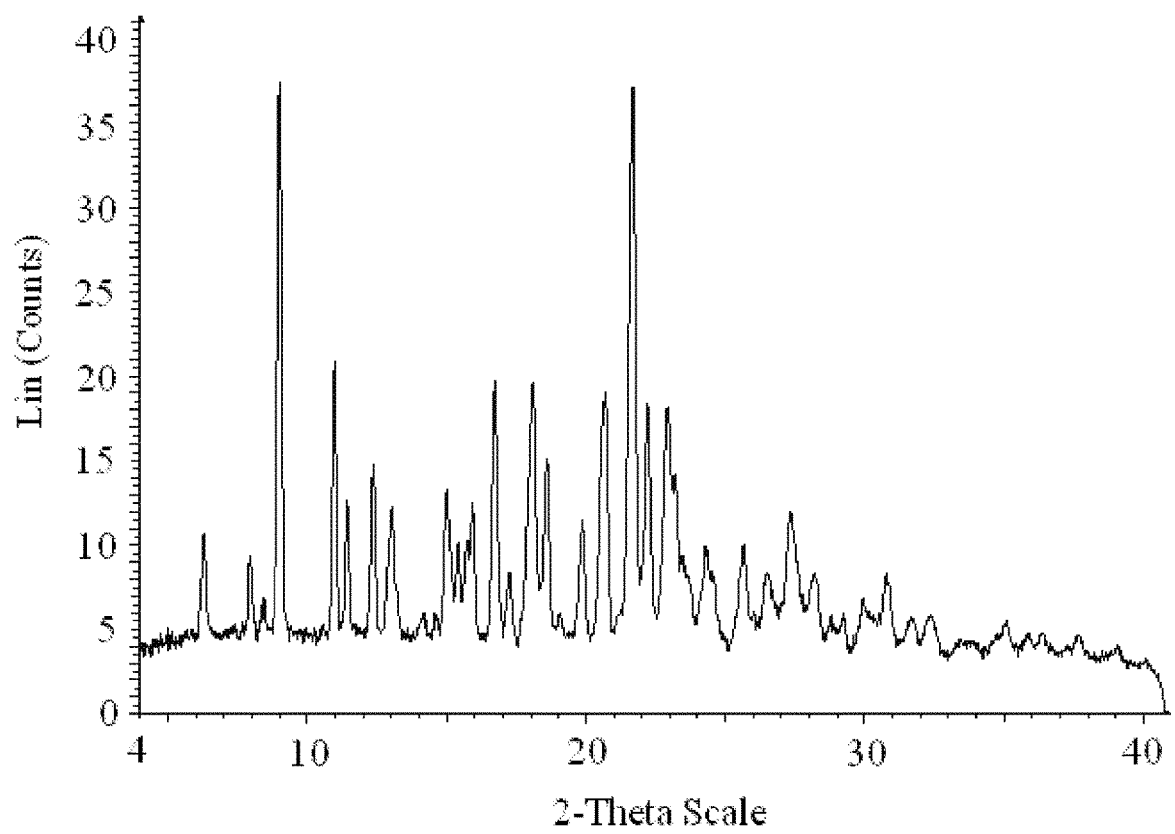

FIG. 13 provides an X-ray diffraction pattern of Compound 1 Form II, Ethyl Formate Solvate.

Figure 14:
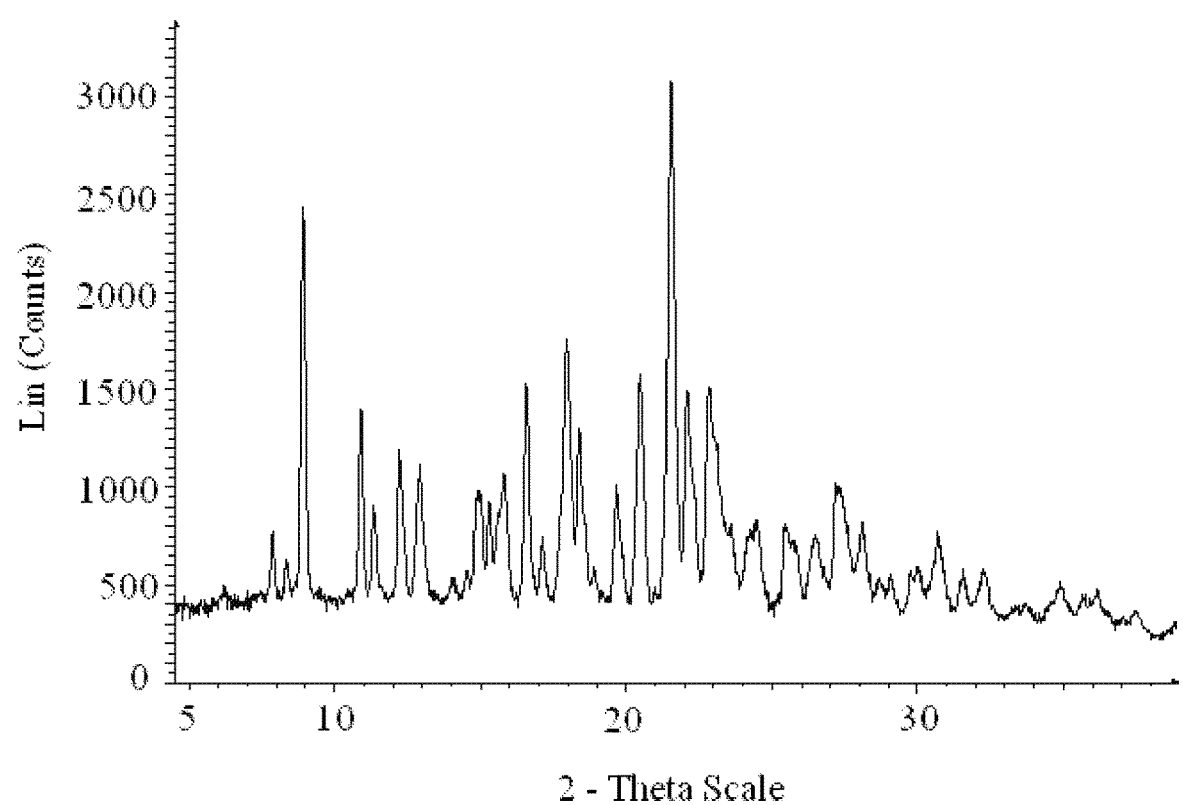

FIG. 14 provides an X-ray diffraction pattern of Compound 1 Form II, 2-Methyltetrahydrofuran Solvate.

Figure 15:
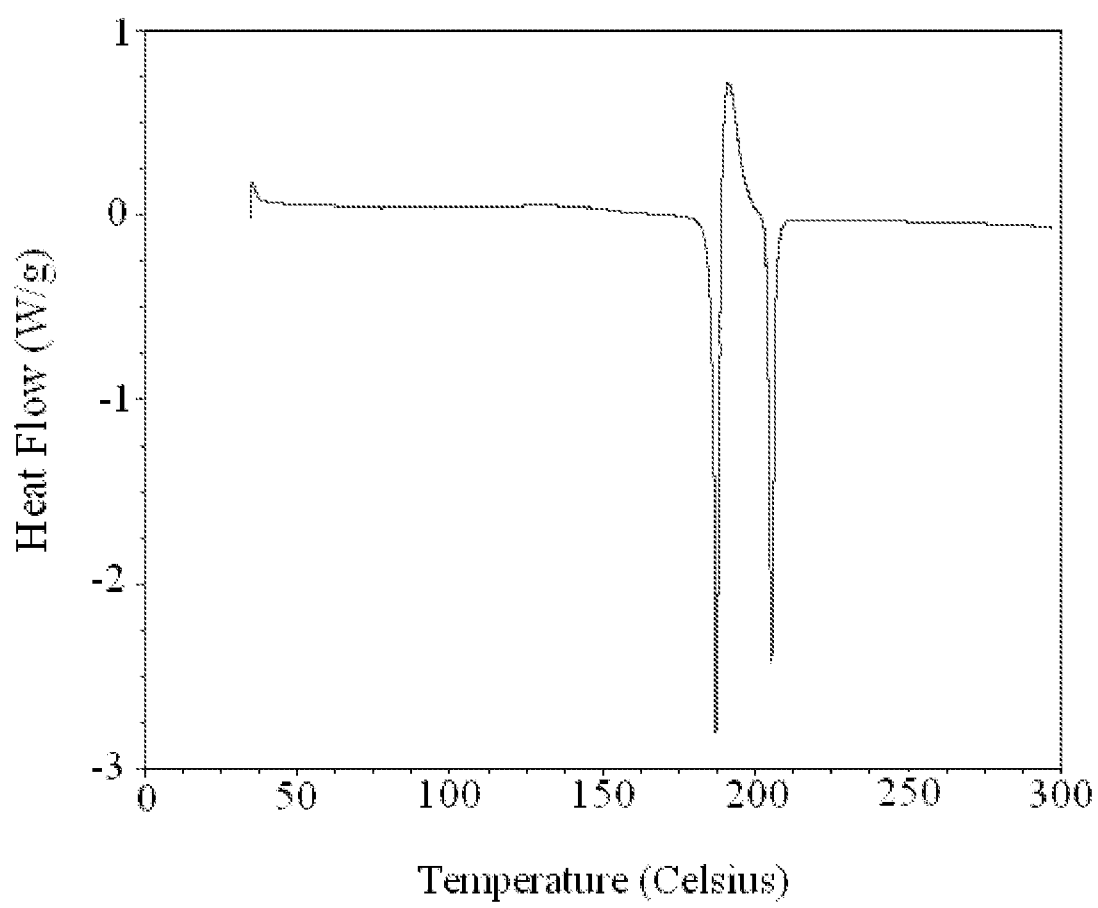

FIG. 15 is a differential scanning calorimetry (DSC) trace of Compound 1 Form II, Acetone Solvate.

Figure 16:
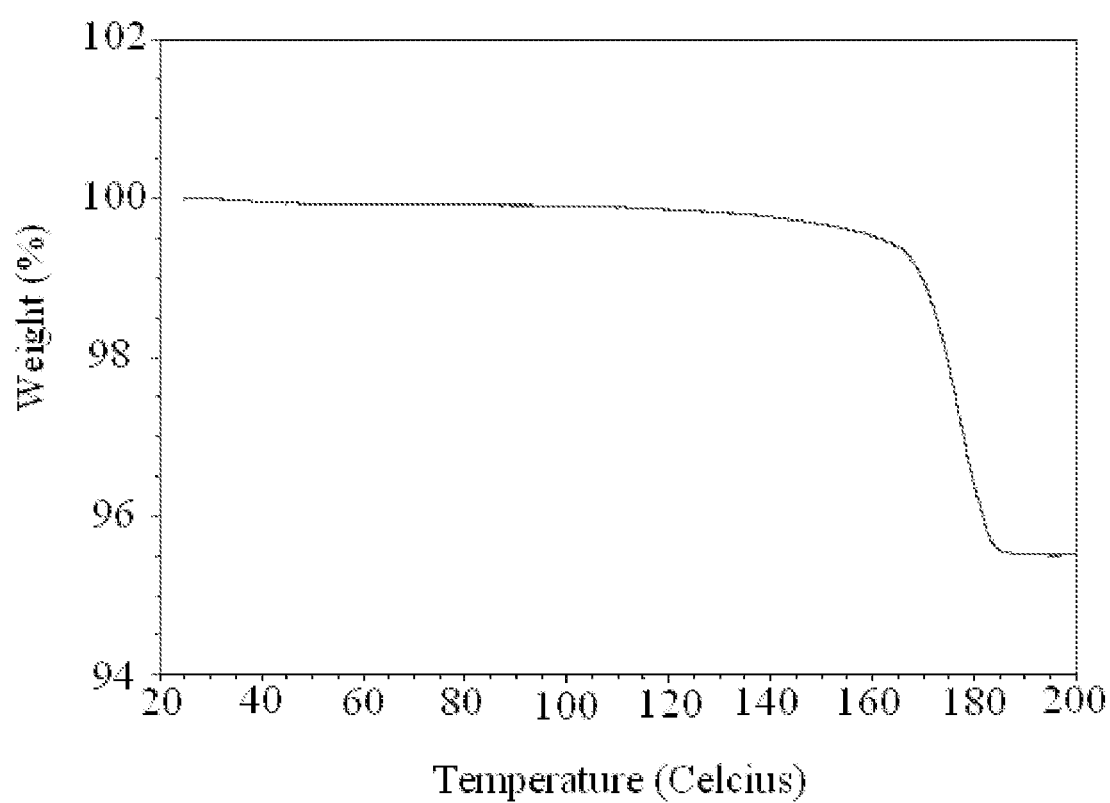

FIG. 16 is a Thermogravimetric analysis (TGA) plot of Compound 1 Form II, Acetone Solvate.

Figure 17:
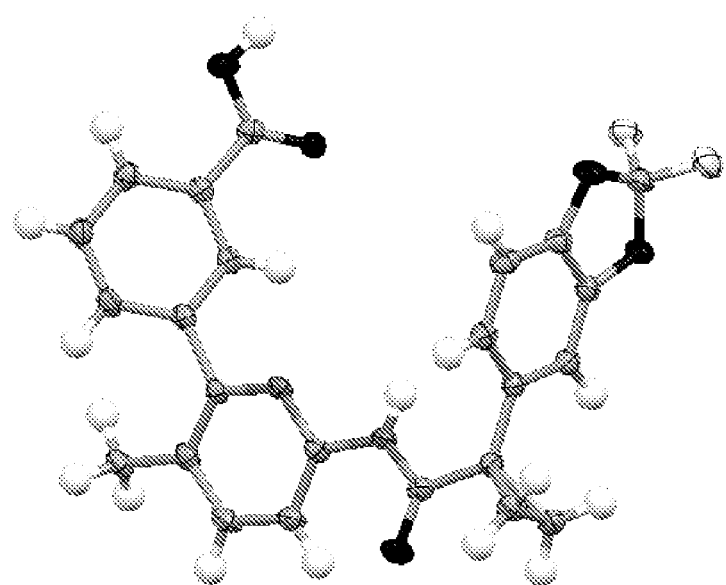

FIG. 17 is a conformational image of Compound 1 Form II, Acetone Solvate based on single crystal X-ray analysis.

Figure 18:
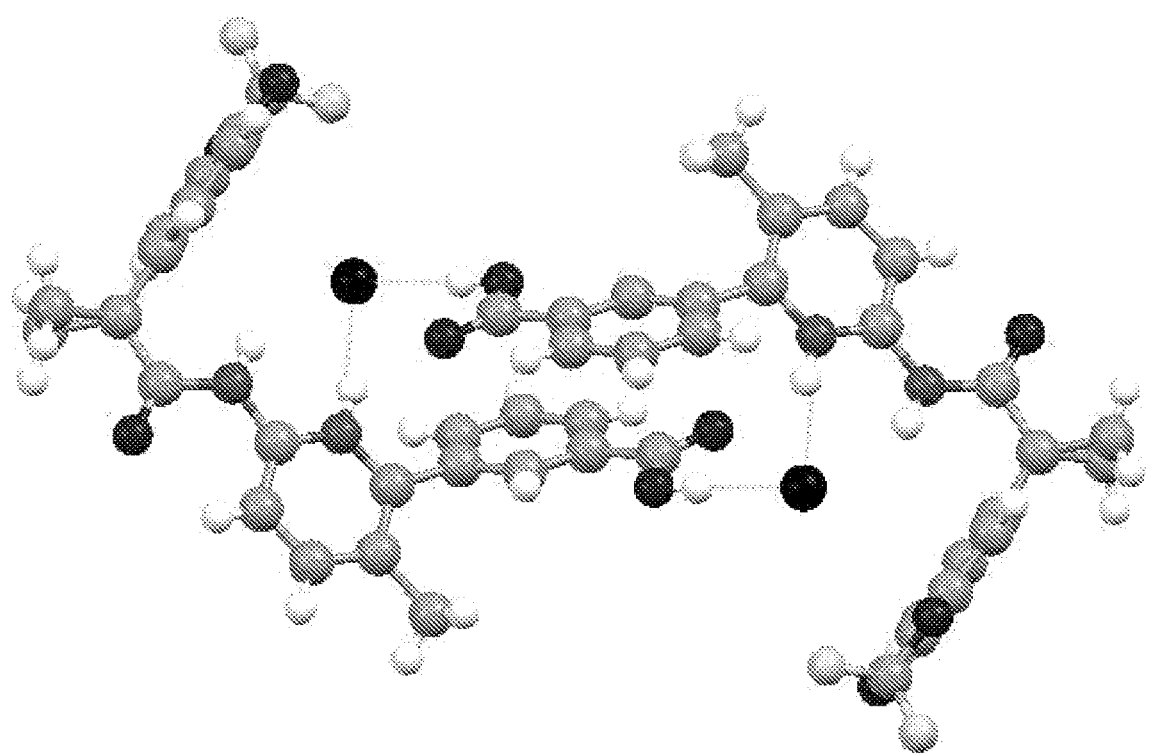

FIG. 18 is a conformational image of the dimer of Compound 1 HCl Salt Form A.

Figure 19:
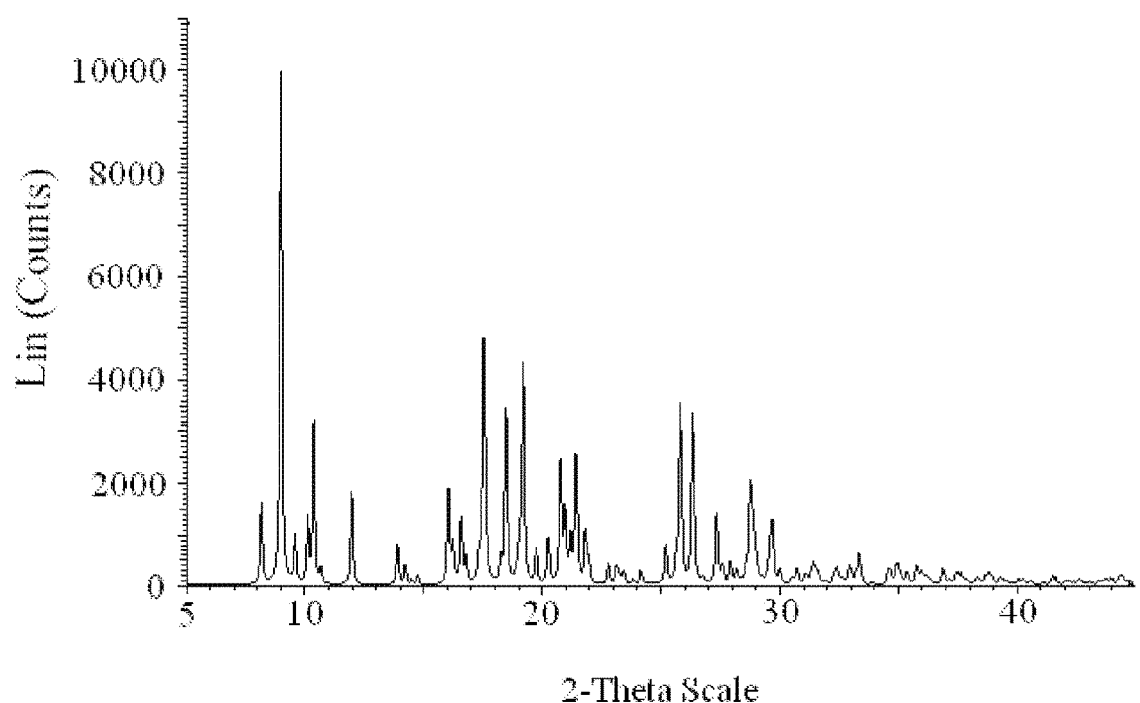

FIG. 19 is an X-ray diffraction pattern of Compound 1 HCl Salt Form A calculated from the crystal structure.

Figure 20:
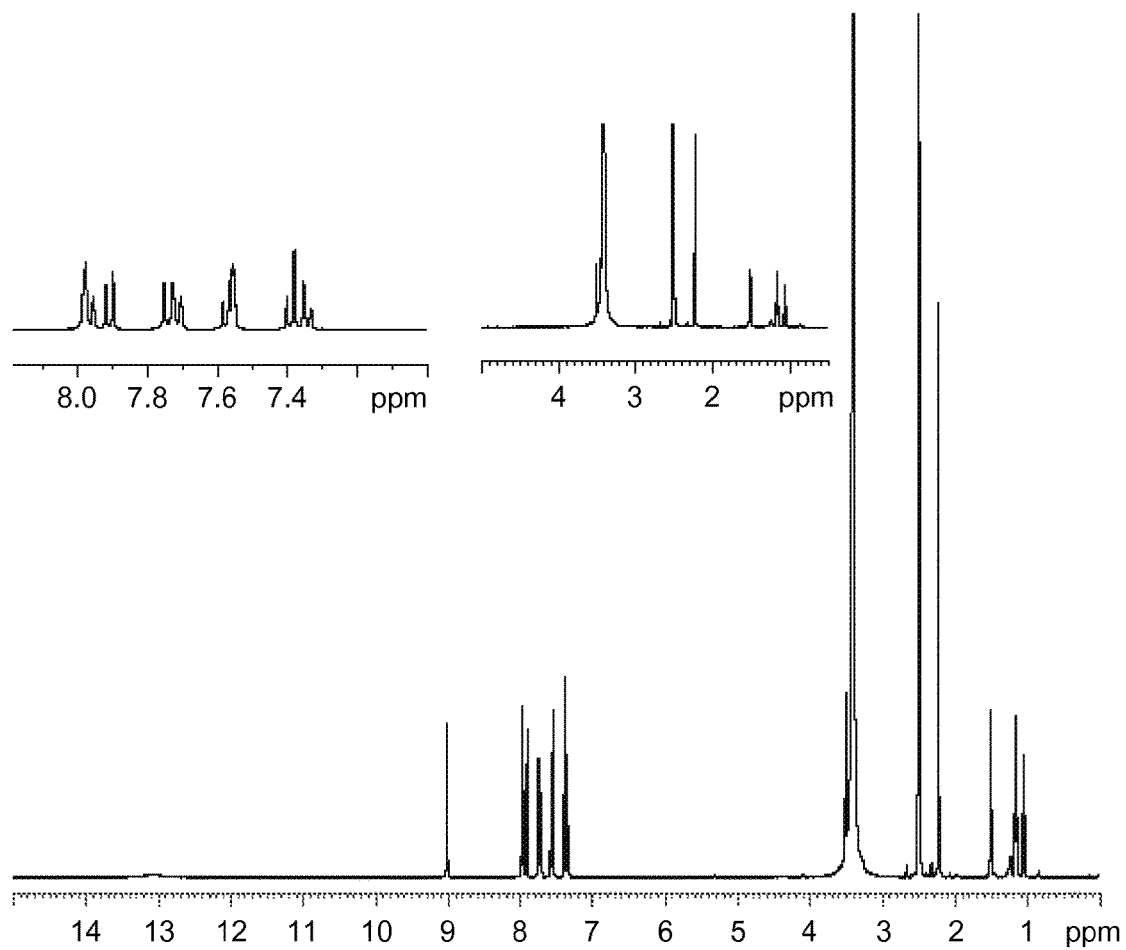

FIG. 20 is an $^1$HNMR spectrum of Compound 1.

Figure 21:
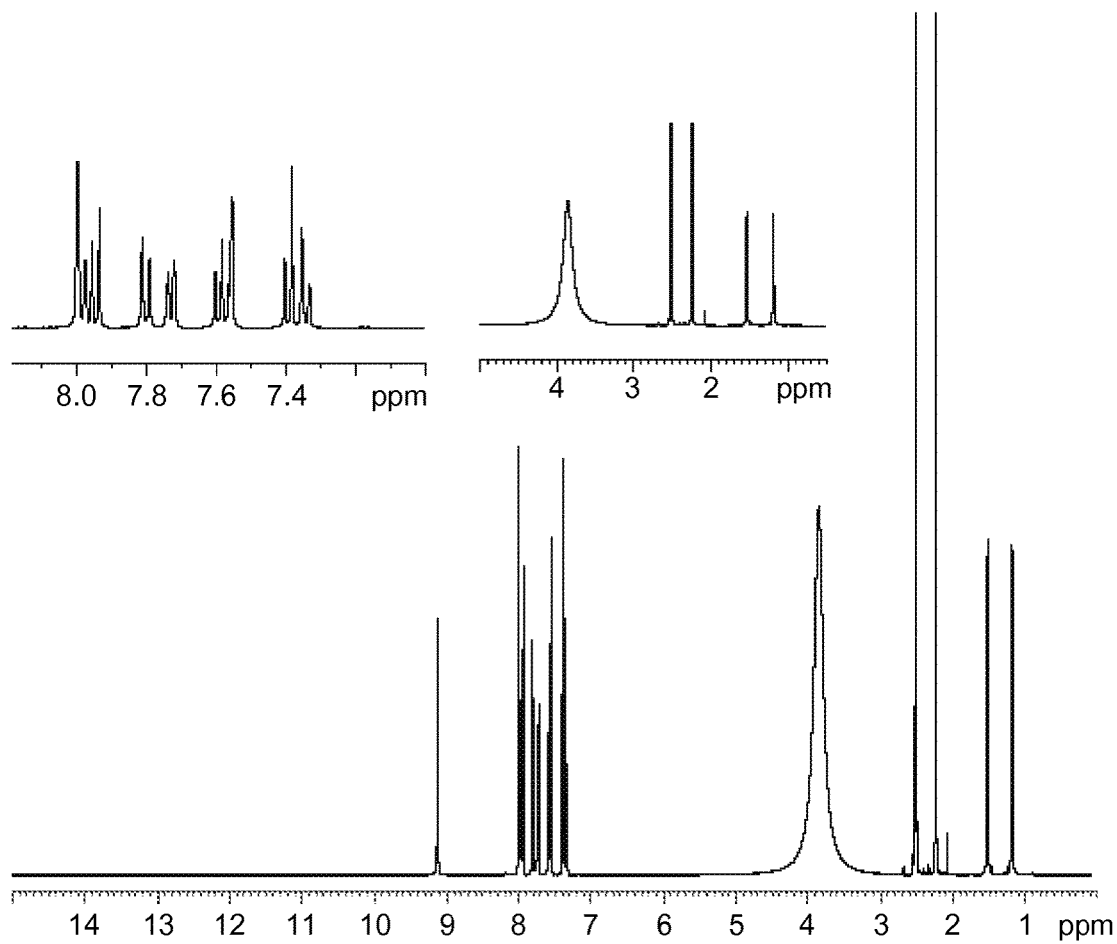

FIG. 21 is an $^1$HNMR spectrum of Compound 1 HCl salt.

Figure 22:
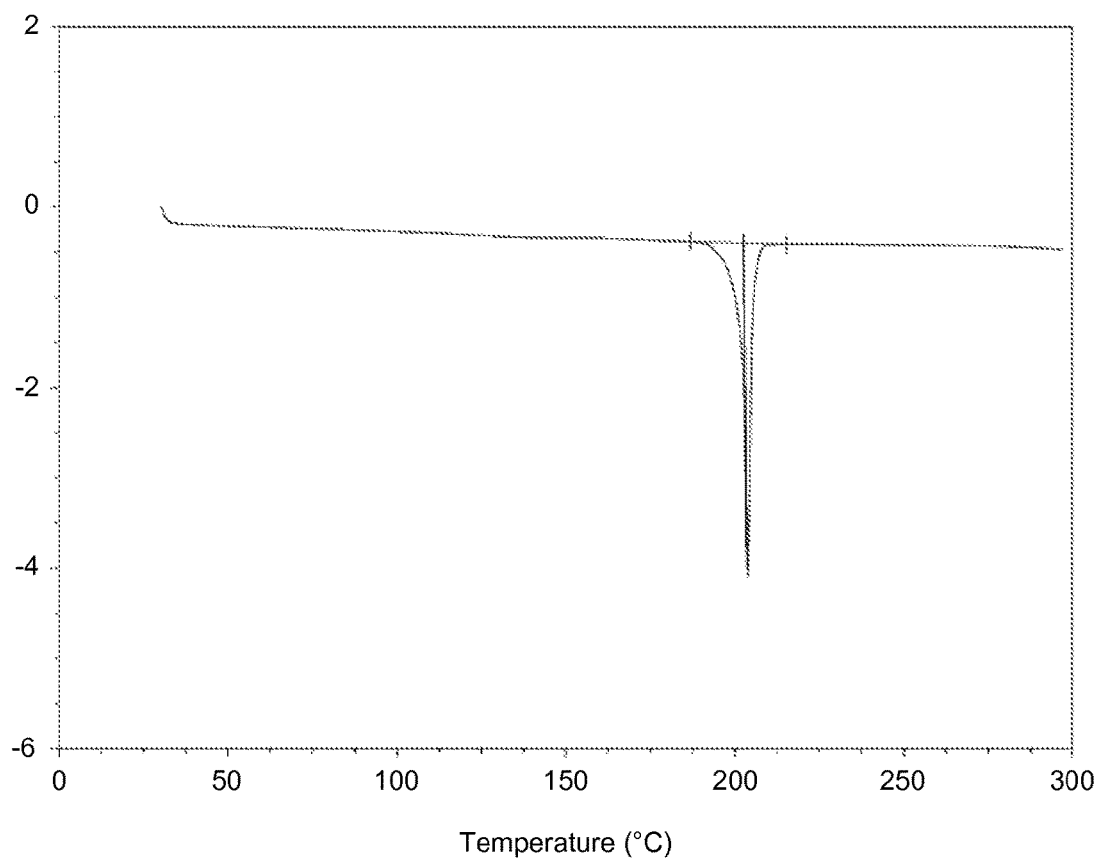

FIG. 22 is a differential scanning calorimetry (DSC) trace of Compound 1 Form I.

Figure 23:
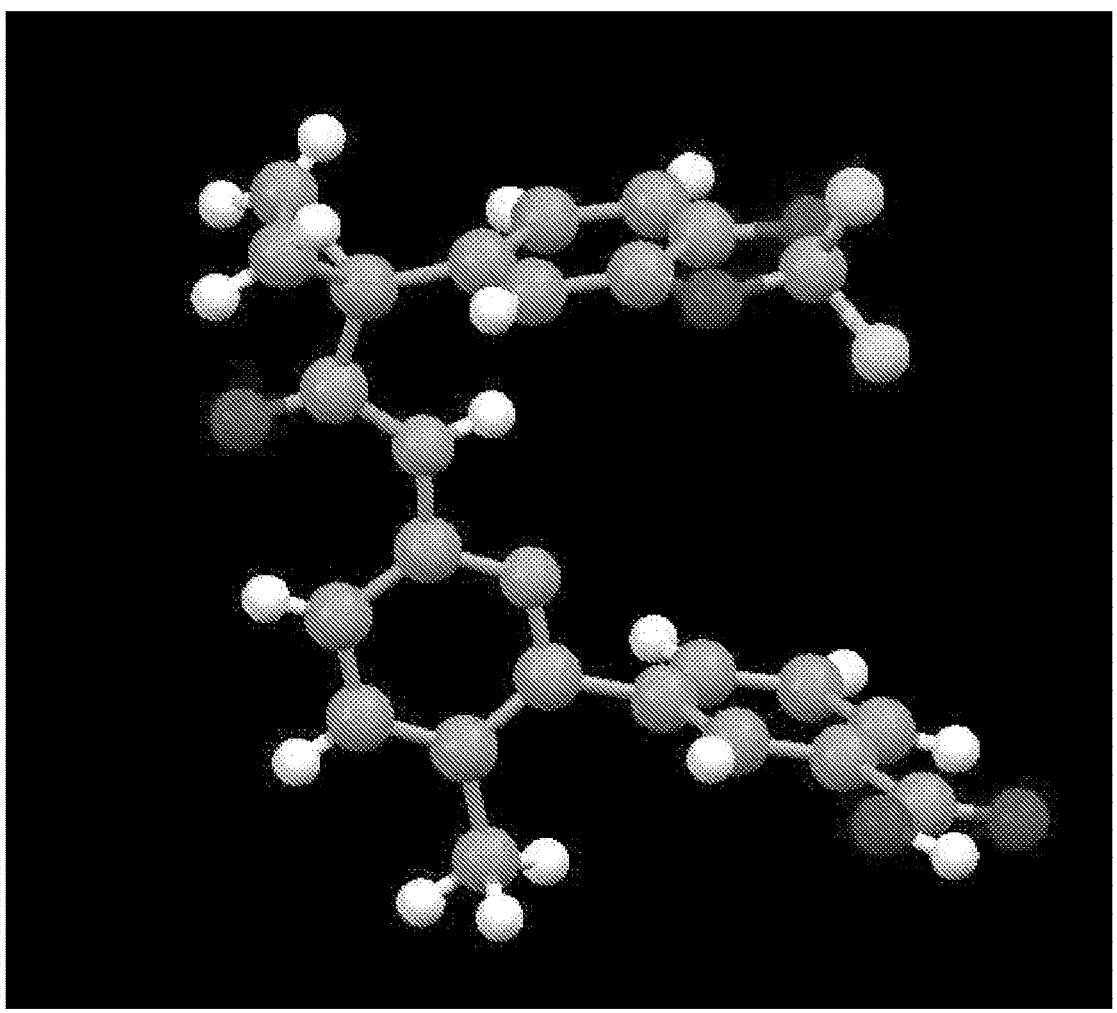

FIG. 23 is a conformational picture of Compound 1 Form I based on single crystal X-ray analysis.

Figure 24:
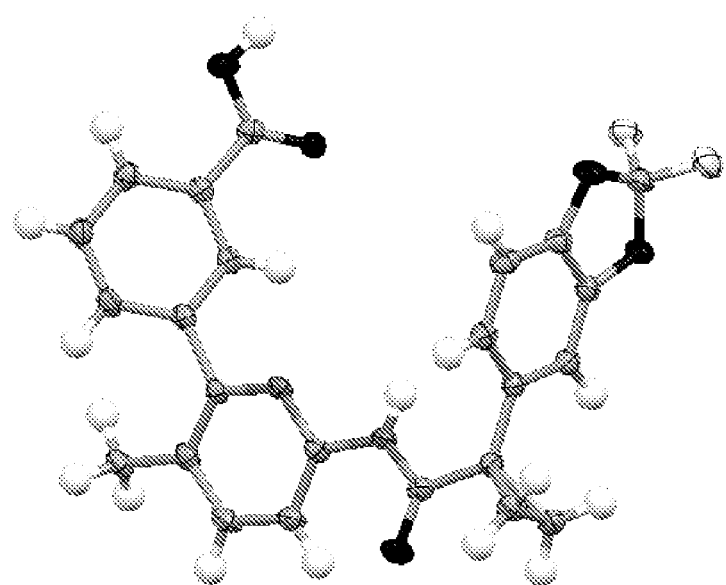

FIG. 24 is a conformational image of Compound 1 Form II, Acetone Solvate, based on single crystal X-ray analysis.

Figure 25:
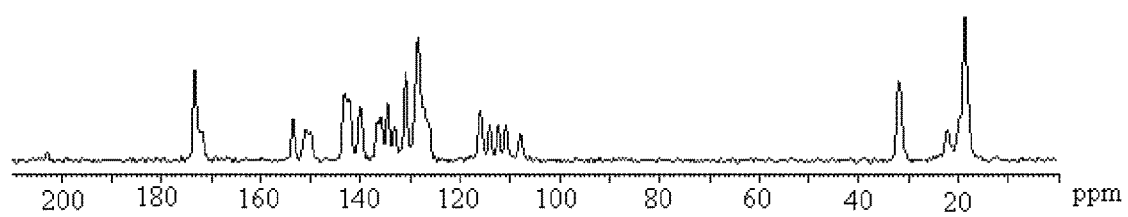

FIG. 25 is a solid state $^{13}$C NMR spectrum (15.0 kHz spinning) of Compound 1 Form II, Acetone Solvate.

Figure 26:
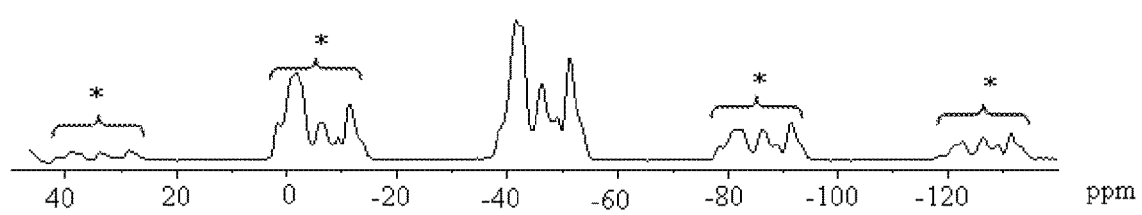

FIG. 26 is a solid state $^{19}$F NMR spectrum (12.5 kHz spinning) of Compound 1 Form II, Acetone Solvate.

Figure 27:
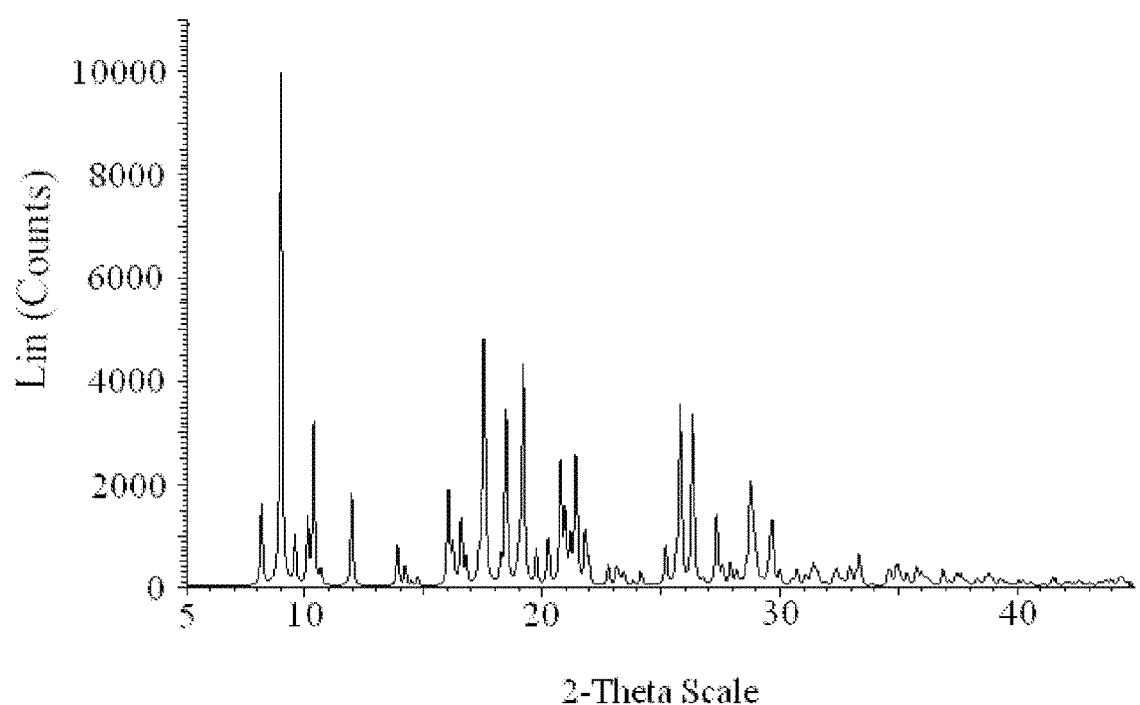

FIG. 27 is an X-ray diffraction pattern of Compound 1 HCl Salt Form A calculated from the crystal structure.

DETAILED DESCRIPTION

Definitions

As used herein, the term "active pharmaceutical ingredient" or "API" refers to a biologically active compound. Exemplary APIs include 3-(6-(1-(2,2-difluorobenzo[d][1,3]dioxol-5-yl) cyclopropanecarboxamido)-3-methylpyridin-2-yl)benzoic acid (Compound 1).

The terms "solid form", "solid forms" and related terms, when used herein to refer to 3-(6-(1-(2,2-difluorobenzo[d][1,3]dioxol-5-yl) cyclopropanecarboxamido)-3-methylpyridin-2-yl) benzoic acid (Compound 1), refer to a solid form e.g. crystals and the like, comprising Compound 1 which is not predominantly in a liquid or a gaseous state.

As used herein, the term "substantially amorphous" refers to a solid material having little or no long range order in the position of its molecules. For example, substantially amorphous materials have less than about 15% crystallinity (e.g., less than about 10% crystallinity or less than about 5% crystallinity). It is also noted that the term 'substantially amorphous' includes the descriptor, 'amorphous', which refers to materials having no (0%) crystallinity.

As used herein, the term "substantially crystalline" (as in the phrase substantially crystalline Compound 1 Form I, Compound 1 Form II, or Compound 1 HCl Salt Form A) refers to a solid material having predominantly long range order in the position of its molecules. For example, substantially crystalline materials have more than about 85% crystallinity (e.g., more than about 90% crystallinity or more than about 95% crystallinity). It is also noted that the term 'substantially crystalline' includes the descriptor, 'crystalline', which refers to materials having 100% crystallinity.

The term "crystalline" and related terms used herein, when used to describe a substance, component, product, or form, means that the substance, component or product is substantially crystalline as determined by X-ray diffraction. (See, e.g., Remington: The Science and Practice of Pharmacy, 21st Ed., Lippincott Williams & Wilkins, Baltimore, Md. (2003); The United States Pharmacopeia, 23$^{rd}$ ed., 1843-1844 (1995)).

As used herein, the term "composition" generally refers to a composition of two or more components, usually one or more drugs (e.g., one drug (e.g., Compound 1 Form I, Compound 1 Form II, or Compound 1 HCl Salt Form A)) and one or more pharmaceutical excipients.

As used herein, the term "solid dosage form" generally refers to a pharmaceutical composition, which when used in an oral mode of administration include capsules, tablets, pills, powders and granules. In such solid dosage forms, the active compound is mixed with at least one inert, pharmaceutically acceptable excipient or carrier.

As used herein, an "excipient" includes functional and non-functional ingredients in a pharmaceutical composition.

As used herein, a "disintegrant" is an excipient that hydrates a pharmaceutical composition and aids in tablet dispersion. As used herein, a "diluent" or "filler" is an excipient that adds bulkiness to a pharmaceutical composition.

As used herein, a "surfactant" is an excipient that imparts pharmaceutical compositions with enhanced solubility and/or wetability.

As used herein, a "binder" is an excipient that imparts a pharmaceutical composition with enhanced cohesion or tensile strength (e.g., hardness).

As used herein, a "glidant" is an excipient that imparts a pharmaceutical compositions with enhanced flow properties.

As used herein, a "colorant" is an excipient that imparts a pharmaceutical composition with a desired color. Examples of colorants include commercially available pigments such as FD&C Blue #1 Aluminum Lake, FD&C Blue #2, other FD&C Blue colors, titanium dioxide, iron oxide, and/or combinations thereof. In one embodiment, the pharmaceutical composition provided by the invention is purple.

As used herein, a "lubricant" is an excipient that is added to pharmaceutical compositions that are pressed into tablets.

The lubricant aids in compaction of granules into tablets and ejection of a tablet of a pharmaceutical composition from a die press.

As used herein, "cubic centimeter" and "cc" are used interchangeably to represent a unit of volume. Note that 1 cc=1 mL.

As used herein, "kiloPond" and "kP" are used interchangeably and refer to the measure of force where a kP=approximately 9.8 Newtons.

As used herein, "friability" refers to the property of a tablet to remain intact and withhold its form despite an external force of pressure. Friability can be quantified using the mathematical expression presented in equation 1:

$$\% \ friabiliy = 100 \times \frac{(W_0 - W_f)}{W_0} \qquad (1)$$

wherein $W_0$ is the original weight of the tablet and $W_f$ is the final weight of the tablet after it is put through the friabilator. Friability is measured using a standard USP testing apparatus that tumbles experimental tablets for 100 or 400 revolutions. Some tablets of the invention have a friability of less than 5.0%. In another embodiment, the friability is less than 2.0%. In another embodiment, the target friability is less than 1.0% after 400 revolutions.

As used herein, "mean particle diameter" is the average particle diameter as measured using techniques such as laser light scattering, image analysis, or sieve analysis. In one embodiment, the granules used to prepare the pharmaceutical compositions provided by the invention have a mean particle diameter of less than 1.0 mm.

As used herein, "bulk density" is the mass of particles of material divided by the total volume the particles occupy. The total volume includes particle volume, inter-particle void volume and internal pore volume. Bulk density is not an intrinsic property of a material; it can change depending on how the material is processed. In one embodiment, the granules used to prepare the pharmaceutical compositions provided by the invention have a bulk density of about 0.5-0.7 g/cc.

An effective amount or "therapeutically effective amount" of a drug compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

As used herein, and unless otherwise specified, the terms "therapeutically effective amount" and "effective amount" of a compound mean an amount sufficient to provide a therapeutic benefit in the treatment or management of a disease or disorder, or to delay or minimize one or more symptoms associated with the disease or disorder. A "therapeutically effective amount" and "effective amount" of a compound mean an amount of therapeutic agent, alone or in combination with one or more other agent(s), which provides a therapeutic benefit in the treatment or management of the disease or disorder. The terms "therapeutically effective amount" and "effective amount" can encompass an amount that improves overall therapy, reduces or avoids symptoms or causes of disease or disorder, or enhances the therapeutic efficacy of another therapeutic agent.

"Substantially pure" as used in the phrase "substantially pure Compound 1 Form I, Compound 1 Form II, or Compound 1 HCl Salt Form A," means greater than about 90% purity. In another embodiment, substantially pure refers to greater than about 95% purity. In another embodiment, substantially pure refers to greater than about 98% purity. In another embodiment, substantially pure refers to greater than about 99% purity.

With respect to Compound 1 (e.g., Compound 1 Form I, Compound 1 Form II, Compound 1 HCl Salt Form A), the terms "about" and "approximately", when used in connection with doses, amounts, or weight percent of ingredients of a composition or a dosage form, mean a dose, amount, or weight percent that is recognized by one of ordinary skill in the art to provide a pharmacological effect equivalent to that obtained from the specified dose, amount, or weight percent. Specifically the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

Unless otherwise specified, the term "Compound 1" includes, but is not limited to, the solid forms of Compound 1 as described herein, e.g. Compound 1 Form I, Compound 1 Form II, or Compound 1 HCl Salt Form A, as well as combinations thereof.

Pharmaceutical Compositions

The invention provides pharmaceutical compositions, pharmaceutical formulations and solid dosage forms comprising Compound 1 which may be in substantially crystalline form. In some embodiments, Compound 1 is in crystalline Form I (Compound 1 Form I). In some embodiments, Compound 1 is in crystalline Form II (Compound 1 Form II). In some embodiments, Compound 1 is in crystalline HCl salt form (Compound 1 HCl Salt Form A). In some embodiments of this aspect, the amount of Compound 1 that is present in the pharmaceutical composition is 25 mg, 50 mg, 75 mg, 100 mg, 125 mg, 150 mg, 200 mg, 250 mg, or 400 mg. In some embodiments of this aspect, weight/weight relative percent of Compound 1 that is present in the pharmaceutical composition is from 10 to 75 percent. In these and other embodiments, 3-(6-(1-(2,2-difluorobenzo[d][1,3]dioxol-5-yl) cyclopropanecarboxamido)-3-methylpyridin-2-yl)benzoic acid is present as substantially pure Compound 1. "Substantially pure" means greater than ninety percent pure; preferably greater than 95 percent pure; more preferably greater than 99.5 percent pure (i.e., not mixed with other crystalline forms of Compound 1).

Thus in one aspect, the invention provides a pharmaceutical composition comprising:
a. Compound 1;
b. a filler;
c. a disintegrant;
d. a surfactant;
e. a diluent;
f. a lubricant; and
g. and at least one of a glidant and a binder.

In one embodiment of this aspect, the pharmaceutical composition comprises 25 mg of Compound 1. In another embodiment of this aspect, the pharmaceutical composition comprises 50 mg of Compound 1. In another embodiment of this aspect, the pharmaceutical composition comprises 100 mg of Compound 1. In another embodiment of this aspect, the pharmaceutical composition comprises 125 mg of Compound 1. In another embodiment of this aspect, the pharmaceutical composition comprises 150 mg of Compound 1. In another embodiment of this aspect, the pharmaceutical composition comprises 200 mg of Compound 1. In another embodiment of this aspect, the pharmaceutical composition comprises 250 mg of Compound 1. In another embodiment of this aspect, the pharmaceutical composition comprises 400 mg of Compound 1.

In some embodiments, the pharmaceutical compositions comprises Compound 1, wherein Compound 1 is present in an amount of at least 15 wt % (e.g., at least 20 wt %, at least 30 wt %, at least 40 wt %, at least 50 wt %, or at least 60 wt %) by weight of the composition.

In some embodiments, the pharmaceutical composition comprises Compound 1, a filler, a diluent, a disintegrant, a surfactant, a glidant, and a lubricant. In this embodiment, the composition comprises from about 20 wt % to about 50 wt % (e.g., about 25-35 wt %) of Compound 1 by weight of the composition, and more typically, from 25 wt % to about 45 wt % (e.g., about 28-32 wt %) of Compound 1 by weight of the composition.

In some embodiments, the pharmaceutical composition comprises Compound 1, a filler, a diluent, a disintegrant, a surfactant, a binder, and a lubricant. In this embodiment, the composition comprises from about 30 wt % to about 60 wt % (e.g., about 40-55 wt %) of Compound 1 by weight of the composition, and more typically from 35 wt % to about 70 wt % (e.g., about 45-55 wt %) of Compound 1 by weight of the composition.

The concentration of Compound 1 in the composition depends on several factors such as the amount of pharmaceutical composition needed to provide a desired amount of Compound 1 and the desired dissolution profile of the pharmaceutical composition.

In another embodiment, the pharmaceutical composition comprises Compound 1, in which Compound 1 in its solid form has a mean particle diameter, measured by light scattering (e.g., using a Malvern Mastersizer available from Malvern Instruments in England) of 0.1 microns to 10 microns. In another embodiment, the particle size of Compound 1 is 1 micron to 5 microns. In another embodiment, Compound 1 has a particle size D50 of 2.0 microns.

As indicated, in addition to Compound 1, in some embodiments of the invention, the pharmaceutical compositions which are oral formulations also comprise one or more excipients such as fillers, disintegrants, surfactants, diluents, binders, glidants, lubricants, colorants, or fragrances and any combination thereof.

Fillers suitable for the invention are compatible with the ingredients of the pharmaceutical composition, i.e., they do not substantially reduce the solubility, the hardness, the chemical stability, the physical stability, or the biological activity of the pharmaceutical composition. Exemplary fillers include: celluloses, modified celluloses, (e.g. sodium carboxymethyl cellulose, ethyl cellulose hydroxymethyl cellulose, hydroxypropylcellulose), cellulose acetate, microcrystalline cellulose, calcium phosphates, dibasic calcium phosphate, starches (e.g. corn starch, potato starch), sugars (e.g., sorbitol) lactose, sucrose, or the like), or any combination thereof.

Thus, in one embodiment, the pharmaceutical composition comprises at least one filler in an amount of at least 5 wt % (e.g., at least about 20 wt %, at least about 30 wt %, or at least about 40 wt %) by weight of the composition. For example, the pharmaceutical composition comprises from about 10 wt % to about 60 wt % (e.g., from about 20 wt % to about 55 wt %, from about 25 wt % to about 50 wt %, or from about 27 wt % to about 45 wt %) of filler, by weight of the composition. In another example, the pharmaceutical composition comprises at least about 20 wt % (e.g., at least 30 wt % or at least 40 wt %) of microcrystalline cellulose, for example MCC Avicel PH102, by weight of the composition. In yet another example, the pharmaceutical composition comprises from about 10 wt % to about 60 wt % (e.g., from about 20 wt % to about 55 wt % or from about 25 wt % to about 45 wt %) of microcellulose, by weight of the composition.

Disintegrants suitable for the invention enhance the dispersal of the pharmaceutical composition and are compatible with the ingredients of the pharmaceutical composition, i.e., they do not substantially reduce the chemical stability, the physical stability, the hardness, or the biological activity of the pharmaceutical composition. Exemplary disintegrants include croscarmellose sodium, sodium starch glycolate, or a combination thereof.

Thus, in one embodiment, the pharmaceutical composition comprises disintegrant in an amount of about 10 wt % or less (e.g., about 7 wt % or less, about 6 wt % or less, or about 5 wt % or less) by weight of the composition. For example, the pharmaceutical composition comprises from about 1 wt % to about 10 wt % (e.g., from about 1.5 wt % to about 7.5 wt % or from about 2.5 wt % to about 6 wt %) of disintegrant, by weight of the composition. In another example, the pharmaceutical composition comprises about 10 wt % or less (e.g., 7 wt % or less, 6 wt % or less, or 5 wt % or less) of croscarmellose sodium, by weight of the composition. In yet another example, the pharmaceutical composition comprises from about 1 wt % to about 10 wt % (e.g., from about 1.5 wt % to about 7.5 wt % or from about 2.5 wt % to about 6 wt %) of croscarmellose sodium, by weight of the composition. In some examples, the pharmaceutical composition comprises from about 0.1% to about 10 wt % (e.g., from about 0.5 wt % to about 7.5 wt % or from about 1.5 wt % to about 6 wt %) of disintegrant, by weight of the composition. In still other examples, the pharmaceutical composition comprises from about 0.5% to about 10 wt % (e.g., from about 1.5 wt % to about 7.5 wt % or from about 2.5 wt % to about 6 wt %) of disintegrant, by weight of the composition.

Surfactants suitable for the invention enhance the wettability of the pharmaceutical composition and are compatible with the ingredients of the pharmaceutical composition, i.e., they do not substantially reduce the chemical stability, the physical stability, the hardness, or the biological activity of the pharmaceutical composition. Exemplary surfactants include sodium lauryl sulfate (SLS), sodium stearyl fumarate (SSF), polyoxyethylene 20 sorbitan mono-oleate (e.g., Tween™), any combination thereof, or the like.

Thus, in one embodiment, the pharmaceutical composition comprises a surfactant in an amount of about 10 wt % or less (e.g., about 5 wt % or less, about 2 wt % or less, about 1 wt % or less, about 0.8 wt % or less, or about 0.6 wt % or less) by weight of the composition. For example, the pharmaceutical composition includes from about 10 wt % to about 0.1 wt % (e.g., from about 5 wt % to about 0.2 wt % or from about 2 wt % to about 0.3 wt %) of surfactant, by weight of the composition. In another example, the pharmaceutical composition comprises 10 wt % or less (e.g., about 5 wt % or less, about 2 wt % or less, about 1 wt % or less, about 0.8 wt % or less, or about 0.6 wt % or less) of sodium lauryl sulfate, by weight of the composition. In yet another example, the pharmaceutical composition comprises from about 10 wt % to about 0.1 wt % (e.g., from about 5 wt % to about 0.2 wt % or from about 2 wt % to about 0.3 wt %) of sodium lauryl sulfate, by weight of the composition.

Binders suitable for the invention enhance the tablet strength of the pharmaceutical composition and are compatible with the ingredients of the pharmaceutical composition, i.e., they do not substantially reduce the chemical stability, the physical stability, or the biological activity of the pharmaceutical composition. Exemplary binders include polyvinylpyrrolidone, dibasic calcium phosphate, sucrose, corn (maize) starch, modified cellulose (e.g., hydroxymethyl cellulose), or any combination thereof.

Thus, in one embodiment, the pharmaceutical composition comprises a binder in an amount of at least about 0.1 wt % (e.g., at least about 1 wt %, at least about 3 wt %, at least about 4 wt %, or at least about 5 wt %) by weight of the composition. For example, the pharmaceutical composition comprises from about 0.1 wt % to about 10 wt % (e.g., from about 1 wt % to about 10 wt % or from about 2 wt % to about 7 wt %) of binder, by weight of the composition. In another example, the pharmaceutical composition comprises at least about 0.1 wt % (e.g., at least about 1 wt %, at least about 2 wt %, at least about 3 wt %, or at least about 4 wt %) of polyvinylpyrrolidone, by weight of the composition. In yet another example, the pharmaceutical composition comprises a glidant in an amount ranging from about 0.1 wt % to about 10 wt % (e.g., from about 1 wt % to about 8 wt % or from about 2 wt % to about 5 wt %) of polyvinylpyrrolidone, by weight of the composition.

Diluents suitable for the invention may add necessary bulk to a formulation to prepare tablets of the desired size and are generally compatible with the ingredients of the pharmaceutical composition, i.e., they do not substantially reduce the solubility, the hardness, the chemical stability, the physical stability, or the biological activity of the pharmaceutical composition. Exemplary diluents include: sugars, for example, confectioner's sugar, compressible sugar, dextrates, dextrin, dextrose, lactose, mannitol, sorbitol, cellulose, and modified celluloses, for example, powdered cellulose, talc, calcium phosphate, starch, or any combination thereof.

Thus, in one embodiment, the pharmaceutical composition comprises a diluent in an amount of 40 wt % or less (e.g., 35 wt % or less, 30 wt % or less, or 25 wt % or less, or 20 wt % or less, or 15 wt % or less, or 10 wt % or less) by weight of the composition. For example, the pharmaceutical composition comprises from about 40 wt % to about 1 wt % (e.g., from about 35 wt % to about 5 wt % or from about 30 wt % to about 7 wt %, from about 25 wt % to about 10 wt %, from about 20 wt % to about 15 wt %) of diluent, by weight of the composition. In another example, the pharmaceutical composition comprises 40 wt % or less (e.g., 35 wt % or less, 25 wt % or less, or 15 wt % or less) of mannitol, by weight of the composition. In yet another example, the pharmaceutical composition comprises from about 35 wt % to about 1 wt % (e.g., from about 30 wt % to about 5 wt % or from about 25 wt % to about 10 wt %) of mannitol, by weight of the composition.

Glidants suitable for the invention enhance the flow properties of the pharmaceutical composition and are compatible with the ingredients of the pharmaceutical composition, i.e., they do not substantially reduce the solubility, the hardness, the chemical stability, the physical stability, or the biological activity of the pharmaceutical composition. Exemplary glidants include colloidal silicon dioxide, talc, or a combination thereof.

Thus, in one embodiment, the pharmaceutical composition comprises a glidant in an amount of 2 wt % or less (e.g., 1.75 wt %, 1.25 wt % or less, or 1.00 wt % or less) by weight of the composition. For example, the pharmaceutical composition comprises from about 2 wt % to about 0.05 wt % (e.g., from about 1.5 wt % to about 0.07 wt % or from about 1.0 wt % to about 0.09 wt %) of glidant, by weight of the composition. In another example, the pharmaceutical composition comprises 2 wt % or less (e.g., 1.75 wt %, 1.25 wt % or less, or 1.00 wt % or less) of colloidal silicon dioxide, by weight of the composition. In yet another example, the pharmaceutical composition comprises from about 2 wt % to about 0.05 wt % (e.g., from about 1.5 wt % to about 0.07 wt % or from about 1.0 wt % to about 0.09 wt %) of colloidal silicon dioxide, by weight of the composition.

In some embodiments, the pharmaceutical composition can include an oral solid pharmaceutical dosage form which can comprise a lubricant that can prevent adhesion of a granulate-bead admixture to a surface (e.g., a surface of a mixing bowl, a compression die and/or punch). A lubricant can also reduce interparticle friction within the granulate and improve the compression and ejection of compressed pharmaceutical compositions from a die press. The lubricant is also compatible with the ingredients of the pharmaceutical composition, i.e., they do not substantially reduce the solubility, the hardness, or the biological activity of the pharmaceutical composition. Exemplary lubricants include magnesium stearate, calcium stearate, zinc stearate, sodium stearate, stearic acid, aluminum stearate, leucine, glyceryl behenate, hydrogenated vegetable oil or any combination thereof. In one embodiment, the pharmaceutical composition comprises a lubricant in an amount of 5 wt % or less (e.g., 4.75 wt %, 4.0 wt % or less, or 3.00 wt % or less, or 2.0 wt % or less) by weight of the composition. For example, the pharmaceutical composition comprises from about 5 wt % to about 0.10 wt % (e.g., from about 4.5 wt % to about 0.5 wt % or from about 3 wt % to about 1 wt %) of lubricant, by weight of the composition. In another example, the pharmaceutical composition comprises 5 wt % or less (e.g., 4.0 wt % or less, 3.0 wt % or less, or 2.0 wt % or less, or 1.0 wt % or less) of magnesium stearate, by weight of the composition. In yet another example, the pharmaceutical composition comprises from about 5 wt % to about 0.10 wt % (e.g., from about 4.5 wt % to about 0.15 wt % or from about 3.0 wt % to about 0.50 wt %) of magnesium stearate, by weight of the composition.

Pharmaceutical compositions of the invention can optionally comprise one or more colorants, flavors, and/or fragrances to enhance the visual appeal, taste, and/or scent of the composition. Suitable colorants, flavors, or fragrances are compatible with the ingredients of the pharmaceutical composition, i.e., they do not substantially reduce the solubility, the chemical stability, the physical stability, the hardness, or the biological activity of the pharmaceutical composition. In one embodiment, the pharmaceutical composition comprises a colorant, a flavor, and/or a fragrance. In one embodiment, the pharmaceutical compositions provided by the invention are purple.

In some embodiments, the pharmaceutical composition includes or can be made into tablets and the tablets can be coated with a colorant and optionally labeled with a logo, other image and/or text using a suitable ink. In still other embodiments, the pharmaceutical composition includes or can be made into tablets and the tablets can be coated with a colorant, waxed, and optionally labeled with a logo, other image and/or text using a suitable ink. Suitable colorants and inks are compatible with the ingredients of the pharmaceutical composition, i.e., they do not substantially reduce the solubility, the chemical stability, the physical stability, the hardness, or the biological activity of the pharmaceutical composition. The suitable colorants and inks can be any color and are water based or solvent based. In one embodiment, tablets made from the pharmaceutical composition are coated with a colorant and then labeled with a logo, other image, and/or text using a suitable ink. For example, tablets comprising pharmaceutical composition as described herein can be coated with about 3 wt % (e.g., less than about 6 wt % or less than about 4 wt %) of film coating comprising a colorant. The colored tablets can be labeled with a logo and text indicating the strength of the active ingredient in the tablet using a suitable ink. In another example, tablets comprising pharmaceutical composition as described herein can be coated with about 3 wt % (e.g., less than about 6 wt % or less than about 4 wt %) of a film coating comprising a colorant.

In another embodiment, tablets made from the pharmaceutical composition are coated with a colorant, waxed, and then labeled with a logo, other image, and/or text using a suitable ink. For example, tablets comprising pharmaceutical composition as described herein can be coated with about 3 wt % (e.g., less than about 6 wt % or less than about 4 wt %) of film coating comprising a colorant. The colored tablets can be waxed with Carnauba wax powder weighed out in the amount of about 0.01% w/w of the starting tablet core weight. The waxed tablets can be labeled with a logo and text indicating the strength of the active ingredient in the tablet using a suitable ink. In another example, tablets comprising pharmaceutical composition as described herein can be coated with about 3 wt % (e.g., less than about 6 wt % or less than about 4 wt %) of a film coating comprising a colorant. The colored tablets can be waxed with Carnauba wax powder weighed out in the amount of about 0.01% w/w of the starting tablet core weight. The waxed tablets can be labeled with a logo and text indicating the strength of the active ingredient in the tablet using a pharmaceutical grade ink such as a black ink (e.g., Opacode® S-1-17823, a solvent based ink, commercially available from Colorcon, Inc. of West Point, Pa.).

One exemplary pharmaceutical composition comprises from about 15 wt % to about 70 wt % (e.g., from about 15 wt % to about 60 wt %, from about 15 wt % to about 50 wt %, or from about 15 wt % to about 40 wt %, or from about 20 wt % to about 70 wt %, or from about 30 wt % to about 70 wt %, or from about 40 wt % to about 70 wt %, or from about 50 wt % to about 70 wt %) of Compound 1, by weight of the composition. The aforementioned compositions can also include one or more pharmaceutically acceptable excipients, for example, from about 20 wt % to about 50 wt % of a filler; from about 1 wt % to about 5 wt % of a disintegrant; from about 2 wt % to about 0.3 wt % of a surfactant; from about 0.1 wt % to about 5 wt % of a binder; from about 1 wt % to about 30 wt % of a diluent; from about 2 wt % to about 0.05 wt % of a glidant; and from about 5 wt % to about 0.1 wt % of a lubricant. Or, the pharmaceutical composition comprises a composition containing from about 15 wt % to about 70 wt % (e.g., from about 20 wt % to about 40 wt %, from about 25 wt % to about 60 wt %, or from about 30 wt % to about 55 wt %) of Compound 1, by weight of the composition; and one or more excipients, for example, from about 20 wt % to about 50 wt % of a filler; from about 1 wt % to about 5 wt % of a disintegrant; from about 2 wt % to about 0.3 wt % of a surfactant; from about 0.1 wt % to about 5 wt % of a binder; from about 1 wt % to about 30 wt % of a diluent; from about 2 wt % to about 0.05 wt % of a glidant; and from about 5 wt % to about 0.1 wt % of a lubricant.

Another exemplary pharmaceutical composition comprises from about 15 wt % to about 70 wt % (e.g., from about 15 wt % to about 60 wt %, from about 15 wt % to about 50 wt %, or from about 15 wt % to about 40 wt % or from about 20 wt % to about 70 wt %, or from about 30 wt % to about 70 wt %, or from about 40 wt % to about 70 wt %, or from about 50 wt % to about 70 wt %) of Compound 1 by weight of the composition, and one or more excipients, for example, from about 20 wt % to about 50 wt % of a filler; from about 1 wt % to about 5 wt % of a disintegrant; from about 2 wt % to about 0.3 wt % of a surfactant; from about 0.1 wt % to about 5 wt % of a binder; from about 1 wt % to about 30 wt % of a diluent; from about 2 wt % to about 0.05 wt % of a glidant; and from about 2 wt % to about 0.1 wt % of a lubricant.

Another exemplary pharmaceutical composition comprises from about 15 wt % to about 70 wt % (e.g., from about 15 wt % to about 60 wt %, from about 15 wt % to about 50 wt %, or from about 15 wt % to about 40 wt % or from about 20 wt % to about 70 wt %, or from about 30 wt % to about 70 wt %, or from about 40 wt % to about 70 wt %, or from about 50 wt % to about 70 wt %) of Compound 1 by weight of the composition, and one or more excipients, for example, from about 20 wt % to about 50 wt % of a filler; from about 1 wt % to about 5 wt % of a disintegrant; from about 2 wt % to about 0.3 wt % of a surfactant; from about 0.1 wt % to about 5 wt % of a binder; from about 1 wt % to about 30 wt % of a diluent; from about 2 wt % to about 0.05 wt % of a glidant; and from about 2 wt % to about 0.1 wt % of a lubricant.

Another exemplary pharmaceutical composition comprises from about 15 wt % to about 70 wt % (e.g., from about 15 wt % to about 60 wt %, from about 15 wt % to about 50 wt %, or from about 15 wt % to about 40 wt % or from about 20 wt % to about 70 wt %, or from about 30 wt % to about 70 wt %, or from about 40 wt % to about 70 wt %, or from about 50 wt % to about 70 wt %) of Compound 1 and one or more excipients, for example, from about 20 wt % to about 50 wt % of a filler; from about 1 wt % to about 5 wt % of a disintegrant; from about 2 wt % to about 0.3 wt % of a surfactant; from about 0.1 wt % to about 5 wt % of a binder; from about 1 wt % to about 30 wt % of a diluent; from about 2 wt % to about 0.05 wt % of a glidant; and from about 2 wt % to about 0.1 wt % of a lubricant.

In one embodiment, the invention is a granular pharmaceutical composition comprising:

a. about 30 wt % of Compound 1 by weight of the composition;

b. about 42 wt % of microcrystalline cellulose by weight of the composition;

c. about 21 wt % of mannitol by weight of the composition;

d. about 3 wt % of sodium croscarmellose sodium by weight of the composition;

e. about 1 wt % of sodium lauryl sulfate by weight of the composition;

f. about 2 wt % of magnesium stearate by weight of the composition; and g. about 0.5 wt % of colloidal silica by weight of the composition.

Another granular composition formulated into an oral formulation of the invention comprises:
a. about 50 wt % of Compound 1;
b. about 30 wt % of microcrystalline cellulose by weight of the composition;
c. about 13 wt % of mannitol by weight of the composition;
d. about 2 wt % of sodium croscarmellose sodium by weight of the composition;
e. about 4 wt % of polyvinylpyrrolidone by weight of the composition; and
f. about 1 wt % of sodium lauryl sulfate by weight of the composition.

In one embodiment, a pharmaceutical oral formulation of the invention comprises:
a. about 30 wt % of a Compound 1 by weight of the composition;
b. about 42 wt % of microcrystalline cellulose by weight of the composition;
c. about 21 wt % of mannitol by weight of the composition;
d. about 3 wt % of sodium croscarmellose sodium by weight of the composition;
e. about 1 wt % of sodium lauryl sulfate by weight of the composition;
f. about 2.5 wt % of magnesium stearate by weight of the composition; and
g. about 0.5 wt % of colloidal silica by weight of the composition.

Another pharmaceutical oral formulation of the invention comprises:
a. about 50 wt % of a Compound 1 by weight of the composition;
b. about 30 wt % of microcrystalline cellulose by weight of the composition;
c. about 13 wt % of mannitol by weight of the composition;
d. about 4 wt % of sodium croscarmellose sodium by weight of the composition;
e. about 4 wt % of polyvinylpyrrolidone by weight of the composition
f. about 1 wt % of sodium lauryl sulfate by weight of the composition; and
g. about 0.5 wt % of magnesium stearate by weight of the composition.

Another pharmaceutical oral formulation of the invention comprises:
a. about 60 wt % of a Compound 1 by weight of the composition;
b. about 20 wt % of microcrystalline cellulose by weight of the composition;
c. about 13 wt % of mannitol by weight of the composition;
d. about 4 wt % of sodium croscarmellose sodium by weight of the composition;
e. about 4 wt % of polyvinylpyrrolidone by weight of the composition
f. about 1 wt % of sodium lauryl sulfate by weight of the composition; and
g. about 0.5 wt % of magnesium stearate by weight of the composition.

Another pharmaceutical oral formulation of the invention comprises:
a. about 150 to 250 mg of Compound 1;
b. about 40 to 50 mg of mannitol;
c. about 120 to 130 mg of microcrystalline cellulose;
d. about 10 to 20 mg of croscarmellose sodium;
e. about 10 to 20 mg of polyvinylpyrrolidone;
f. about 1 to 5 mg of sodium lauryl sulfate; and
g. about 1 to 5 mg of magnesium stearate.

Another pharmaceutical oral formulation of the invention comprises:
a. about 200 mg of Compound 1;
b. about 43 mg of mannitol;
c. about 123 mg of microcrystalline cellulose;
d. about 15 mg of croscarmellose sodium;
e. about 13 mg of polyvinylpyrrolidone;
f. about 3 mg of sodium lauryl sulfate; and
g. about 4 mg of magnesium stearate.

Another pharmaceutical oral formulation of the invention comprises:
a. about 200 mg of Compound 1;
b. about 45 mg of mannitol;
c. about 123 mg of microcrystalline cellulose;
d. about 15 mg of croscarmellose sodium;
e. about 10.4 mg of polyvinylpyrrolidone;
f. about 2.6 mg of sodium lauryl sulfate; and
g. about 4 mg of magnesium stearate.

Another pharmaceutical oral formulation of the invention comprises:
a. about 70 wt % of a Compound 1 by weight of the composition;
b. about 12 wt % of microcrystalline cellulose by weight of the composition;
c. about 11 wt % of mannitol by weight of the composition;
d. about 4 wt % of sodium croscarmellose sodium by weight of the composition;
e. about 4 wt % of polyvinylpyrrolidone by weight of the composition
f. about 1 wt % of sodium lauryl sulfate by weight of the composition; and
g. about 0.5 wt % of magnesium stearate by weight of the composition.

The pharmaceutical compositions of the invention can be processed into a tablet form, capsule form, pouch form, lozenge form, or other solid form that is suited for oral administration. Thus in some embodiments, the pharmaceutical compositions are in tablet form.

In still another pharmaceutical oral formulation of the invention, a shaped pharmaceutical tablet composition having an initial hardness of 5-21 kP±20 percent comprises: about 30 wt % of Compound 1; about 42 wt % of microcrystalline cellulose by weight of the composition; about 21 wt % of mannitol by weight of the composition; about 3 wt % of sodium croscarmellose sodium by weight of the composition; about 1 wt % of sodium lauryl sulfate by weight of the composition; about 2.5 wt % of magnesium stearate by weight of the composition; and about 0.5 wt % of colloidal silica by weight of the composition. Wherein the amount of Compound 1 in the shaped pharmaceutical tablet ranges from about 25 mg to about 250 mg, for example, 50 mg, or 75 mg, or 100 mg, or 150 mg, 200 mg, or 250 mg Compound 1 per tablet.

In still another pharmaceutical oral formulation of the invention, a shaped pharmaceutical tablet composition having an initial hardness of 5-21 kP±20 percent comprises: about 49 wt % of a Compound 1; about 29 wt % of microcrystalline cellulose by weight of the composition; about 12.6 wt % of mannitol by weight of the composition; about 4 wt % of sodium croscarmellose sodium by weight of the composition; about 4 wt % of polyvinylpyrrolidone by weight of the composition; about 1 wt % of sodium lauryl sulfate by weight of the composition; and about 0.5 wt % of magnesium stearate by weight of the composition. The amount of Compound 1 in the shaped pharmaceutical tablet ranges from about 25 mg to about 250 mg, for example, 50 mg, or 75 mg, or 100 mg, or 150 mg, 200 mg, or 250 mg Compound 1 per tablet.

In certain embodiments, the shaped pharmaceutical tablet contains about 100 mg of Compound 1. In certain embodiments, the shaped pharmaceutical tablet contains about 200 mg of Compound 1.

Another aspect of the invention provides a pharmaceutical formulation consisting of a tablet or capsule that includes a Compound 1 and other excipients (e.g., a filler, a disintegrant, a surfactant, a binder, a glidant, a colorant, a lubricant, or any combination thereof), each of which is described above and in the Examples below, wherein the tablet has a dissolution of at least about 50% (e.g., at least about 60%, at least about 70%, at least about 80%, at least about 90%, or at least about 99%) in about 30 minutes. In one example, the pharmaceutical composition consists of a tablet that includes Compound 1 in an amount ranging from 25 mg to 250 mg, for example, 25 mg, or 50 mg, or 75 mg, or 100 mg, or 150 mg, 200 mg, or 250 mg and one or more excipients (e.g., a filler, a disintegrant, a surfactant, a binder, a glidant, a colorant, a lubricant, or any combination thereof), each of which is described above and in the Examples below, wherein the tablet has a dissolution of from about 50% to about 100% (e.g., from about 55% to about 95% or from about 60% to about 90%) in about 30 minutes. In another example, the pharmaceutical composition consists of a tablet that comprises a composition comprising Compound 1; and one or more excipients from: a filler, a diluent, a disintegrant, a surfactant, a binder, a glidant, and a lubricant, wherein the tablet has a dissolution of at least about 50% (e.g., at least about 60%, at least about 70%, at least about 80%, at least about 90%, or at least about 99%) in about 30 minutes.

In one embodiment, the tablet comprises a composition comprising at least about 25 mg (e.g., at least about 30 mg, at least about 40 mg, or at least about 50 mg) of Compound 1; and one or more excipients from: a filler, a diluent, a disintegrant, a surfactant, a binder, a glidant, and a lubricant. In another embodiment, the tablet comprises a composition comprising at least about 25 mg (e.g., at least about 30 mg, at least about 40 mg, at least about 50 mg, at least about 100 mg, or at least 150 mg) of Compound 1 and one or more excipients from: a filler, a diluent, a disintegrant, a surfactant, a binder, a glidant, and a lubricant.

Dissolution can be measured with a standard USP Type II apparatus that employs a dissolution media of 0.1% CTAB dissolved in 900 mL of DI water, buffered at pH 6.8 with 50 mM potassium phosphate monoasic, stirring at about 50-75 rpm at a temperature of about 37° C. A single experimental tablet is tested in each test vessel of the apparatus. Dissolution can also be measured with a standard USP Type II apparatus that employs a dissolution media of 0.7% sodium lauryl sulfate dissolved in 900 mL of 50 mM sodium phosphate buffer (pH 6.8), stirring at about 65 rpm at a temperature of about 37° C. A single experimental tablet is tested in each test vessel of the apparatus. Dissolution can also be measured with a standard USP Type II apparatus that employs a dissolution media of 0.5% sodium lauryl sulfate dissolved in 900 mL of 50 mM sodium phosphate buffer (pH 6.8), stirring at about 65 rpm at a temperature of about 37° C. A single experimental tablet is tested in each test vessel of the apparatus.

Methods for Making Compound 1, Compound 1 Form I, Compound 1 Form II, Compound 1 HCl Salt Form A Compound 1

Compound 1 is used as the starting point for the other solid state forms and can be prepared by coupling an acid chloride moiety with an amine moiety according to Schemes 1-4.

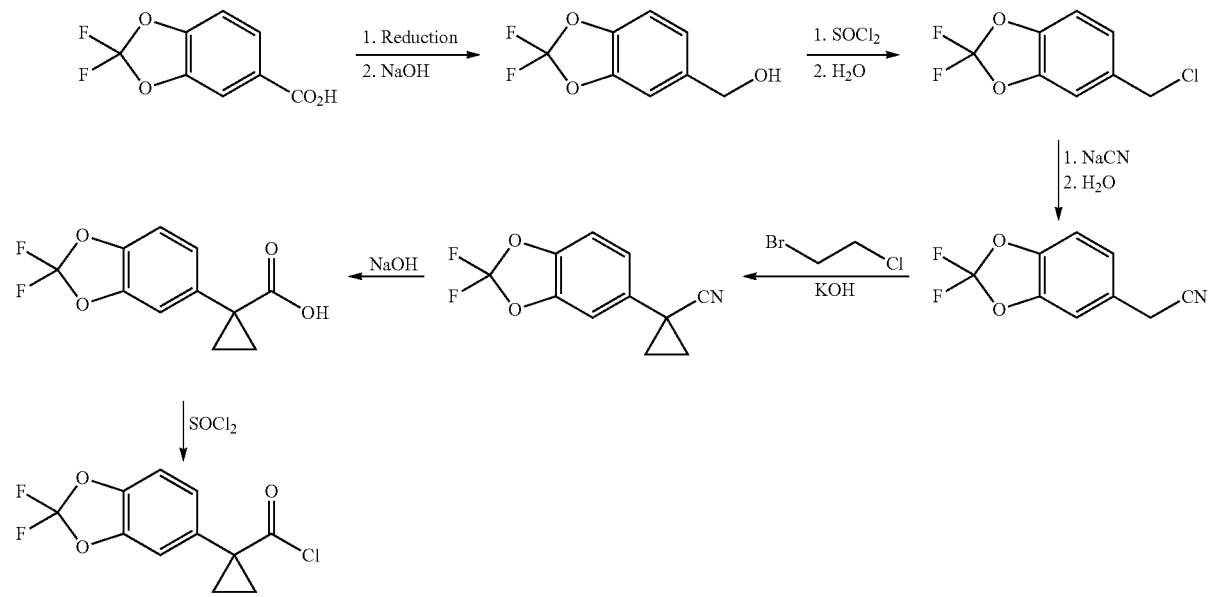

Scheme 1. Synthesis of the acid chloride moiety.

Scheme 1 depicts the preparation of 1-(2,2-difluorobenzo[d][1,3]dioxol-5-yl)cyclopropanecarbonyl chloride, which is used in Scheme 3 to make the amide linkage of Compound 1.

The starting material, 2,2-difluorobenzo[d][1,3]dioxole-5-carboxylic acid, is commercially available from Saltigo (an affiliate of the Lanxess Corporation). Reduction of the carboxylc acid moiety in 2,2-difluorobenzo[d][1,3]dioxole-5-carboxylic acid to the primary alcohol, followed by conversion to the corresponding chloride using thionyl chloride (SOCl$_2$), provides 5-(chloromethyl)-2,2-difluorobenzo[d][1,3]dioxole, which is subsequently converted to 2-(2,2-difluorobenzo[d][1,3]dioxol-5-yl)acetonitrile using sodium cyanide. Treatment of 2(2,2-difluorobenzo[d][1,3]dioxol-5-yl) acetonitrile with base and 1-bromo-2-chloroethane provides 1-(2,2-difluorobenzo[d][1,3]dioxol-5-yl)cyclopropanecarbonitrile. The nitrile moiety in 1-(2,2-difluorobenzo[d][1,3]dioxol-5-yl)cyclopropanecarbonitrile is converted to a carboxylic acid using base to give 1-(2,2-difluorobenzo[d][1,3]dioxol-5-yl)cyclopropanecarboxylic acid, which is converted to the desired acid chloride using thionyl chloride.

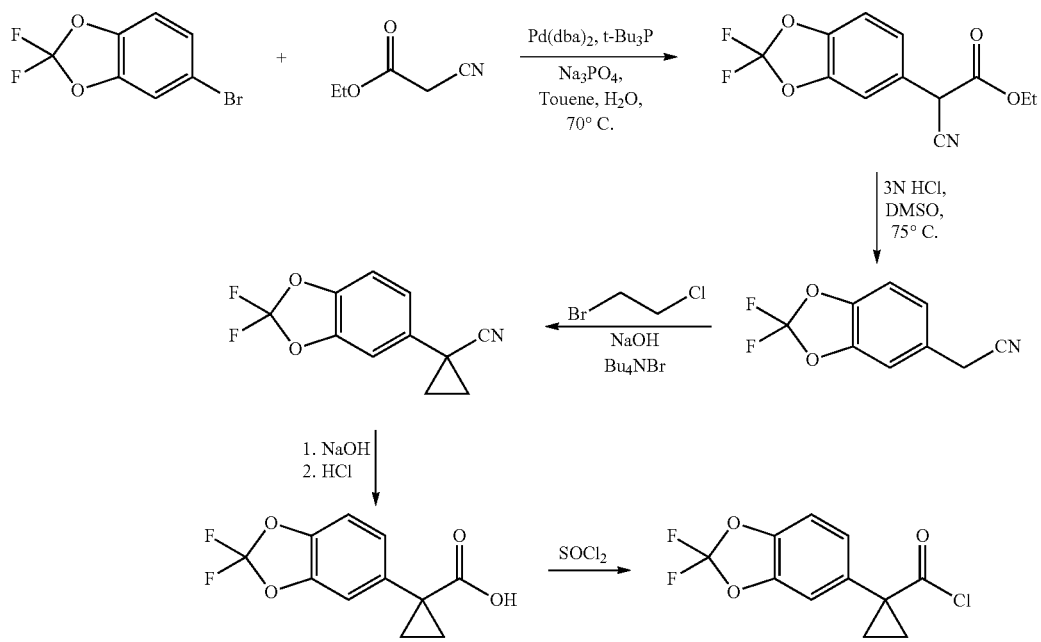

Scheme 2. Alternative synthesis of the acid chloride moiety.

Scheme 2 depicts an alternative synthesis of the requisite acid chloride. 5-bromomethyl-2,2-difluoro-1,3-benzodioxole is coupled with ethyl cyanoacetate in the presence of a palladium catalyst to form the corresponding alpha cyano ethyl ester. Saponification of the ester moiety to the carboxylic acid gives the cyanoethyl compound. Alkylation of the cyanoethyl compound with 1-bromo-2-chloro ethane in the presence of base gives the cyanocyclopropyl compound. Treatment of the cyanocyclopropyl compound with base gives the carboxylate salt, which is converted to the carboxylic acid by treatment with acid. Conversion of the carboxylic acid to the acid chloride is then accomplished using a chlorinating agent such as thionyl chloride or the like.

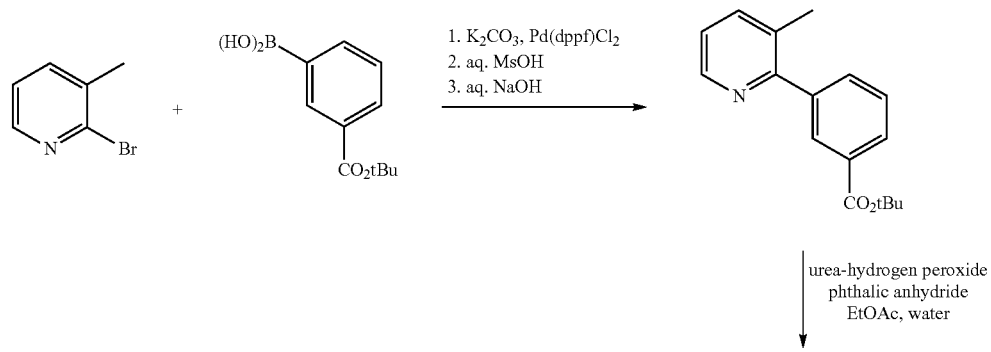

Scheme 3. Synthesis of the amine moiety.

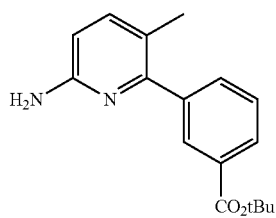 ← 1. Ms₂O, py, MeCN
2. ethanolamine
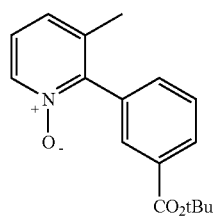

Scheme 3 depicts the preparation of the requisite tert-butyl 3-(6-amino-3-methylpyridin-2-yl)benzoate, which is coupled with 1-(2,2-difluorobenzo[d][1,3]dioxol-5-yl)cyclopropanecarbonyl chloride in Scheme 3 to give Compound 1. Palladium-catalyzed coupling of 2-bromo-3-methylpyridine with 3-(tert-butoxycarbonyl)phenylboronic acid gives tert-butyl 3-(3-methylpyridin-2-yl)benzoate, which is subsequently converted to the desired compound.

Scheme 4. Formation of an acid salt of 3-(6-(1-(2,2-difluorobenzo[d][1,3]dioxol-5-yl)cyclopropanecarboxamido)-3-methylpyridin-2-yl)benzoic acid.

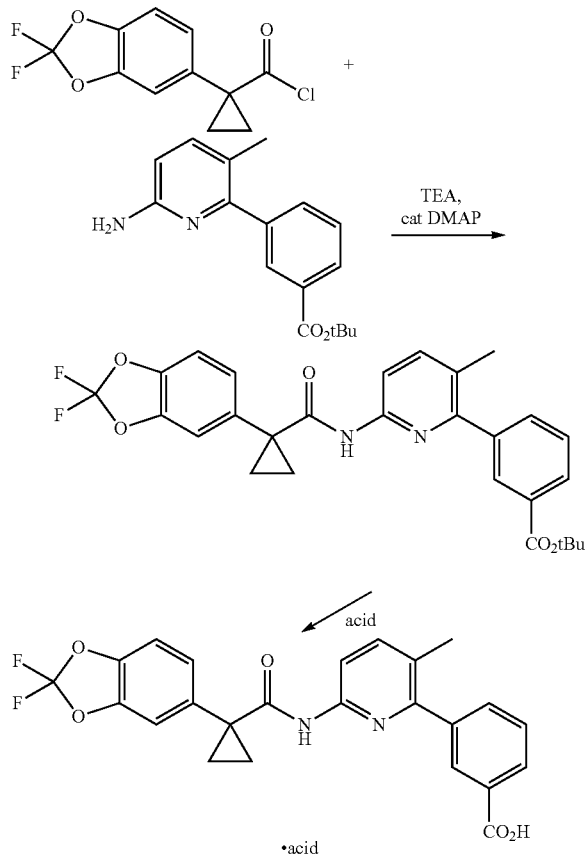

Scheme 4 depicts the coupling of 1-(2,2-difluorobenzo[d][1,3]dioxol-5-yl)cyclopropanecarbonyl chloride with tert-butyl 3-(6-amino-3-methylpyridin-2-yl)benzoate using triethyl amine and 4-dimethylaminopyridine to initially provide the tert-butyl ester of Compound 1.

Compound 1 Form I

Compound 1 Form I is prepared by dispersing or dissolving a salt form, such as the HCl salt, of Compound 1 in an appropriate solvent for an effective amount of time. Treatment of the tert-butyl ester with an acid such as HCl, gives the HCL salt of Compound 1, which is typically a crystalline solid. Compound 1 Form I may also be prepared directly from the t-butyl ester precursor by treatment with an appropriate acid, such as formic acid.

The HCl salt of 3-(6-(1-(2,2-difluorobenzo[d][1,3]dioxol-5-yl) cyclopropanecarboxamido)-3-methylpyridin-2-yl)benzoic acid can be used to make Form I by dispersing or dissolving the HCl salt of 3-(6-(1-(2,2-difluorobenzo[d][1,3]dioxol-5-yl) cyclopropanecarboxamido)-3-methylpyridin-2-yl)benzoic acid in an appropriate solvent for an effective amount of time. Other salts of 3-(6-(1-(2,2-difluorobenzo[d][1,3]dioxol-5-yl) cyclopropanecarboxamido)-3-methylpyridin-2-yl)benzoic acid may be used, such as, for example, salts derived from other mineral or organic acids. The other salts result from acid-mediated hydrolysis of the t-butyl ester moiety. Salts derived from other acids may include, for example, nitric, sulfuric, phosphoric, boric, acetic, benzoic and malonic. These salt forms of 3-(6-(1-(2,2-difluorobenzo[d][1,3]dioxol-5-yl) cyclopropanecarboxamido)-3-methylpyridin-2-yl)benzoic acid may or may not be soluble, depending upon the solvent used, but lack of solubility does not hinder formation of Form I. For example, in one embodiment, the appropriate solvent may be water or an alcohol/water mixture such as 50% methanol/water mixture, even though the HCl salt form of 3-(6-(1-(2,2-difluorobenzo[d][1,3]dioxol-5-yl) cyclopropanecarboxamido)-3-methylpyridin-2-yl)benzoic acid is only sparingly soluble in water. In one embodiment, the appropriate solvent is water.

The effective amount of time for formation of Form I from the salt of 3-(6-(1-(2,2-difluorobenzo[d][1,3]dioxol-5-yl) cyclopropanecarboxamido)-3-methylpyridin-2-yl)benzoic acid can be any time between 2 to 24 hours or greater. It is recognized that the amount of time needed is inversely proportional to the temperature. That is, the higher the temperature the less time needed to affect dissociation of acid to form Form I. When the solvent is water, stirring the dispersion for approximately 24 hours at room temperature provides Form in an approximately 98% yield. If a solution of the salt of 3-(6-(1-(2,2-difluorobenzo[d][1,3]dioxol-5-yl) cyclopropanecarboxamido)-3-methylpyridin-2-yl)benzoic acid is desired for process purposes, an elevated temperature may be used. After stirring the solution for an effective amount of time at the elevated temperature, recrystallization upon cooling provides substantially pure Form I. In one embodiment, substantially pure refers to greater than about 90% purity. In another embodiment, substantially pure refers to greater than about 95% purity. In another embodiment, substantially pure refers to greater than about 98% purity. In another embodiment, substantially pure refers to greater than about 99% purity. The temperature selected depends in part on the solvent used and is well within the determination capabilities of one of ordinary skill in the art. In one embodiment, the temperature is between room temperature and about 80° C. In another embodiment, the temperature is between room temperature and about 40° C. In another embodiment, the temperature is between about 40° C. and about 60° C. In another embodiment, the temperature is between about 60° C. and about 80° C.

Compound 1 Form I may also be formed directly from 3-(6-(1-(2,2-difluorobenzo[d][1,3]dioxol-5-yl) cyclopropanecarboxamido)-3-methylpyridin-2-yl)-t-butylbenzoate (cf. Scheme 3), which is a precursor to the salt of Compound 1. Thus, 3-(6-(1-(2,2-difluorobenzo[d][1,3]dioxol-5-yl) cyclopropanecarboxamido)-3-methylpyridin-2-yl)-t-butylbenzoate is allowed to undergo reaction with an appropriate acid, such as, for example, formic acid under appropriate reaction conditions to give Compound 1 Form I.

Compound 1 Form I may be further purified by recrystallization from an organic solvent. Examples of organic solvents include, but are not limited to, toluene, cumene, anisol, 1-butanol, isopropyl acetate, butyl acetate, isobutyl acetate, methyl t-butyl ether, methyl isobutyl ketone and 1-propanol-water mixtures. The temperature may be as described above. For example, Form I is dissolved in 1-butanol at 75° C. until it is completely dissolved. Cooling down the solution to 10° C. at a rate of 0.2° C./min yields crystals of Form I which may be isolated by filtration.

In one embodiment, Compound 1 Form I is characterized by one or more peaks at 15.2 to 15.6 degrees, 16.1 to 16.5 degrees, and 14.3 to 14.7 degrees in an X-ray powder diffraction obtained using Cu K alpha radiation. In another embodiment, Compound 1 Form I is characterized by one or more peaks at 15.4, 16.3, and 14.5 degrees. In another embodiment, Compound 1 Form I is further characterized by a peak at 14.6 to 15.0 degrees. In another embodiment, Compound 1 Form I is further characterized by a peak at 14.8 degrees. In another embodiment, Compound 1 Form I is further characterized by a peak at 17.6 to 18.0 degrees. In another embodiment, Compound 1 Form I is further characterized by a peak at 17.8 degrees. In another embodiment, Compound 1 Form I is further characterized by a peak at 16.4 to 16.8 degrees. In another embodiment, Compound 1 Form I is further characterized by a peak at 16.4 to 16.8 degrees. In another embodiment, Compound 1 Form I is further characterized by a peak at 16.6 degrees. In another embodiment, Compound 1 Form I is further characterized by a peak at 7.6 to 8.0 degrees. In another embodiment, Compound 1 Form I is further characterized by a peak at 7.8 degrees. In another embodiment, Compound 1 Form I is further characterized by a peak at 25.8 to 26.2 degrees. In another embodiment, Compound 1 Form I is further characterized by a peak at 26.0 degrees. In another embodiment, Compound 1 Form I is further characterized by a peak at 21.4 to 21.8 degrees. In another embodiment, Compound 1 Form I is further characterized by a peak at 21.6 degrees. In another embodiment, Compound 1 Form I is further characterized by a peak at 23.1 to 23.5 degrees. In another embodiment, Compound 1 Form I is further characterized by a peak at 23.3 degrees. In some embodiments, Compound 1 Form I is characterized by a diffraction pattern substantially similar to that of FIG. 1. In some embodiments, Compound 1 Form I is characterized by a diffraction pattern substantially similar to that of FIG. 2.

In some embodiments, the particle size distribution of D90 is about 82 μm or less for Compound 1 Form I. In some embodiments, the particle size distribution of D50 is about 30 μm or less for Compound 1 Form I.

Compound 1 Form II

Compound 1 Form II is prepared by slurrying Compound 1 Form I in an appropriate solvent at a sufficient concentration for a sufficient time. The slurry is then filtered centrifugally or under vacuum and dried at ambient conditions for sufficient time to yield Compound 1 Form II.

In some embodiments, about 20 to 40 mg of Compound 1 Form I is slurried in about 400 to 600 μL of an appropriate solvent. In another embodiment, about 25 to 35 mg of Compound 1 Form I is slurried in about 450 to 550 μL of an appropriate solvent. In another embodiment, about 30 mg of Compound 1 Form I is slurried in about 500 μL of an appropriate solvent.

In some embodiments, the time that Compound 1 Form I is allowed to slurry with the solvent is from 1 hour to four days. More particularly, the time that Compound 1 Form I is allowed to slurry with the solvent is from 1 to 3 days. More particularly, the time is 2 days.

In some embodiments, the appropriate solvent is selected from an organic solvent of sufficient size to fit the voids in the crystalline lattice of Compound 1 Form II. In other embodiments, the solvate is of sufficient size to fit in voids measuring about 100 Å$^3$.

In other embodiments, the solvent is selected from the group consisting of methanol, ethanol, acetone, 2-propanol, acetonitrile, tetrahydrofuran, methyl acetate, 2-butanone, ethyl formate, and 2-methyl tetrahydrofuran.

In other embodiments, a mixture of two or more of these solvents may be used to obtain Compound 1 Form II. Alternatively, Compound 1 Form II may be obtained from a mixture comprising one or more of these solvents and water.

In some embodiments, the effective amount of time for drying Compound 1 Form II is 1 to 24 hours. More particularly, the time is 6 to 18 hours. More particularly, the time is about 12 hours.

In another embodiment, Compound 1 Form II is prepared by dispersing or dissolving a salt form of Compound 1, such as an HCl salt of Compound 1 in an appropriate solvent for an effective amount of time.

Compound 1 Form II as disclosed herein comprises a crystalline lattice of Compound 1 in which voids in the crystalline lattice are empty, or occupied, or partially occupied by one or more molecules of a suitable solvent. Suitable solvents include, but are not limited to, methanol, ethanol, acetone, 2-propanol, acetonitrile, tetrahydrofuran, methyl acetate, 2-butanone, ethyl formate, and 2-methyl tetrahydrofuran. Certain physical characterisics of Compound 1 isostructural solvate forms, such as X-ray powder diffraction, melting point and DSC, are not substantially affected by the particular solvent molecule in question.

In one embodiment, Compound 1 Form II is characterized by one or more peaks at 21.50 to 21.90 degrees, 8.80 to 9.20 degrees, and 10.80 to 11.20 degrees in an X-ray powder diffraction obtained using Cu K alpha radiation. In another embodiment, Compound 1 Form II is characterized by one or more peaks at 21.50 to 21.90 degrees, 8.80 to 9.20 degrees, 10.80 to 11.20 degrees, 18.00 to 18.40 degrees, and 22.90 to 23.30 degrees in an X-ray powder diffraction obtained using Cu K alpha radiation. In another embodiment, Compound 1 Form II is characterized by one or more peaks at 21.70, 8.98, and 11.04 degrees. In another embodiment, Compound 1 Form II is characterized by one or more peaks at 21.70, 8.98, 11.04, 18.16, and 23.06 degrees. In another embodiment, Compound 1 Form II is characterized by a peak at 21.50 to 21.90 degrees. In another embodiment, Compound 1 Form II is further characterized by a peak at 21.70 degrees. In another embodiment, Compound 1 Form II is further characterized by a peak at 8.80 to 9.20 degrees. In another embodiment, Compound 1 Form II is further characterized by a peak at 8.98 degrees. In another embodiment, Compound 1 Form II is further characterized by a peak at 10.80 to 11.20 degrees. In another embodiment, Compound 1 Form II is further characterized by a peak at 11.04. In another embodiment, Compound 1 Form II is further characterized by a peak at 18.00 to 18.40 degrees. In another embodiment, Compound 1 Form II is further characterized by a peak at 18.16 degrees. In another embodiment, Compound 1 Form II is further characterized by a peak at 22.90 to 23.30 degrees. In another embodiment, Compound 1 Form II is further characterized by a peak at 23.06 degrees. In another embodiment, Compound 1 Form II is further characterized by a peak at 20.40 to 20.80 degrees. In another embodiment, Compound 1 Form II is further characterized by a peak at 20.63 degrees. In another embodiment, Compound 1 Form II is further characterized by a peak at 22.00 to 22.40 degrees. In another embodiment, Compound 1 Form II is further characterized by a peak at 22.22 degrees. In another embodiment, Compound 1 Form II is further characterized by a peak at 18.40 to 18.80 degrees. In another embodiment, Compound 1 Form II is further characterized by a peak at 18.57 degrees. In another embodiment, Compound 1 Form II is further characterized by a peak at 16.50 to 16.90 degrees. In another embodiment, Compound 1 Form II is further characterized by a peak at 16.66 degrees. In another embodiment, Compound 1 Form II is further characterized by a peak at 19.70 to 20.10 degrees. In another embodiment, Compound 1 Form II is further characterized by a peak at 19.86 degrees.

Figure 3:
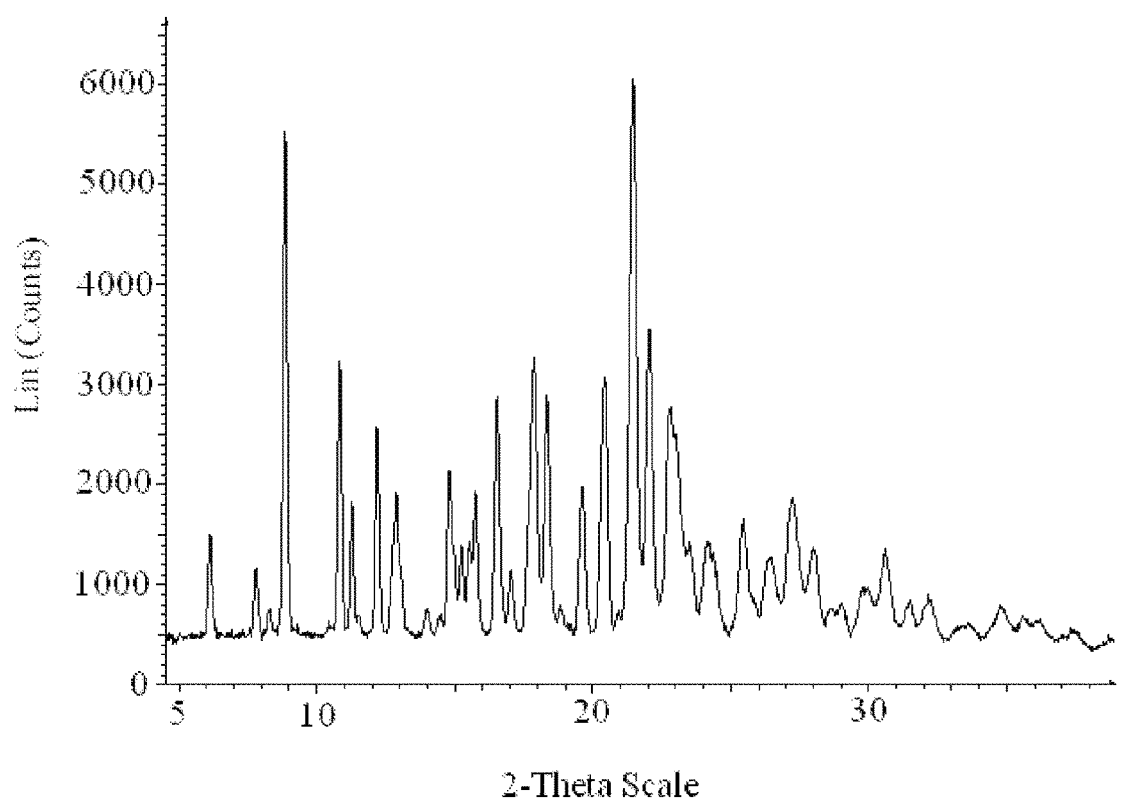
FIG. 3 is an X-ray powder diffraction pattern of Compound 1 Form II.
Figure 4:
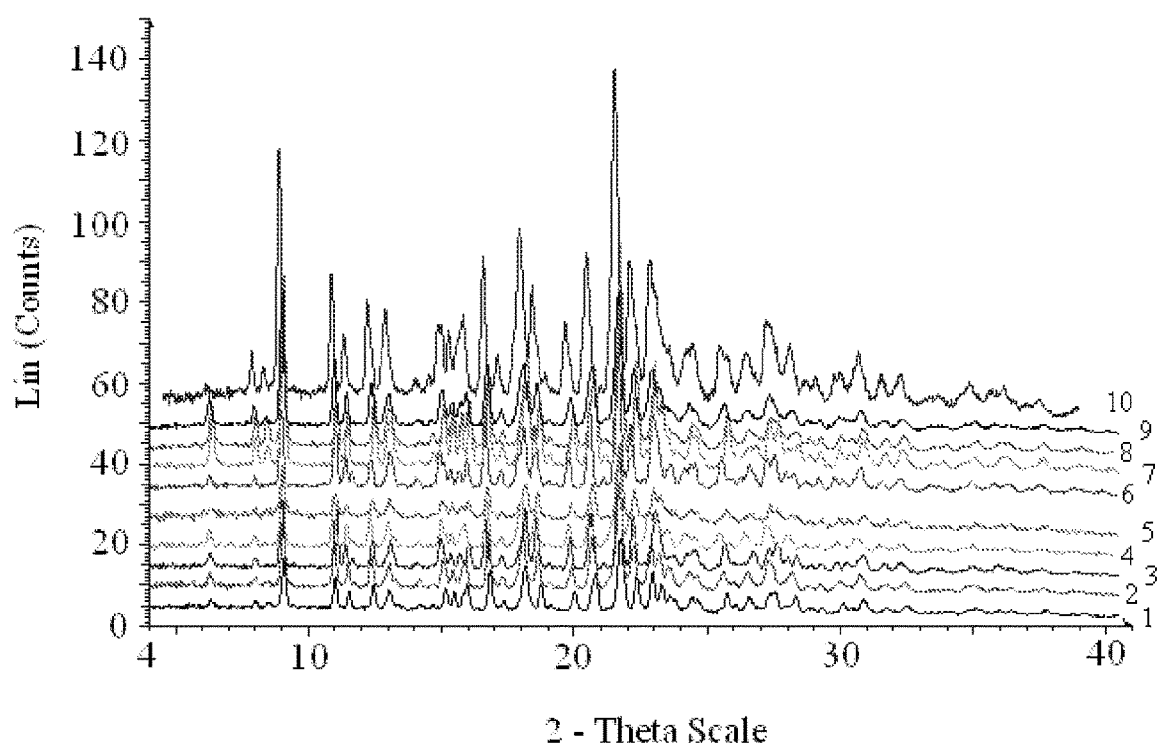

In some embodiments, Compound 1 Form II is characterized by a diffraction pattern substantially similar to that of FIG. 3. In some embodiments, Compound 1 Form II is characterized by diffraction patterns substantially similar to those provided in FIG. 4.

In another embodiment, the solvate that forms Compound 1 Form II is selected from the group consisting of methanol, ethanol, acetone, 2-propanol, acetonitrile, tetrahydrofuran, methyl acetate, 2-butanone, ethyl formate, and 2-methyl tetrahydrofuran. Diffraction patterns are provided for the following Compound 1 Form II: methanol (FIG. 5), ethanol (FIG. 6), acetone (FIG. 7), 2-propanol (FIG. 8), acetonitrile (FIG. 9), tetrahydrofuran (FIG. 10), methyl acetate (FIG. 11), 2-butanone (FIG. 12), ethyl formate (FIG. 13), and 2-methytetrahydrofuran (FIG. 14).

In another embodiment, the invention provides Compound 1 Form II which exhibits two or more phase transitions as determined by DSC or a similar analytic method known to the skilled artisan. In some embodiments, the DSC of Compound 1 Form II is substantially similar to the DSC trace depicted in FIG. 15. In another embodiment of this aspect, the DSC gives two phase transitions. In another embodiment, the DSC gives three phase transitions. In another embodiment, one of the phase transitions occurs between 200 and 207° C. In another embodiment, one of the phase transitions occurs between 204 and 206° C. In another embodiment, one of the phase transitions occurs between 183 and 190° C. In another embodiment, one of the phase transitions occurs between 185 and 187° C. In another embodiment, the melting point of Compound 1, Solvate Form A is between 183° C. to 190° C. In another embodiment, the melting point of Compound 1, Solvate Form A is between 185° C. to 187° C.

In another embodiment, Compound 1 Form II comprises 1 to 10 weight percent (wt. %) solvate as determined by TGA. In some embodiments, the TGA of Compound 1 Form II is substantially similar to the TGA trace depicted in FIG. 16. In another embodiment, Compound 1 Form II comprises 2 to 5 wt. % solvate as determined by TGA or a similar analytic method known to the skilled artisan.

In another embodiment, the conformation of Compound 1 Form II acetone solvate is substantially similar to that depicted in FIG. 17, which is based on single X-ray analysis.

In another embodiment, Compound 1 Form II acetone solvate has a $P2_1/n$ space group, and the following unit cell dimensions:
a=16.5235 (10) Å α=90°
b=12.7425 (8) Å β=103.736 (4)°
c=20.5512 (13) Å γ=90°.

Compound 1 HCl Salt Form A

Compound 1 HCl Salt Form A can be prepared from the HCl salt of Compound 1, by dissolving the HCl salt of Compound 1 in a minimum of solvent and removing the solvent by slow evaporation. In another embodiment, the solvent is an alcohol. In another embodiment, the solvent is ethanol. Slow evaporation is generally carried out by impeding the evaporation of the solvent. For example, in one embodiment, slow evaporation involves dissolving the HCl salt of Compound 1 in a vial and covering the vial with parafilm that contains a hole poked in it.

In one embodiment, Compound 1 HCl Salt Form A is characterized by one or more peaks at 8.80 to 9.20 degrees, 17.30 to 17.70 degrees, and 18.20 to 18.60 degrees in an X-ray powder diffraction obtained using Cu K alpha radiation. In another embodiment, Compound 1 HCl Salt Form A is characterized by one or more peaks at 8.80 to 9.20 degrees, 17.30 to 17.70 degrees, 18.20 to 18.60 degrees, 10.10 to 10.50, and 15.80 to 16.20 degrees in an X-ray powder diffraction obtained using Cu K alpha radiation. In another embodiment, Compound 1 HCl Salt Form A is characterized by one or more peaks at 8.96, 17.51, and 18.45 degrees. In another embodiment, Compound 1 HCl Salt Form A is characterized by one or more peaks at 8.96, 17.51, 18.45. 10.33, and 16.01 degrees. In another embodiment, Compound 1 HCl Salt Form A is characterized by a peak at 8.80 to 9.20 degrees. In another embodiment, Compound 1 HCl Salt Form A is characterized by a peak at 8.96 degrees. In another embodiment, Compound 1 HCl Salt Form A is further characterized by a peak at 17.30 to 17.70 degrees. In another embodiment, Compound 1 HCl Salt Form A is characterized by a peak at 17.51 degrees. In another embodiment, Compound 1 HCl Salt Form A is further characterized by a peak at 18.20 to 18.60 degrees. In another embodiment, Compound 1 HCl Salt Form A is further characterized by a peak at 18.45 degrees. In another embodiment, Compound 1 HCl Salt Form A is further characterized by a peak at 10.10 to 10.50 degrees. In another embodiment, Compound 1 HCl Salt Form A is further characterized by a peak at 10.33 degrees. In another embodiment, Compound 1 HCl Salt Form A is further characterized by a peak at 15.80 to 16.20 degrees. In another embodiment, Compound 1 HCl Salt Form A is further characterized by a peak at 16.01 degrees. In another embodiment, Compound 1 HCl Salt Form A is further characterized by a peak at 11.70 to 12.10 degrees. In another embodiment, Compound 1 HCl Salt Form A is further characterized by a peak at 11.94 degrees. In another embodiment, Compound 1 HCl Salt Form A is further characterized by a peak at 7.90 to 8.30 degrees. In another embodiment, Compound 1 HCl Salt Form A is further characterized by a peak at 8.14 degrees. In another embodiment, Compound 1 HCl Salt Form A is further characterized by a peak at 9.90 to 10.30 degrees. In another embodiment, Compound 1 HCl Salt Form A is further characterized by a peak at 10.10 degrees. In another embodiment, Compound 1 HCl Salt Form A is further characterized by a peak at 16.40 to 16.80 degrees. In another embodiment, Compound 1 HCl Salt Form A is further characterized by a peak at 16.55 degrees. In another embodiment, Compound 1 HCl Salt Form A is further characterized by a peak at 9.30 to 9.70 degrees. In another embodiment, Compound 1 HCl Salt Form A is further characterized by a peak at 9.54 degrees. In another embodiment, Compound 1 HCl Salt Form A is further characterized by a peak at 16.40 to 16.80 degrees. In another embodiment, Compound 1 HCl Salt Form A is further characterized by a peak at 16.55 degrees. In some embodiments, Compound 1 HCl Salt Form A is characterized as a dimer as depicted in FIG. 18.

In some embodiments, Compound 1 HCl Salt Form A is characterized by a diffraction pattern substantially similar to that of FIG. 19.

In another embodiment, the invention features crystalline Compound 1 HCl Salt Form A having a P$^-$1 space group, and the following unit cell dimensions:

a=10.2702 (2) Å α=67.0270 (10)°
b=10.8782 (2) Å β=66.1810 (10)°
c=12.4821 (3) Å γ=72.4760 (10)°.

Methods for Making the Pharmaceutical Compositions

The dosage unit forms of the invention can be produced by compacting or compressing an admixture or composition, for example, a powder or granules, under pressure to form a stable three-dimensional shape (e.g., a tablet). As used herein, "tablet" includes compressed pharmaceutical dosage unit forms of all shapes and sizes, whether coated or uncoated.

The expression "dosage unit form" as used herein refers to a physically discrete unit of agent appropriate for the patient to be treated. In general, a compacted mixture has a density greater than that of the mixture prior to compaction. A dosage unit form of the invention can have almost any shape including concave and/or convex faces, rounded or angled corners, and a rounded to rectilinear shape. In some embodiments, the compressed dosage forms of the invention comprise a rounded tablet having flat faces. The solid pharmaceutical dosage forms of the invention can be prepared by any compaction and compression method known by persons of ordinary skill in the art of forming compressed solid pharmaceutical dosage forms. In particular embodiments, the formulations provided herein may be prepared using conventional methods known to those skilled in the field of pharmaceutical formulation, as described, e.g., in pertinent textbooks. See, e.g., Remington: The Science and Practice of Pharmacy, 21st Ed., Lippincott Williams & Wilkins, Baltimore, Md. (2003); Ansel et al., Pharmaceutical Dosage Forms And Drug Delivery Systems, 7th Edition, Lippincott Williams & Wilkins, (1999); The Handbook of Pharmaceutical Excipients, 4$^{th}$ edition, Rowe et al., Eds., American Pharmaceuticals Association (2003); Gibson, Pharmaceutical Preformulation And Formulation, CRC Press (2001), these references hereby incorporated herein by reference in their entirety.

Granulation and Compression

In some embodiments, solid forms, including powders comprising the active agent Compound 1 and the included pharmaceutically acceptable excipients (e.g. filler, diluent, disintegrant, surfactant, glidant, binder, lubricant, or any combination thereof) can be subjected to a dry granulation process. The dry granulation process causes the powder to agglomerate into larger particles having a size suitable for further processing. Dry granulation can improve the flowability of a mixture in order to be able to produce tablets that comply with the demand of mass variation or content uniformity.

Formulations as described herein may be produced using one or more mixing and dry granulations steps. The order and the number of the mixing and granulation steps do not seem to be critical. However, at least one of the excipients and Compound 1 can be been subject to dry granulation or wet high shear granulation before compression into tablets. Dry granulation of Compound 1 and the excipients made together prior to tablet compression seem, surprisingly, to be a simple, inexpensive and efficient way of providing close physical contact between the ingredients of the present compositions and formulations and thus results in a tablet formulation with good stability properties. Dry granulation can be carried out by a mechanical process, which transfers energy to the mixture without any use of any liquid substances (neither in the form of aqueous solutions, solutions based on organic solutes, or mixtures thereof) in contrast to wet granulation processes, also contemplated herein. Generally, the mechanical process requires compaction such as the one provided by roller compaction. An example of an alternative method for dry granulation is slugging.

In some embodiments, roller compaction is a granulation process comprising highly intensive mechanical compacting of one or more substances. In some embodiments, a pharmaceutical composition comprising an admixture of powders is pressed, that is roller compacted, between 2 counter rotating rollers to make a solid sheet which is subsequently crushed in a sieve to form a particulate matter. In this particulate matter, a close mechanical contact between the ingredients can be obtained. An example of roller compaction equipment is Minipactor® a Gerteis 3W-Polygran from Gerteis Maschinen+Processengineering AG.

In some embodiments, tablet compression according to the invention can occur without any use of any liquid substances (neither in the form of aqueous solutions, solutions based on organic solutes, or mixtures thereof), i.e. a dry granulation process. In a typical embodiment the resulting core or tablet has a compressive strength in the range of 1 to 15 kP; such as 1.5 to 12.5 kP, preferably in the range of 2 to 10 kP.

Brief Manufacturing Procedure

In some embodiments, the ingredients are weighed according to the formula set herein. Next, all of the intra-granular ingredients are sifted and mixed well. The ingredients can be lubricated with a suitable lubricant, for example, magnesium stearate. The next step can comprise compaction/slugging of the powder admixture and sized ingredients. Next, the compacted or slugged blends are milled into granules and sifted to obtain the desired size. Next, the granules can be further lubricated with, for example, magnesium stearate. Next the granular composition of the invention can be compressed on suitable punches into various pharmaceutical formulations in accordance with the invention. Optionally the tablets can be coated with a film, colorant or other coating.

Another aspect of the invention provides a method for producing a pharmaceutical composition comprising providing an admixture of a composition comprising Compound 1 and one or more excipients selected from: a filler, a diluent, a binder, a glidant, a surfactant, a lubricant, a disintegrant, and compressing the composition into a tablet having a dissolution of at least about 50% in about 30 minutes.

In another embodiment, a wet granulation process is performed to yield the pharmaceutical formulation of the invention from an admixture of powdered and liquid ingredients. For example, a pharmaceutical composition comprising an admixture of a composition comprising Compound 1 and one or more excipients selected from: a filler, a diluent, a binder, a glidant, a surfactant, a lubricant, a disintegrant, are weighed as per the formula set herein. Next, all of the intragranular ingredients are sifted and mixed in a high shear or low shear granulator using water or water with a surfactant or water with a binder or water with a surfactant and a binder to granulate the powder blend. A fluid other than water can also be used with or without surfactant and/or binder to granulate the powder blend. Next, the wet granules can optionally be milled using a suitable mill. Next, water may optionally be removed from the admixture by drying the ingredients in any suitable manner. Next, the dried granules can optionally be milled to the required size. Next, extra granular excipients can be added by blending (for example a filler, a diluent, and a disintegrant). Next, the sized granules can be further lubricated with magnesium stearate and a disintegrant, for example, croscarmellose sodium. Next the granular composition of the invention can be sifted for sufficient time to obtain the correct size and then compressed on suitable punches into various pharmaceutical formulations in accordance with the invention. Optionally, the tablets can be coated with a film, colorant or other coating.

Each of the ingredients of this exemplary admixture is described above and in the Examples below. Furthermore, the admixture can comprise optional additives, such as, one or more colorants, one or more flavors, and/or one or more fragrances as described above and in the Examples below. In some embodiments, the relative concentrations (e.g., wt %) of each of these ingredients (and any optional additives) in the admixture are also presented above and in the Examples below. The ingredients constituting the admixture can be provided sequentially or in any combination of additions; and, the ingredients or combination of ingredients can be provided in any order. In one embodiment, the lubricant is the last component added to the admixture.

In another embodiment, the admixture comprises a composition of Compound 1, and any one or more of the excipients; a binder, a glidant, a surfactant, a diluent, a lubricant, a disintegrant, and a filler, wherein each of these ingredients is provided in a powder form (e.g., provided as particles having a mean or average diameter, measured by light scattering, of 250 µm or less (e.g., 150 µm or less, 100 µm or less, 50 µm or less, 45 µm or less, 40 µm or less, or 35 µm or less)). For instance, the admixture comprises a composition of Compound 1, a diluent, a glidant, a surfactant, a lubricant, a disintegrant, and a filler, wherein each of these ingredients is provided in a powder form (e.g., provided as particles having a mean diameter, measured by light scattering, of 250 µm or less (e.g., 150 µm or less, 100 µm or less, 50 µm or less, 45 µm or less, 40 µm or less, or 35 µm or less)). In another example, the admixture comprises a composition of Compound 1, a diluent, a binder, a surfactant, a lubricant, a disintegrant, and a filler, wherein each of these ingredients is provided in a powder form (e.g., provided as particles having a mean diameter, measured by light scattering, of 250 µm or less (e.g., 150 µm or less, 100 µm or less, 50 µm or less, 45 µm or less, 40 µm or less, or 35 µm or less))

In another embodiment, the admixture comprises a composition of Compound 1, and any combination of: a binder, a glidant, a diluent, a surfactant, a lubricant, a disintegrant, and a filler, wherein each of these ingredients is substantially free of water. Each of the ingredients comprises less than 5 wt % (e.g., less than 2 wt %, less than 1 wt %, less than 0.75 wt %, less than 0.5 wt %, or less than 0.25 wt %) of water by weight of the ingredient. For instance, the admixture comprises a composition of Compound 1, a diluent, a glidant, a surfactant, a lubricant, a disintegrant, and a filler, wherein each of these ingredients is substantially free of water. In some embodiments, each of the ingredients comprises less than 5 wt % (e.g., less than 2 wt %, less than 1 wt %, less than 0.75 wt %, less than 0.5 wt %, or less than 0.25 wt %) of water by weight of the ingredient.

In another embodiment, compressing the admixture into a tablet is accomplished by filling a form (e.g., a mold) with the admixture and applying pressure to admixture. This can be accomplished using a die press or other similar apparatus. In some embodiments, the admixture of Compound 1 and excipients can be first processed into granular form. The granules can then be sized and compressed into tablets or formulated for encapsulation according to known methods in the pharmaceutical art. It is also noted that the application of pressure to the admixture in the form can be repeated using the same pressure during each compression or using different pressures during the compressions. In another example, the admixture of powdered ingredients or granules can be compressed using a die press that applies sufficient pressure to form a tablet having a dissolution of about 50% or more at about 30 minutes (e.g., about 55% or more at about 30 minutes or about 60% or more at about 30 minutes). For instance, the admixture is compressed using a die press to produce a tablet hardness of at least about 5 kP (at least about 5.5 kP, at least about 6 kP, at least about 7 kP, at least about 10 kP, or at least 15 kP). In some instances, the admixture is compressed to produce a tablet hardness of between about 5 and 20 kP.

In some embodiments, tablets comprising a pharmaceutical composition as described herein can be coated with about 3.0 wt % of a film coating comprising a colorant by weight of the tablet. In certain instances, the colorant suspension or solution used to coat the tablets comprises about 20% w/w of solids by weight of the colorant suspension or solution. In still further instances, the coated tablets can be labeled with a logo, other image or text.

In another embodiment, the method for producing a pharmaceutical composition comprises providing an admixture of a solid forms, e.g. an admixture of powdered and/or liquid ingredients, the admixture comprising Compound 1 and one or more excipients selected from: a binder, a glidant, a diluent, a surfactant, a lubricant, a disintegrant, and a filler; mixing the admixture until the admixture is substantially homogenous, and compressing or compacting the admixture into a granular form. Then the granular composition comprising Compound 1 can be compressed into tablets or formulated into capsules as described above or in the Examples below. Alternatively, methods for producing a pharmaceutical composition comprises providing an admixture of Compound 1, and one or more excipients, e.g. a binder, a glidant, a diluent, a surfactant, a lubricant, a disintegrant, and a filler; mixing the admixture until the admixture is substantially homogenous, and compressing/compacting the admixture into a granular form using a roller compactor using a dry granulation composition as set forth in the Examples below or alternatively, compressed/compacted into granules using a high shear wet granule compaction process as set forth in the Examples below. Pharmaceutical formulations, for example a tablet as described herein, can be made using the granules prepared incorporating Compound 1 in addition to the selected excipients described herein.

In some embodiments, the admixture is mixed by stirring, blending, shaking, or the like using hand mixing, a mixer, a blender, any combination thereof, or the like. When ingredients or combinations of ingredients are added sequentially, mixing can occur between successive additions, continuously throughout the ingredient addition, after the addition of all of the ingredients or combinations of ingredients, or any combination thereof. The admixture is mixed until it has a substantially homogenous composition.

In another embodiment, the present invention comprises jet milling Compound 1, Compound 1 Form I, Compound 1 Form II, Compound 1 HCl Salt Form A in a suitable, conventional milling apparatus using air pressure suitable to produce particles having a significant particle size fraction between 0.1 microns and 50 microns. In another embodiment, the particle size is between 0.1 microns and 20 microns. In another embodiment, the particles size is between 0.1 microns and 10 microns. In another embodiment, the particle size is between 1.0 microns and 5 microns. In still another embodiment, Compound 1, Compound 1 Form I, Compound 1 Form II, Compound 1 HCl Salt Form A has a particle size D50 of 2.0 microns.

In various embodiments, a second therapeutic agent can be formulated together with Compound 1 to form a unitary or single dose form, for example, a tablet or capsule.

Dosage forms prepared as above can be subjected to in vitro dissolution evaluations according to Test 711 "Dissolution" in United States Pharmacopoeia 29, United States Pharmacopeial Convention, Inc., Rockville, Md., 2005 ("USP"), to determine the rate at which the active substance is released from the dosage forms. The content of active substance and the impurity levels are conveniently measured by techniques such as high performance liquid chromatography (HPLC).

In some embodiments, the invention includes use of packaging materials such as containers and closures of high-density polyethylene (HDPE), low-density polyethylene (LDPE) and or polypropylene and/or glass, glassine foil, aluminum pouches, and blisters or strips composed of aluminum or high-density polyvinyl chloride (PVC), optionally including a desiccant, polyethylene (PE), polyvinylidene dichloride (PVDC), PVC/PE/PVDC, and the like. These package materials can be used to store the various pharmaceutical compositions and formulations in a sterile fashion after appropriate sterilization of the package and its contents using chemical or physical sterilization techniques commonly employed in the pharmaceutical arts.

Methods for Administering the Pharmaceutical Compositions

In one aspect, the pharmaceutical compositions of the invention can be administered to a patient once daily or about every twenty four hours. Alternatively, the pharmaceutical compositions of the invention can be administered to a patient twice daily or about every twelve hours. These pharmaceutical compositions are administered as oral formulations containing about 25 mg, 50 mg, 100 mg, 125 mg, 150 mg, 200 mg, 250 mg, or 400 mg of Compound 1. In this aspect, in addition to Compound 1, the pharmaceutical compositions comprise a filler; a diluent; a disintegrant; a surfactant; at least one of a binder and a glidant; and a lubricant. For instance, a dose of 400 mg of Compound 1, may comprise two tablets of the invention each containing 200 mg of Compound 1, or four tablets of the invention each containing 100 mg of Compound 1.

It will also be appreciated that the compound and pharmaceutically acceptable compositions and formulations of the invention can be employed in combination therapies; that is, Compound 1 and pharmaceutically acceptable compositions thereof can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, for example, a CFTR mediated disease, or condition, are known as "appropriate for the disease or condition being treated."

In one embodiment, the additional therapeutic agent is selected from a mucolytic agent, bronchodialator, an antibiotic, an anti-infective agent, an anti-inflammatory agent, a CFTR modulator other than Compound 1 of the invention, or a nutritional agent.

In one embodiment, the additional agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide. In another embodiment, the additional agent is N-(5-hydroxy-2,4-di-tert-butyl-phenyl)-4-oxo-1H-quinoline-3-carboxamide. In another embodiment, the additional agent is selected from Table 1:

TABLE 1

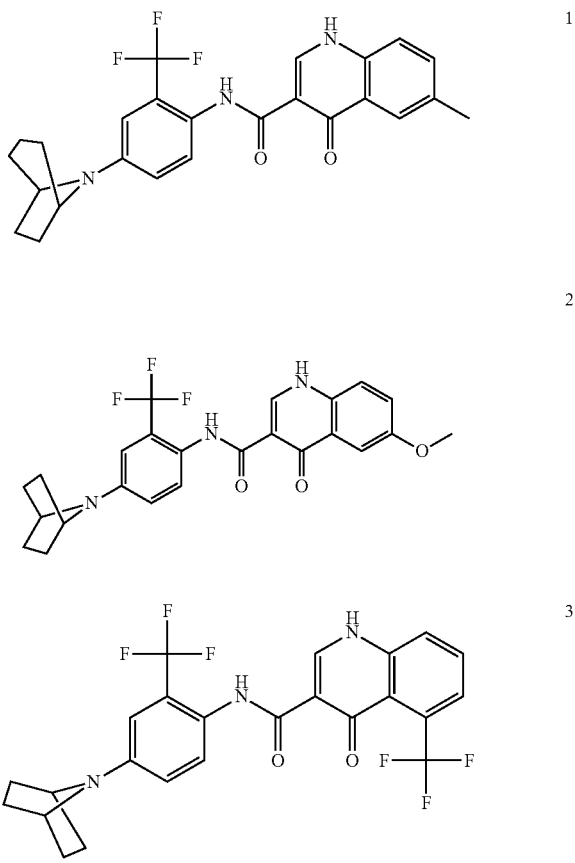

TABLE 1-continued
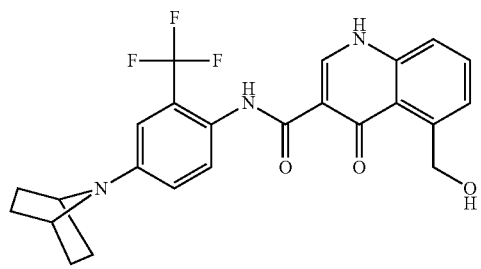 [SMILES: O=C(Nc1ccc(N2C3CCC2CC3)cc1C(F)(F)F)c1c[nH]c2cccc(CO)c2c1=O]
4
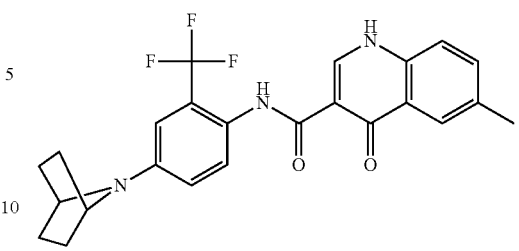
9
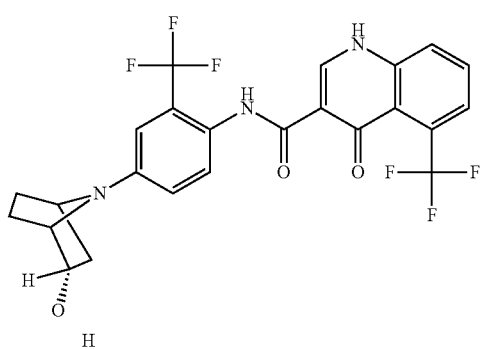
5
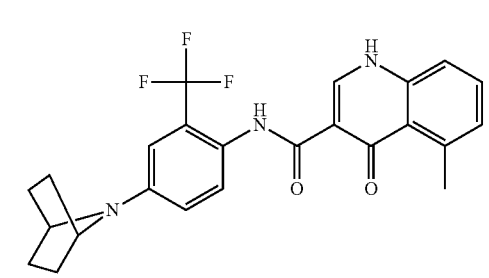
10
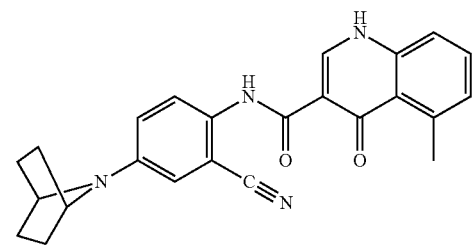 [SMILES: Cc1cccc2[nH]cc(C(=O)Nc3ccc(N4C5CCC4CC5)cc3C#N)c(=O)c12]
6
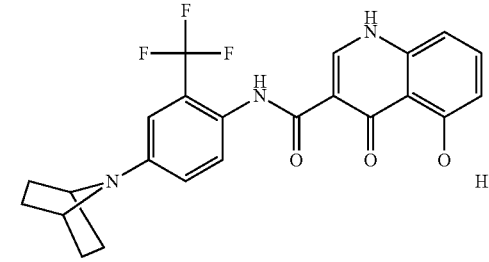
11
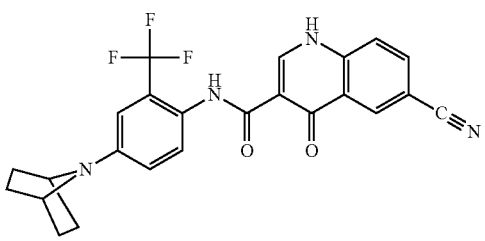 [SMILES: N#Cc1ccc2[nH]cc(C(=O)Nc3ccc(N4C5CCC4CC5)cc3C(F)(F)F)c(=O)c2c1]
7
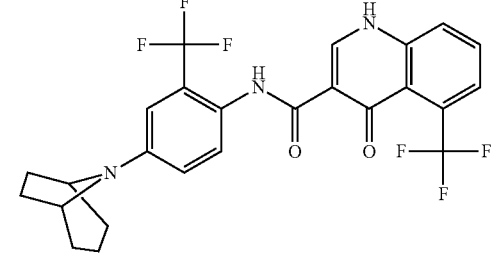
12
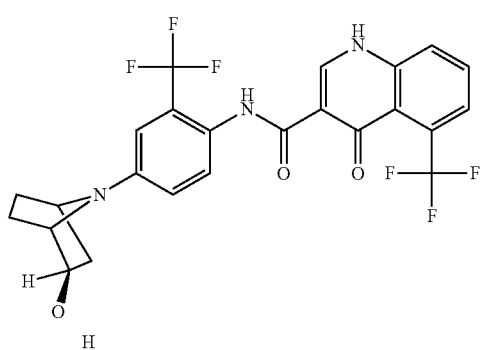
8
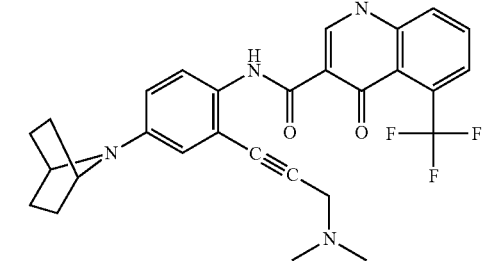
13

TABLE 1-continued

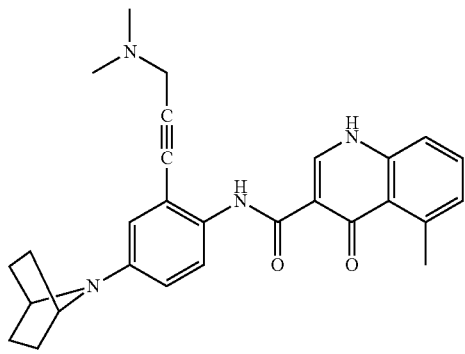 [SMILES: Cc1cccc2[nH]cc(C(=O)Nc3ccc(N4C5CCC4CC5)cc3C#CCN(C)C)c(=O)c12]

14

In another embodiment, the additional agent is any combination of the above agents. For example, the composition may comprise Compound 1, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, and N-(5-hydroxy-2,4-ditert-butyl-phenyl)-4-oxo-1H-quinoline-3-carboxamide. In another example, the composition may comprise Compound 1, N-(5-hydroxy-2,4-ditert-butyl-phenyl)-4-oxo-1H-quinoline-3-carboxamide, and any one of the compounds from Table 1, i.e. compounds 1 through 14 of Table 1, or any combination thereof.

In one embodiment, the additional therapeutic agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional agent is a mucolyte. Exemplary mucolytes useful herein includes Pulmozyme®.

In another embodiment, the additional agent is a bronchodialator. Exemplary bronchodialtors include albuterol, metaprotenerol sulfate, pirbuterol acetate, salmeterol, or tetrabuline sulfate.

In another embodiment, the additional agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[(3S,5R)-5-(4-amino-2-oxopyrimidin-1-yl)-3-hydroxyoxolan-2-yl]methoxy-hydroxyphosphoryl] [[[(2R,3 S,4R,5R)-5-(2,4-dioxopyrimidin-1-yl)-3, 4-dihydroxyoxolan-2-yl]methoxy-hydroxyphosphoryl]oxy-hydroxyphosphoryl] hydrogen phosphate), or bronchitol (inhaled formulation of mannitol).

In another embodiment, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In another embodiment, the additional agent is a CFTR modulator other than Compound 1, i.e., an agent that has the effect of modulating CFTR activity. Exemplary such agents include ataluren ("PTC124®"; 3-[5-(2-fluorophenyl)-1,2,4-oxadiazol-3-yl]benzoic acid), sinapultide, lancovutide, depelestat (a human recombinant neutrophil elastase inhibitor), and cobiprostone (7-{(2R, 4aR, 5R, 7aR)-2-[(3S)-1,1-difluoro-3-methylpentyl]-2-hydroxy-6-oxooctahydrocyclopenta[b]pyran-5-yl}heptanoic acid).

In another embodiment, the additional agent is a nutritional agent. Exemplary nutritional agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

In another embodiment, the additional agent is a compound selected from gentamicin, curcumin, cyclophosphamide, 4-phenylbutyrate, miglustat, felodipine, nimodipine, Philoxin B, geniestein, Apigenin, cAMP/cGMP modulators such as rolipram, sildenafil, milrinone, tadalafil, amrinone, isoproterenol, albuterol, and almeterol, deoxyspergualin, HSP 90 inhibitors, HSP 70 inhibitors, proteosome inhibitors such as epoxomicin, lactacystin, etc.

In other embodiments, the additional agent is a compound disclosed in WO 2004028480, WO 2004110352, WO 2005094374, WO 2005120497, or WO 2006101740. In another embodiment, the additional agent is a benzo[c]quinolizinium derivative that exhibits CFTR modulation activity or a benzopyran derivative that exhibits CFTR modulation activity. In another embodiment, the additional agent is a compound disclosed in U.S. Pat. Nos. 7,202,262, 6,992,096, US20060148864, US20060148863, US20060035943, US20050164973, WO2006110483, WO2006044456, WO2006044682, WO2006044505, WO2006044503, WO2006044502, or WO2004091502. In another embodiment, the additional agent is a compound disclosed in WO2004080972, WO2004111014, WO2005035514, WO2005049018, WO2006099256, WO2006127588, or WO2007044560. In another embodiment, the additional agent is N-(5-hydroxy-2,4-ditert-butyl-phenyl)-4-oxo-1H-quinoline-3-carboxamide.

In one embodiment, 400 mg of Compound 1 may be administered to a subject in need thereof followed by co-administration of 150 mg of N-(5-hydroxy-2,4-ditert-butyl-phenyl)-4-oxo-1H-quinoline-3-carboxamide (Compound 2). In another embodiment, 400 mg of Compound 1 may be administered to a subject in need thereof followed by co-administration of 250 mg of Compound 2. In these embodiments, the dosage amounts may be achieved by administration of one or more tablets of the invention. For example, administration of 400 mg of Compound 1 may be achieved by administering two tablets each containing 200 mg of Compound 1, or four tablets each containing 100 mg of Compound 1. Compound 2 may be administered as a pharmaceutical composition comprising Compound 2 and a pharmaceutically acceptable carrier. The duration of administration may continue until amelioration of the disease is achieved or until a subject's physician advises, e.g. duration of administration may be less than a week, 1 week, 2 weeks, 3 weeks, or a month or longer. The co-administration period may be preceded by an administration period of just Compound 1 alone. For example, there could be administration of 400 mg of Compound 1 for 2 weeks followed by co-administration of 150 mg or 250 mg of Compound 2 for 1 additional week.

In one embodiment, 400 mg of Compound 1 may be administered once a day to a subject in need thereof followed by co-administration of 150 mg of Compound 2 once a day. In another embodiment, 400 mg of Compound 1 may be administered once a day to a subject in need thereof followed by co-administration of 250 mg of Compound 2 once a day. In these embodiments, the dosage amounts may be achieved by administration of one or more tablets of the invention. For example, administration of 400 mg of Compound 1 may be achieved by administering two tablets each containing 200 mg of Compound 1, or four tablets each containing 100 mg of Compound 1. Compound 2 may be administered as a pharmaceutical composition comprising Compound 2 and a pharmaceutically acceptable carrier. The duration of administration may continue until amelioration of the disease is achieved or until a subject's physician advises, e.g. duration of administration may be less than a week, 1 week, 2 weeks, 3 weeks, or a month or longer. The co-administration period may be preceded by an administration period of just Compound 1 alone. For example, there could be administration of 400 mg of Compound 1 for 2 weeks followed by co-administration of 150 mg or 250 mg of Compound 2 for 1 additional week.

In one embodiment, 400 mg of Compound 1 may be administered once a day to a subject in need thereof followed by co-administration of 150 mg of Compound 2 every 12 hours. In another embodiment, 400 mg of Compound 1 may be administered once a day to a subject in need thereof followed by co-administration of 250 mg of Compound 2 every 12 hours. In these embodiments, the dosage amounts may be achieved by administration of one or more tablets of the invention. For example, administration of 400 mg of Compound 1 may be achieved by administering two tablets each containing 200 mg of Compound 1, or four tablets each containing 100 mg of Compound 1. Compound 2 may be administered as a pharmaceutical composition comprising Compound 2 and a pharmaceutically acceptable carrier. The duration of administration may continue until amelioration of the disease is achieved or until a subject's physician advises, e.g. duration of administration may be less than a week, 1 week, 2 weeks, 3 weeks, or a month or longer. The co-administration period may be preceded by an administration period of just Compound 1 alone. For example, there could be administration of 400 mg of Compound 1 for 2 weeks followed by co-administration of 150 mg or 250 mg of Compound 2 for 1 additional week.

These combinations are useful for treating the diseases described herein including cystic fibrosis. These combinations are also useful in the kits described herein.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Therapeutic Uses of the Composition

In certain embodiments, the pharmaceutically acceptable compositions comprising Compound 1 and optionally an additional agent are useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl$^-$ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508, as well as other mutations such as the G551D mutation, or the R117H mutation.

In one embodiment, Compound 1, as described herein, or pharmaceutically acceptable compositions thereof, are useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Tansmembrane Conductance Regulator Defects and Opportunities of Therapy*; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, Compound 1, as described herein, or pharmaceutically acceptable compositions thereof, are useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic insufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Anywhere in the present application where a name of a compound may not correctly describe the structure of the compound, the structure supersedes the name and governs.

EXAMPLES

XRPD (X-Ray Powder Diffraction)

The X-Ray diffraction (XRD) data of Compound 1, Compound 1 Form I, Compound 1 Form II, or Compound 1 HCl Salt Form A were collected on a Bruker D8 DISCOVER powder diffractometer with HI-STAR 2-dimensional detector and a flat graphite monochromator. Cu sealed tube with Kα radiation was used at 40 kV, 35 mA. The samples were placed on zero-background silicon wafers at 25° C. For each sample, two data frames were collected at 120 seconds each at 2 different θ2 angles: 8° and 26°. The data were integrated with GADDS software and merged with DIFFRACT$^{plus}$ EVA software. Uncertainties for the reported peak positions are ±0.2 degrees.

Jet Milling Description

Unmicronized Compound 1, Compound 1 Form I, Compound 1 Form II, or Compound 1 HCl Salt Form A is sieved to de-lump it prior to placing it into the jet mill hopper. All sieves are disposable and received a wipe prior to use. Unmicronized Compound 1, Compound 1 Form I, Compound 1 Form II, or Compound 1 HCl Salt Form A is added to the jet mill hopper at a controlled feeding rate using compressed nitrogen gas. The gas pressure range is 40-45/45-70 (Venturi/Mill) PSI and the feeding rate range is 0.5-1.6 Kg/Hour. The Compound 1, Compound 1 Form I, Compound 1 Form II, or Compound 1 HCl Salt Form A is micronized in the mill through particle-particle and particle-wall collisions and the processed Compound 1, Compound 1 Form I, Compound 1 Form II, or Compound 1 HCl Salt Form A is emptied into the micronized product containers. It is believed that one of ordinary skill in the art may also achieve Compound 1, Compound 1 Form I, Compound 1 Form II, or Compound 1 HCl Salt Form A with a favorable particle size through pin milling based in part on the conditions described above.

Differential Scanning Calorimetry (DSC)

The Differential scanning calorimetry (DSC) data of Compound 1, Compound 1 Form I, Compound 1 Form II, or Compound 1 HCl Salt Form A were collected using a DSC Q100 V9.6 Build 290 (TA Instruments, New Castle, Del.). Temperature was calibrated with indium and heat capacity was calibrated with sapphire. Samples of 3-6 mg were weighed into aluminum pans that were crimped using lids with 1 pin hole. The samples were scanned from 25° C. to 350° C. at a heating rate of 1.0° C./min and with a nitrogen gas purge of 50 ml/min. Data were collected by Thermal Advantage Q Series™ version 2.2.0.248 software and analyzed by Universal Analysis software version 4.1D (TA Instruments, New Castle, Del.). The reported numbers represent single analyses.

Compound 1 Form I, Compound 1 Form II, and Compound 1 HCl Salt Form a Single Crystal Structure Determination Diffraction data were acquired on Bruker Apex II diffractometer equipped with sealed tube Cu K-alpha source and an Apex II CCD detector. The structure was solved and refined using SHELX program (Sheldrick, G. M., Acta Cryst., (2008) A64, 112-122). Based on systematic absences and intensities statistics the structure was solved and refined in P2$_1$/n space group.

Vitride® (sodium bis(2-methoxyethoxy)aluminum hydride [or NaAlH$_2$(OCH$_2$CH$_2$OCH$_3$)2], 65 wgt % solution in toluene) was purchased from Aldrich Chemicals.

2,2-Difluoro-1,3-benzodioxole-5-carboxylic acid was purchased from Saltigo (an affiliate of the Lanxess Corporation).

Preparation of (2,2-difluoro-1,3-benzodioxol-5-yl)-methanol

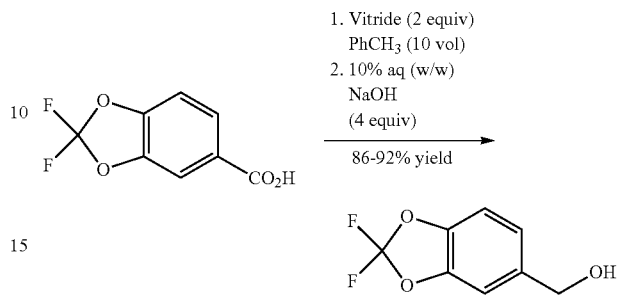

Commercially available 2,2-difluoro-1,3-benzodioxole-5-carboxylic acid (1.0 eq) was slurried in toluene (10 vol). Vitride® (2 eq) was added via addition funnel at a rate to maintain the temperature at 15-25° C. At the end of the addition, the temperature was increased to 40° C. for 2 hours (h), then 10% (w/w) aqueous (aq) NaOH (4.0 eq) was carefully added via addition funnel, maintaining the temperature at 40-50° C. After stirring for an additional 30 minutes (min), the layers were allowed to separate at 40° C. The organic phase was cooled to 20° C., then washed with water (2×1.5 vol), dried (Na$_2$SO$_4$), filtered, and concentrated to afford crude (2,2-difluoro-1,3-benzodioxol-5-yl)-methanol that was used directly in the next step.

Preparation of 5-chloromethyl-2,2-difluoro-1,3-benzodioxole

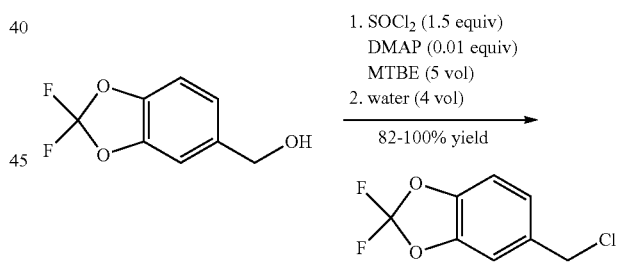

(2,2-difluoro-1,3-benzodioxol-5-yl)-methanol (1.0 eq) was dissolved in MTBE (5 vol). A catalytic amount of 4-(N,N-dimethyl)aminopyridine (DMAP) (1 mol %) was added and SOCl$_2$ (1.2 eq) was added via addition funnel. The SOCl$_2$ was added at a rate to maintain the temperature in the reactor at 15-25° C. The temperature was increased to 30° C. for 1 h, and then was cooled to 20° C. Water (4 vol) was added via addition funnel while maintaining the temperature at less than 30° C. After stirring for an additional 30 min, the layers were allowed to separate. The organic layer was stirred and 10% (w/v) aq NaOH (4.4 vol) was added. After stirring for 15 to 20 min, the layers were allowed to separate. The organic phase was then dried (Na$_2$SO$_4$), filtered, and concentrated to afford crude 5-chloromethyl-2,2-difluoro-1,3-benzodioxole that was used directly in the next step.

Preparation of (2,2-difluoro-1,3-benzodioxol-5-yl)-acetonitrile

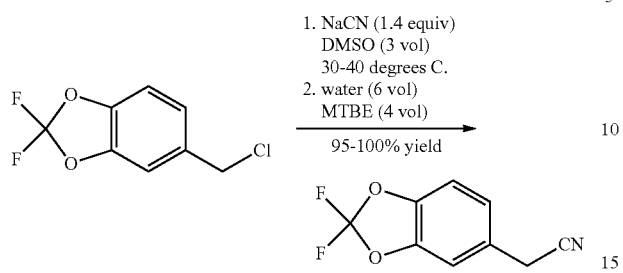

A solution of 5-chloromethyl-2,2-difluoro-1,3-benzodioxole (1 eq) in DMSO (1.25 vol) was added to a slurry of NaCN (1.4 eq) in DMSO (3 vol), while maintaining the temperature between 30-40° C. The mixture was stirred for 1 h, and then water (6 vol) was added, followed by methyl tert-butyl ether (MTBE) (4 vol). After stirring for 30 min, the layers were separated. The aqueous layer was extracted with MTBE (1.8 vol). The combined organic layers were washed with water (1.8 vol), dried (Na$_2$SO$_4$), filtered, and concentrated to afford crude (2,2-difluoro-1,3-benzodioxol-5-yl)-acetonitrile (95%) that was used directly in the next step.

Synthesis of (2,2-difluoro-1,3-benzodioxol-5-yl)-1-ethylacetate-acetonitrile

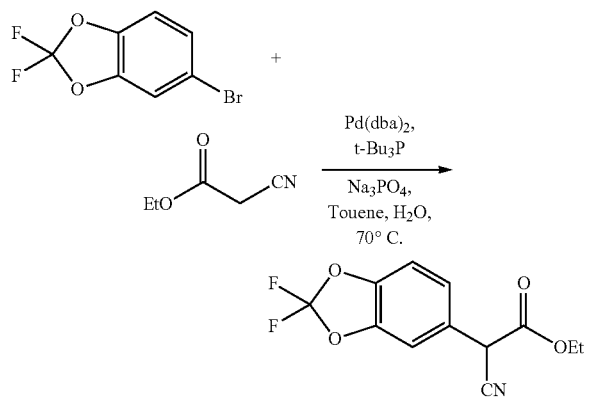

A reactor was purged with nitrogen and charged with 900 mL of toluene. The solvent was degassed via nitrogen sparge for no less than 16 h. To the reactor was then charged Na$_3$PO$_4$ (155.7 g, 949.5 mmol), followed by bis(dibenzylideneacetone) palladium (0) (7.28 g, 12.66 mmol). A 10% w/w solution of tert-butylphosphine in hexanes (51.23 g, 25.32 mmol) was charged over 10 min at 23° C. from a nitrogen purged addition funnel. The mixture was allowed to stir for 50 min, at which time 5-bromo-2,2-difluoro-1,3-benzodioxole (75 g, 316.5 mmol) was added over 1 min. After stirring for an additional 50 min, the mixture was charged with ethyl cyanoacetate (71.6 g, 633.0 mmol) over 5 min followed by water (4.5 mL) in one portion. The mixture was heated to 70° C. over 40 min and analyzed by HPLC every 1-2 h for the percent conversion of the reactant to the product. After complete conversion was observed (typically 100% conversion after 5-8 h), the mixture was cooled to 20-25° C. and filtered through a celite pad. The celite pad was rinsed with toluene (2×450 mL) and the combined organics were concentrated to 300 mL under vacuum at 60-65° C. The concentrate was charged with 225 mL DMSO and concentrated under vacuum at 70-80° C. until active distillation of the solvent ceased. The solution was cooled to 20-25° C. and diluted to 900 mL with DMSO in preparation for Step 2. $^1$H NMR (500 MHz, CDCl$_3$) δ 7.16-7.10 (m, 2H), 7.03 (d, J=8.2 Hz, 1H), 4.63 (s, 1H), 4.19 (m, 2H), 1.23 (t, J=7.1 Hz, 3H).

Synthesis of (2,2-difluoro-1,3-benzodioxol-5-yl)-acetonitrile

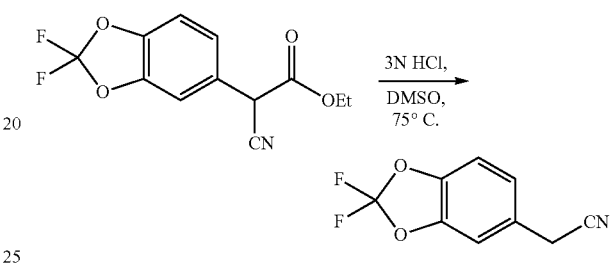

The DMSO solution of (2,2-difluoro-1,3-benzodioxol-5-yl)-1-ethylacetate-acetonitrile from above was charged with 3 N HCl (617.3 mL, 1.85 mol) over 20 min while maintaining an internal temperature<40° C. The mixture was then heated to 75° C. over 1 h and analyzed by HPLC every 1-2 h for % conversion. When a conversion of >99% was observed (typically after 5-6 h), the reaction was cooled to 20-25° C. and extracted with MTBE (2×525 mL), with sufficient time to allow for complete phase separation during the extractions. The combined organic extracts were washed with 5% NaCl (2×375 mL). The solution was then transferred to equipment appropriate for a 1.5-2.5 Torr vacuum distillation that was equipped with a cooled receiver flask. The solution was concentrated under vacuum at <60° C. to remove the solvents. (2,2-Difluoro-1,3-benzodioxol-5-yl)-acetonitrile was then distilled from the resulting oil at 125-130° C. (oven temperature) and 1.5-2.0 Torr. (2,2-Difluoro-1,3-benzodioxol-5-yl)-acetonitrile was isolated as a clear oil in 66% yield from 5-bromo-2,2-difluoro-1,3-benzodioxole (2 steps) and with an HPLC purity of 91.5% AUC (corresponds to a w/w assay of 95%). $^1$H NMR (500 MHz, DMSO) δ 7.44 (br s, 1H), 7.43 (d, J=8.4 Hz, 1H), 7.22 (dd, J=8.2, 1.8 Hz, 1H), 4.07 (s, 2H).

Preparation of (2,2-difluoro-1,3-benzodioxol-5-yl)-cyclopropanecarbonitrile

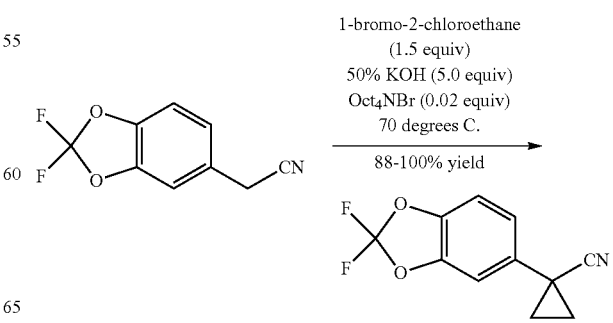

A mixture of (2,2-difluoro-1,3-benzodioxol-5-yl)-acetonitrile (1.0 eq), 50 wt % aqueous KOH (5.0 eq) 1-bromo-2-chloroethane (1.5 eq), and Oct₄NBr (0.02 eq) was heated at 70° C. for 1 h. The reaction mixture was cooled, then worked up with MTBE and water. The organic phase was washed with water and brine. The solvent was removed to afford (2,2-difluoro-1,3-benzodioxol-5-yl)-cyclopropanecarbonitrile.

Preparation of 1-(2,2-difluoro-1,3-benzodioxol-5-yl)-cyclopropanecarboxylic acid

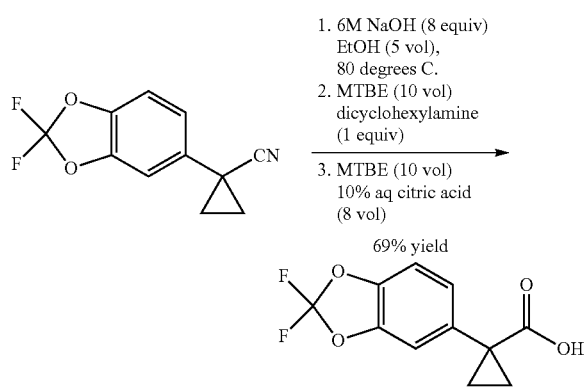

(2,2-difluoro-1,3-benzodioxol-5-yl)-cyclopropanecarbonitrile was hydrolyzed using 6 M NaOH (8 equiv) in ethanol (5 vol) at 80° C. overnight. The mixture was cooled to room temperature and the ethanol was evaporated under vacuum. The residue was taken up in water and MTBE, 1 M HCl was added, and the layers were separated. The MTBE layer was then treated with dicyclohexylamine (DCHA) (0.97 equiv). The slurry was cooled to 0° C., filtered and washed with heptane to give the corresponding DCHA salt. The salt was taken into MTBE and 10% citric acid and stirred until all the solids had dissolved. The layers were separated and the MTBE layer was washed with water and brine. A solvent swap to heptane followed by filtration gave 1-(2,2-difluoro-1,3-benzodioxol-5-yl)-cyclopropanecarboxylic acid after drying in a vacuum oven at 50° C. overnight.

Preparation of 1-(2,2-difluoro-1,3-benzodioxol-5-yl)-cyclopropanecarbonyl chloride

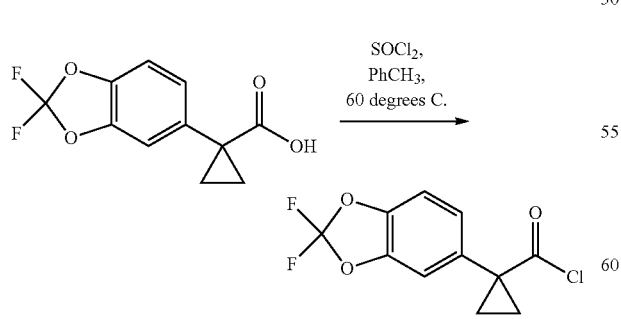

1-(2,2-difluoro-1,3-benzodioxol-5-yl)-cyclopropanecarboxylic acid (1.2 eq) is slurried in toluene (2.5 vol) and the mixture was heated to 60° C. SOCl₂ (1.4 eq) was added via addition funnel. The toluene and SOCl₂ were distilled from the reaction mixture after 30 minutes. Additional toluene (2.5 vol) was added and the resulting mixture was distilled again, leaving the product acid chloride as an oil, which was used without further purification.

Preparation of tert-butyl-3-(3-methylpyridin-2-yl)benzoate

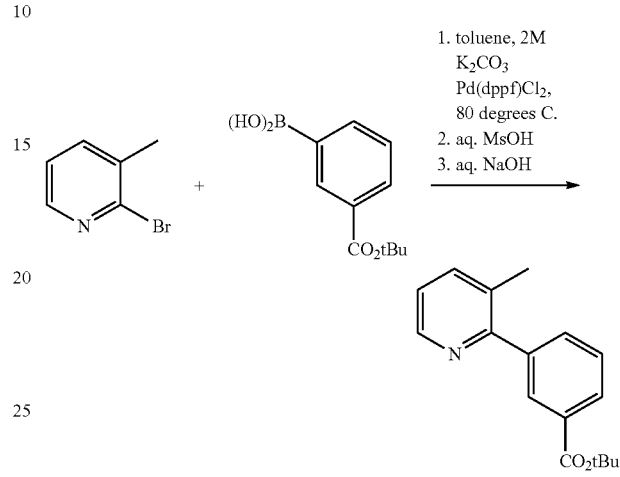

2-Bromo-3-methylpyridine (1.0 eq) was dissolved in toluene (12 vol). K₂CO₃ (4.8 eq) was added, followed by water (3.5 vol). The resulting mixture was heated to 65° C. under a stream of N₂ for 1 hour. 3-(t-Butoxycarbonyl)phenylboronic acid (1.05 eq) and Pd(dppf)Cl₂.CH₂Cl₂ (0.015 eq) were then added and the mixture was heated to 80° C. After 2 hours, the heat was turned off, water was added (3.5 vol), and the layers were allowed to separate. The organic phase was then washed with water (3.5 vol) and extracted with 10% aqueous methanesulfonic acid (2 eq MsOH, 7.7 vol). The aqueous phase was made basic with 50% aqueous NaOH (2 eq) and extracted with EtOAc (8 vol). The organic layer was concentrated to afford crude tert-butyl-3-(3-methylpyridin-2-yl)benzoate (82%) that was used directly in the next step.

Preparation of 2-(3-(tert-butoxycarbonyl)phenyl)-3-methylpyridine-1-oxide

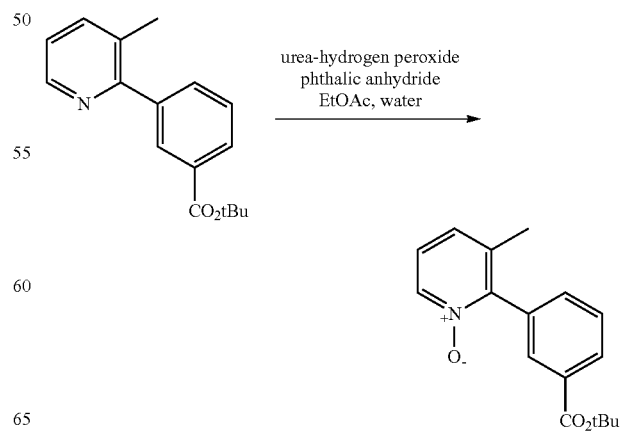

tert-Butyl-3-(3-methylpyridin-2-yl)benzoate (1.0 eq) was dissolved in EtOAc (6 vol). Water (0.3 vol) was added, followed by urea-hydrogen peroxide (3 eq). Phthalic anhydride (3 eq) was then added portionwise to the mixture as a solid at a rate to maintain the temperature in the reactor below 45° C. After completion of the phthalic anhydride addition, the mixture was heated to 45° C. After stirring for an additional 4 hours, the heat was turned off 10% w/w aqueous Na$_2$SO$_3$ (1.5 eq) was added via addition funnel. After completion of Na$_2$SO$_3$ addition, the mixture was stirred for an additional 30 min and the layers separated. The organic layer was stirred and 10% wt/wt aqueous. Na$_2$CO$_3$ (2 eq) was added. After stirring for 30 minutes, the layers were allowed to separate. The organic phase was washed 13% w/v aq NaCl. The organic phase was then filtered and concentrated to afford crude 2-(3-(tert-butoxycarbonyl)phenyl)-3-methylpyridine-1-oxide (95%) that was used directly in the next step.

Preparation of tert-butyl-3-(6-amino-3-methylpyridin-2-yl)benzoate

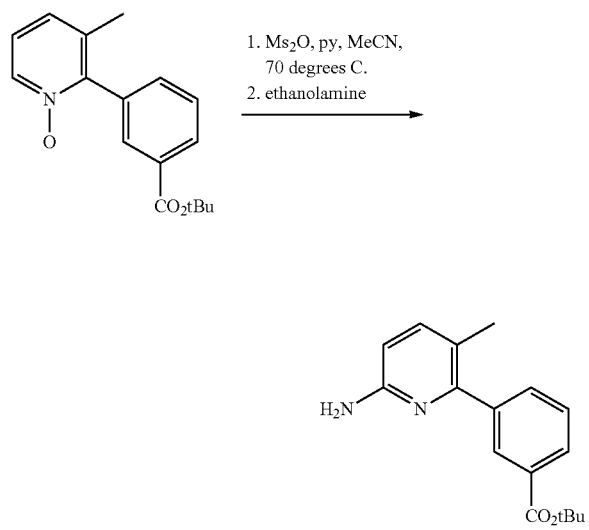

A solution of 2-(3-(tert-butoxycarbonyl)phenyl)-3-methylpyridine-1-oxide (1 eq) and pyridine (4 eq) in acetonitrile (8 vol) was heated to 70° C. A solution of methanesulfonic anhydride (1.5 eq) in MeCN (2 vol) was added over 50 min via addition funnel while maintaining the temperature at less than 75° C. The mixture was stirred for an additional 0.5 hours after complete addition. The mixture was then allowed to cool to ambient. Ethanolamine (10 eq) was added via addition funnel. After stirring for 2 hours, water (6 vol) was added and the mixture was cooled to 10° C. After stirring for 3 hours, the solid was collected by filtration and washed with water (3 vol), 2:1 acetonitrile/water (3 vol), and acetonitrile (2×1.5 vol). The solid was dried to constant weight (<1% difference) in a vacuum oven at 50° C. with a slight N$_2$ bleed to afford tert-butyl-3-(6-amino-3-methylpyridin-2-yl)benzoate as a red-yellow solid (53% yield).

Preparation of 3-(6-(1-(2,2-difluorobenzo[d][1,3]dioxol-5-yl)-cyclopropanecarboxamido)-3-methylpyridin-2-yl)-t-butylbenzoate

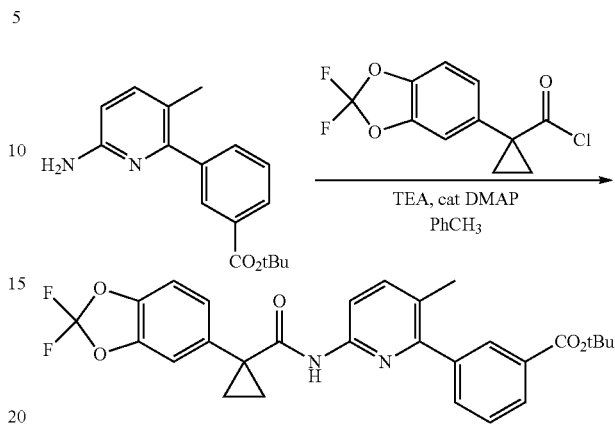

The crude acid chloride described above was dissolved in toluene (2.5 vol based on acid chloride) and added via addition funnel to a mixture of tert-butyl-3-(6-amino-3-methylpyridin-2-yl)benzoate (1 eq), DMAP, (0.02 eq), and triethylamine (3.0 eq) in toluene (4 vol based on tert-butyl-3-(6-amino-3-methylpyridin-2-yl)benzoate). After 2 hours, water (4 vol based on tert-butyl-3-(6-amino-3-methylpyridin-2-yl)benzoate) was added to the reaction mixture. After stirring for 30 minutes, the layers were separated. The organic phase was then filtered and concentrated to afford a thick oil of 3-(6-(1-(2,2-difluorobenzo[d][1,3]dioxol-5-yl) cyclopropanecarboxamido)-3-methylpyridin-2-yl)-t-butyl-benzoate (quantitative crude yield). Acetonitrile (3 vol based on crude product) was added and distilled until crystallization occurs. Water (2 vol based on crude product) was added and the mixture stirred for 2 h. The solid was collected by filtration, washed with 1:1 (by volume) acetonitrile/water (2×1 volumes based on crude product), and partially dried on the filter under vacuum. The solid was dried to a constant weight (<1% difference) in a vacuum oven at 60° C. with a slight N$_2$ bleed to afford 3-(6-(1-(2,2-difluorobenzo[d][1,3]dioxol-5-yl) cyclopropanecarboxamido)-3-methylpyridin-2-yl)-t-butylbenzoate as a brown solid.

Preparation of 3-(6-(1-(2,2-difluorobenzo[d][1,3]dioxol-5-yl) cyclopropanecarboxamido)-3-methylpyridin-2-yl)benzoic acid•HCL Salt

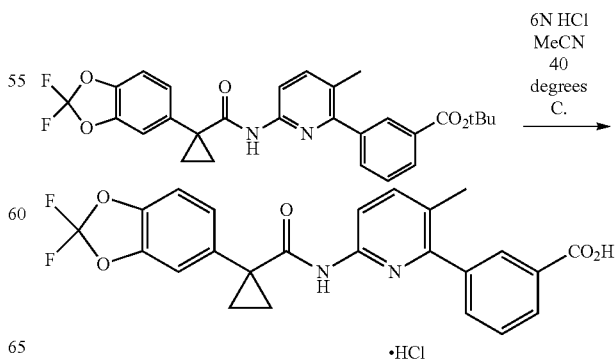

To a slurry of 3-(6-(1-(2,2-difluorobenzo[d][1,3]dioxol-5-yl) cyclopropanecarboxamido)-3-methylpyridin-2-yl)-t-butylbenzoate (1.0 eq) in MeCN (3.0 vol) was added water (0.83 vol) followed by concentrated aqueous HCl (0.83 vol). The mixture was heated to 45±5° C. After stirring for 24 to 48 h, the reaction was complete, and the mixture was allowed to cool to ambient. Water (1.33 vol) was added and the mixture stirred. The solid was collected by filtration, washed with water (2×0.3 vol), and partially dried on the filter under vacuum. The solid was dried to a constant weight (<1% difference) in a vacuum oven at 60° C. with a slight $N_2$ bleed to afford 3-(6-(1-(2,2-difluorobenzo[d][1,3]dioxol-5-yl) cyclopropanecarboxamido)-3-methylpyridin-2-yl)benzoic acid•HCl as an off-white solid.

An $^1$H NMR spectrum of Compound 1 is shown in FIG. 20 and FIG. 21 depicts an $^1$HNMR spectrum of Compound 1 as an HCl salt.

Table 2 below recites the $^1$H NMR data for Compound I.

TABLE 2

| Compound No | LC/MS M + 1 | LC/RT minutes | NMR |
|---|---|---|---|
| 1 | 453.3 | 1.93 | $^1$HNMR (400 MHz, DMSO-d6) 9.14 (s, 1H), 7.99-7.93 (m, 3H), 7.80-7.78 (m, 1H), 7.74-7.72 (m, 1H), 7.60-7.55 (m, 2H), 7.41-7.33 (m, 2H), 2.24 (s, 3H), 1.53-1.51 (m, 2H), 1.19-1.17 (m, 2H). |

Preparation of Compound 1 Form I, Method A.

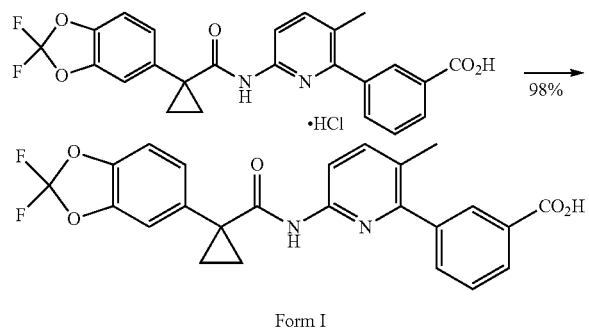

Form I

A slurry of 3-(6-(1-(2,2-difluorobenzo[d][1,3]dioxol-5-yl) cyclopropanecarboxamido)-3-methylpyridin-2-yl)benzoic acid•HCl (1 eq) in water (10 vol) was stirred at ambient temperature. A sample was taken after stirring for 24 h. The sample was filtered and the solid was washed with water (2 times). The solid sample was submitted for DSC analysis. When DSC analysis indicated complete conversion to Form I, the solid was collected by filtration, washed with water (2×1.0 vol), and partially dried on a filter under vacuum. The solid was then dried to a constant weight (<1% difference) in a vacuum oven at 60° C. with a slight $N_2$ bleed to afford Compound 1 Form I as an off-white solid (98% yield). $^1$H NMR (400 MHz, DMSO-d6) 9.14 (s, 1H), 7.99-7.93 (m, 3H), 7.80-7.78 (m, 1H), 7.74-7.72 (m, 1H), 7.60-7.55 (m, 2H), 7.41-7.33 (m, 2H), 2.24 (s, 3H), 1.53-1.51 (m, 2H), 1.19-1.17 (m, 2H).

Preparation of Compound 1 Form I, Method B.

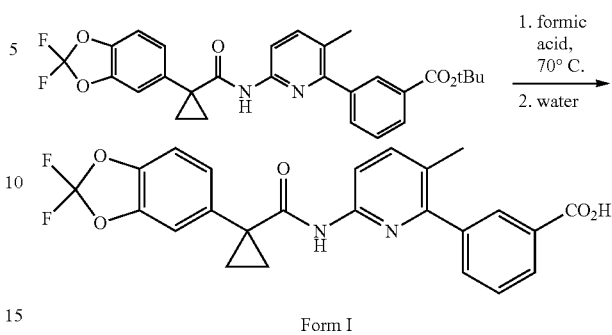

Form I

A solution of 3-(6-(1-(2,2-difluorobenzo[d][1,3]dioxol-5-yl) cyclopropanecarboxamido)-3-methylpyridin-2-yl)-t-butylbenzoate (1.0 eq) in formic acid (3.0 vol) was heated with stirring to 70±10° C., for 8 h. The reaction was deemed complete when no more than 1.0% AUC by chromatographic methods of 3-(6-(1-(2,2-difluorobenzo[d][1,3]dioxol-5-yl) cyclopropanecarboxamido)-3-methylpyridin-2-yl)-t-butylbenzoate) remained. The mixture was allowed to cool to ambient. The solution was added to water (6 vol), heated at 50° C., and the mixture was stirred. The mixture was then heated to 70±10° C. until the level of 3-(6-(1-(2,2-difluorobenzo[d][1,3]dioxol-5-yl) cyclopropanecarboxamido)-3-methylpyridin-2-yl)-t-butylbenzoate was no more than 0.8% (AUC). The solid was collected by filtration, washed with water (2×3 vol), and partially dried on the filter under vacuum. The solid was dried to a constant weight (<1% difference) in a vacuum oven at 60° C. with a slight $N_2$ bleed to afford Compound 1 Form I as an off-white solid.

The DSC trace of Compound 1 Form I is shown in FIG. 22. Melting for Compound 1 Form I occurs at about 204° C.

Figure 1:
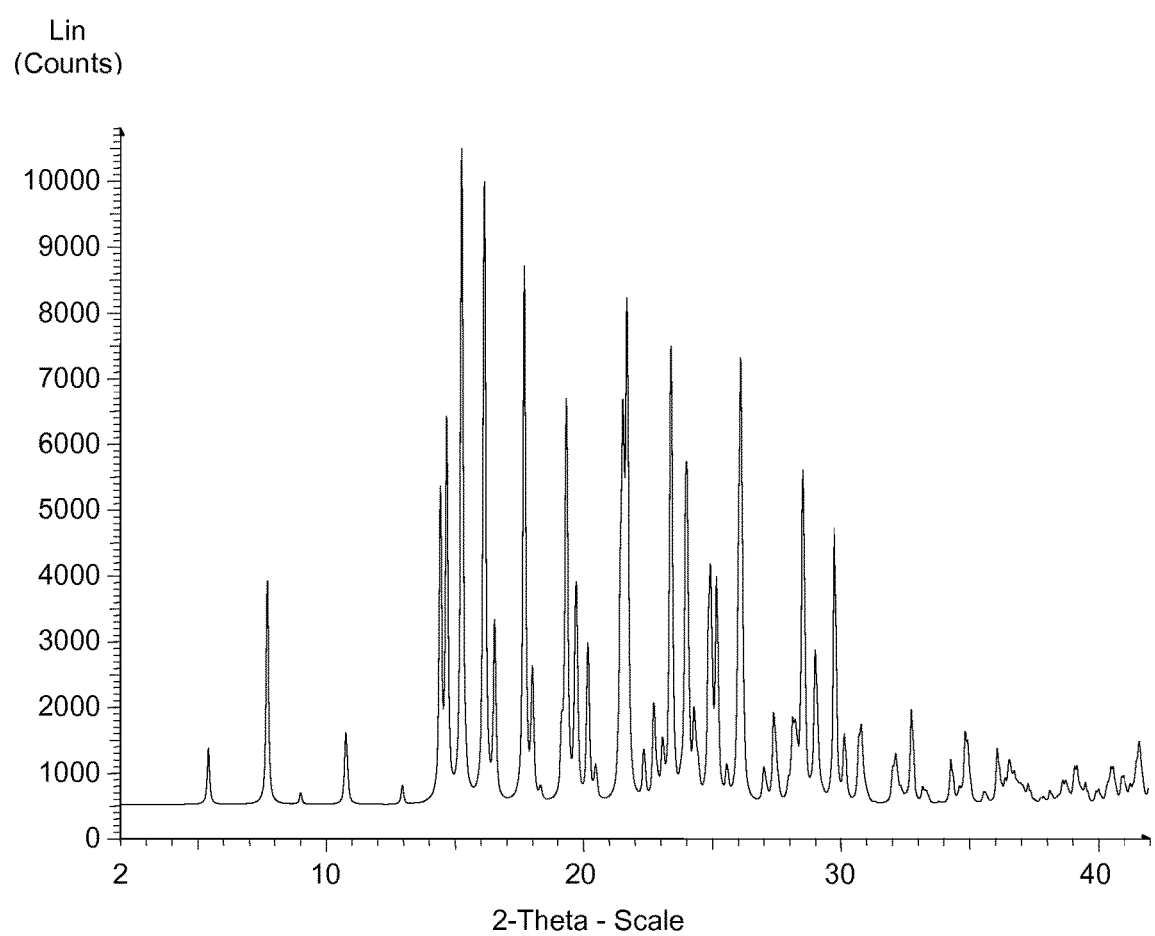
FIG. 1 is an X-ray diffraction pattern calculated from a single crystal structure of Compound 1 Form I.

An X-ray diffraction pattern was calculated from a single crystal structure of Compound 1 Form I and is shown in FIG. 1. Table 3 lists the calculated peaks for FIG. 1.

TABLE 3

| Peak Rank | 2θ Angle [degrees] | Relative Intensity [%] |
|---|---|---|
| 11 | 14.41 | 48.2 |
| 8 | 14.64 | 58.8 |
| 1 | 15.23 | 100.0 |
| 2 | 16.11 | 94.7 |
| 3 | 17.67 | 81.9 |
| 7 | 19.32 | 61.3 |
| 4 | 21.67 | 76.5 |
| 5 | 23.40 | 68.7 |
| 9 | 23.99 | 50.8 |
| 6 | 26.10 | 67.4 |
| 10 | 28.54 | 50.1 |

Figure 2:
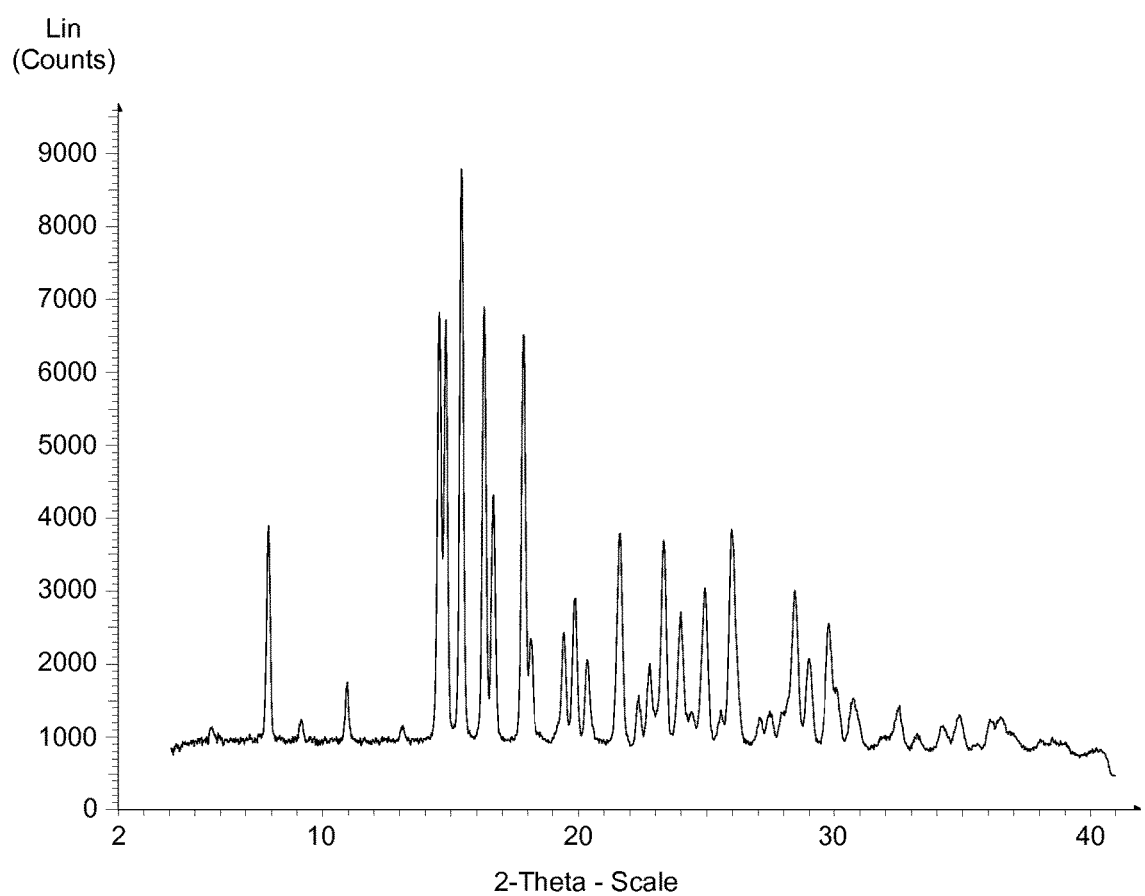
FIG. 2 is an actual X-ray powder diffraction pattern of Compound 1 Form I.

An actual X-ray powder diffraction pattern of Compound 1 Form I is shown in FIG. 2. Table 4 lists the actual peaks for FIG. 2.

TABLE 4

| Peak Rank | 2θ Angle [degrees] | Relative Intensity [%] |
|---|---|---|
| 7 | 7.83 | 37.7 |
| 3 | 14.51 | 74.9 |
| 4 | 14.78 | 73.5 |
| 1 | 15.39 | 100.0 |
| 2 | 16.26 | 75.6 |
| 6 | 16.62 | 42.6 |
| 5 | 17.81 | 70.9 |

TABLE 4-continued

| Peak Rank | 2θ Angle [degrees] | Relative Intensity [%] |
|---|---|---|
| 9 | 21.59 | 36.6 |
| 10 | 23.32 | 34.8 |
| 11 | 24.93 | 26.4 |
| 8 | 25.99 | 36.9 |

Colorless crystals of Compound 1 Form I were obtained by cooling a concentrated 1-butanol solution from 75° C. to 10° C. at a rate of 0.2° C./min. A crystal with dimensions of 0.50×0.08×0.03 mm was selected, cleaned with mineral oil, mounted on a MicroMount and centered on a Bruker APEXII system. Three batches of 40 frames separated in reciprocal space were obtained to provide an orientation matrix and initial cell parameters. Final cell parameters were obtained and refined based on the full data set.

A diffraction data set of reciprocal space was obtained to a resolution of 0.82 Å using 0.5° steps using 30 s exposure for each frame. Data were collected at 100 (2) K. Integration of intensities and refinement of cell parameters were accomplished using APEXII software. Observation of the crystal after data collection showed no signs of decomposition.

A conformational picture of Compound 1 Form I based on single crystal X-ray analysis is shown in FIG. 23. Compound 1 Form I is monoclinic, $P_2 1/n$, with the following unit cell dimensions: a=4.9626(7) Å, b=12.299(2) Å, c=33.075 (4) Å, β=93.938(9)°, V=2014.0 Å$^3$, Z=4. Density of Compound 1 Form I calculated from structural data is 1.492 g/cm$^3$ at 100 K.

Preparation of Compound 1 Form II from Compound 1 Form I.

Compound 1 Form I (approximately 30 mg) was slurried in 500 μL of an appropriate solvent (for example, methanol, ethanol, acetone, 2-propanol, acetonitrile, tetrahydrofuran, methyl acetate, 2-butanone, ethyl formate, and -methyl tetrahydrofuran for two days. The slurry was then filtered centrifugally or under vacuum and was left to dry at ambient temperature overnight to yield Compound 1 Form II.

The DSC trace of Compound 1 Form II Acetone Solvate is shown in FIG. 15, showing two phase transitions. The melting point for Compound 1 Form II Acetone Solvate occurs at about 188° C. and 205° C.

An actual X-ray powder diffraction pattern of Compound 1 Form II is shown in FIG. 3. Table 5 lists the actual peaks for FIG. 3 in descending order of relative intensity.

TABLE 5

| 2θ Angle [degrees] | Relative Intensity [%] |
|---|---|
| 21.70 | 100.0 |
| 8.98 | 65.5 |
| 11.04 | 57.4 |
| 18.16 | 55.9 |
| 23.06 | 55.4 |
| 20.63 | 53.1 |
| 22.22 | 50.2 |
| 18.57 | 49.1 |
| 16.66 | 47.2 |
| 19.86 | 35.0 |

Conformational depictions of Compound 1 Form II Acetone Solvate based on single crystal X-ray analysis are shown in FIG. 24. The stoichiometry between Compound 1 Form II and acetone is approximately 4.4:1 (4.48:1 calculated from $^1$H NMR; 4.38:1 from X-ray). The crystal structure reveals a packing of the molecules where there are two voids or pockets per unit cell, or 1 void per host molecule. In the acetone solvate, approximately 92 percent of voids are occupied by acetone molecules. Compound 1 Form II is a monoclinic P2$_1$/n space group with the following unit cell dimensions: a=16.5235(10) Å, b=12.7425(8) Å, c=20.5512 (13) Å, α=90°, β=103.736(4)°, γ=90°, V=4203.3(5) Å$^3$, =4. The density of Compound 1 in Compound 1 Form II calculated from structural data is 1.430/cm$^3$ at 100 K.

A solid state $^{13}$C NMR spectrum of Compound 1 Form II Acetone Solvate is shown in FIG. 25. Table 6 provides chemical shifts of the relevant peaks.

TABLE 6

| Compound 1 Form II, Acetone Solvate $^{13}$C Chem. Shifts | | |
|---|---|---|
| Peak # | F1 [ppm] | Intensity |
| 1 | 202.8 | 6.05 |
| 2 | 173.3 | 62.66 |
| 3 | 171.9 | 20.53 |
| 4 | 153.5 | 28.41 |
| 5 | 150.9 | 21.68 |
| 6 | 150.1 | 19.49 |
| 7 | 143.2 | 45.74 |
| 8 | 142.3 | 42.68 |
| 9 | 140.1 | 37.16 |
| 10 | 136.6 | 26.82 |
| 11 | 135.9 | 30.1 |
| 12 | 134.6 | 39.39 |
| 13 | 133.2 | 23.18 |
| 14 | 131.0 | 60.92 |
| 15 | 128.5 | 84.58 |
| 16 | 116.0 | 34.64 |
| 17 | 114.2 | 23.85 |
| 18 | 112.4 | 25.3 |
| 19 | 110.9 | 24.12 |
| 20 | 107.8 | 18.21 |
| 21 | 32.0 | 54.41 |
| 22 | 22.2 | 20.78 |
| 23 | 18.8 | 100 |

A solid state $^{19}$F NMR spectrum of Compound 1 Form II Acetone Solvate is shown in FIG. 26. Peaks with an asterisk denote spinning side bands. Table 7 provides chemical shifts of the relevant peaks.

TABLE 7

| Compound 1 Form II, Acetone Solvate $^{19}$F Chem. Shifts | | |
|---|---|---|
| Peak # | F1 [ppm] | Intensity |
| 1 | −41.6 | 12.5 |
| 2 | −46.4 | 6.77 |
| 3 | −51.4 | 9.05 |

Preparation of Compound 1 HCl Salt Form A.

Colorless crystals of Compound 1 HCl Salt Form A were obtained by slow evaporation from a concentrated solution of the HCl salt of Compound 1 in ethanol. A crystal with dimensions of 0.30×1/5×0.15 mm was selected, cleaned using mineral oil, mounted on a MicroMount and centered on a Bruker APEXII diffractometer. Three batches of 40 frames separated in reciprocal space were obtained to provide an orientation matrix and initial cell parameters. Final cell parameters were obtained and refined based on the full data set.

FIG. 18 provides a conformational image of Compound 1 HCl Salt Form A as a dimer, based on single crystal analysis. An X-ray diffraction pattern of Compound 1 HCl Salt Form A calculated from the crystal structure is shown in FIG. 27. Table 8 contains the calculated peaks for FIG. 27 in descending order of relative intensity.

TABLE 8

| 2θ [degrees] | Relative Intensity [%] |
|---|---|
| 8.96 | 100.00 |
| 17.51 | 48.20 |
| 18.45 | 34.60 |
| 10.33 | 32.10 |
| 16.01 | 18.90 |
| 11.94 | 18.40 |
| 8.14 | 16.20 |
| 10.10 | 13.90 |
| 16.55 | 13.30 |
| 9.54 | 10.10 |
| 16.55 | 13.30 |

Exemplary Oral Pharmaceutical Formulations Comprising Compound 1

A tablet was prepared with the components and amounts listed in Table 9 for Exemplary Tablet 1A comprising 100 mg of API, i.e. Compound 1 Form I. Exemplary Tablet 1A (formulated to have 100 mg of Compound 1) is prepared using a dry roller compaction device formulation process. In Table 9, grades/brands were microcrystalline cellulose: Avicel PH102; mannitol: Pearlitol SD 100; croscarmellose sodium: Acdisol; and colloidal silica: Cabosil.

TABLE 9

| | (% w/w) |
|---|---|
| Roller Compaction Granule Blend | |
| Compound 1 Form I | 30 |
| Microcrystalline cellulose | 42.3 |
| Mannitol | 21.2 |
| Croscarmellose Sodium | 3 |
| Sodium Lauryl Sulfate | 1 |
| Colloidal Silica | 0.5 |
| Magnesium Stearate | 2 |
| Tablet Composition (100 mg dose, 335 mg image) | |
| Roller Compaction Granule Blend | 99.5 |
| Magnesium Stearate | 0.5 |

A tablet was prepared with the components and amounts listed in Table 10 for Exemplary Tablet 1B comprising 100 mg of API, i.e. Compound 1 Form I. Exemplary Tablet 1B (formulated to have 100 mg of Compound 1 Form I) is prepared using a wet high shear granule formulation process. In Table 10, grades/brands were as follows. High Shear Granule Blend—microcrystalline cellulose: Avicel PH101; mannitol: Pearlitol C50; croscarmellose sodium: Acdisol; polyvinylpyrrolidone: Kollidon PVP K30; and in the Tablet Composition—croscarmellose sodium: Acdisol.

TABLE 10

| | (% w/w) |
|---|---|
| High Shear Granule Blend | |
| Compound 1 Form I | 50 |
| Microcrystalline cellulose | 30 |
| Mannitol | 13 |
| Croscarmellose Sodium | 2 |
| Polyvinylpyrrolidone | 4 |
| Sodium Lauryl Sulfate | 1 |
| Water (removed during drying) | 25-40% solids |
| Tablet Composition (100 mg dose, 205 mg image) | |
| High Shear Granule Blend | 97.5 |
| Croscarmellose Sodium | 2.0 |
| Magnesium Stearate | 0.5 |

A tablet was prepared with the components and amounts listed in Table 11 for Exemplary Tablet 1C comprising 100 mg of API, i.e. crystalline Compound 1 Form I. Exemplary Tablet 1C (formulated to have 100 mg of crystalline Compound 1 Form I) is prepared using a wet high shear granule formulation process. In Table 11, grades/brands were as follows. High Shear Granule Blend—microcrystalline cellulose: Avicel PH101; mannitol: Pearlitol C50; croscarmellose sodium: Acdisol; polyvinylpyrrolidone: Kollidon PVP K30; and in the Tablet Composition—croscarmellose sodium: Acdisol.

TABLE 11

| | (% w/w) |
|---|---|
| High Shear Granule Blend | |
| Compound 1 Form I | 60 |
| Microcrystalline cellulose | 20 |
| Mannitol | 13 |
| Croscarmellose Sodium | 2 |
| Polyvinylpyrrolidone | 4 |
| Sodium Lauryl Sulfate | 1 |
| Water (removed during drying) | 25-40% solids |
| Tablet Composition (100 mg dose, 171 mg image) | |
| High Shear Granule Blend | 97.5 |
| Croscarmellose Sodium | 2.0 |
| Magnesium Stearate | 0.5 |

A tablet was prepared with the components and amounts listed in Table 12 for Exemplary Tablet 1D comprising 200 mg of API, i.e. crystalline Compound 1 Form I. Exemplary Tablet 1D (formulated to have 200 mg of crystalline Compound 1 Form I) is prepared using a wet high shear granule formulation process. In Table 12, grades/brands were as follows. High Shear Granule Blend—microcrystalline cellulose: Avicel PH101; mannitol: Pearlitol C50; croscarmellose sodium: Acdisol; polyvinylpyrrolidone: Kollidon PVP K30; and in the Tablet Composition—microcrystalline cellulose: Avicel PH200; croscarmellose sodium: Acdisol; and magnesium stearate: 5712.

TABLE 12

| | (% w/w) |
|---|---|
| High Shear Granule Blend | |
| Compound 1 Form I | 60 |
| Microcrystalline cellulose | 20 |
| Mannitol | 13 |
| Croscarmellose Sodium | 2 |
| Polyvinylpyrrolidone | 4 |
| Sodium Lauryl Sulfate | 1 |
| Water (removed during drying) | 25-40% solids |
| Tablet Composition (200 mg dose, 402 mg image) | |
| High Shear Granule Blend | 83 |
| Microcrystalline cellulose | 14 |
| Croscarmellose Sodium | 2 |
| Magnesium Stearate | 1.0 |

A tablet was prepared with the components and amounts listed in Table 13 for Exemplary Tablet 1E comprising 200 mg of API, i.e. crystalline Compound 1 Form I. Exemplary Tablet 1E (formulated to have 200 mg of crystalline Compound 1 Form I) is prepared using a wet high shear granule formulation process. In Table 13, grades/brands were as follows. High Shear Granule Blend—microcrystalline cellulose: Avicel PH101; mannitol: Pearlitol C50; croscarmellose sodium: Acdisol; polyvinylpyrrolidone: Kollidon PVP K30; and in the Core Tablet Composition—microcrystalline cellulose: Avicel PH200; croscarmellose sodium: Acdisol; and magnesium stearate: 5712; and in the film coat—film coat: Opadry II; wax: Carnauba.

TABLE 13

| | mg |
|---|---|
| High Shear Granule Blend | |
| Compound 1 Form I | 200 |
| Microcrystalline cellulose | 66 |
| Mannitol | 43 |
| Croscarmellose Sodium | 7 |
| Polyvinylpyrrolidone | 13 |
| Sodium Lauryl Sulfate | 3 |
| Core Tablet Composition (200 mg dose, 400 mg image) | |
| High Shear Granule Blend | 332 |
| Microcrystalline cellulose | 56 |
| Croscarmellose Sodium | 8 |
| Magnesium Stearate | 4 |
| Film Coated Tablet (200 mg dose, 412 mg image) | |
| Core Tablet Composition | 400 |
| Film Coat | 12 |
| Wax | 0.04 |

A tablet was prepared with the components and amounts listed in Table 14 for Exemplary Tablet 1F comprising 200 mg of API, i.e. crystalline Compound 1 Form I. Exemplary Tablet 1F (formulated to have 200 mg of crystalline Compound 1 Form I) is prepared using a wet high shear granule formulation process. In Table 14, grades/brands were as follows. High Shear Granule Blend—microcrystalline cellulose: Avicel PH101; mannitol: Pearlitol C50; croscarmellose sodium: Acdisol; polyvinylpyrrolidone: Kollidon PVP K30; and in the Core Tablet Composition—microcrystalline cellulose: Avicel PH200; croscarmellose sodium: Acdisol; and magnesium stearate: 5712; and in the film coat—film coat: Opadry II; wax: Carnauba.

TABLE 14

| | mg |
|---|---|
| High Shear Granule Blend | |
| Compound 1 Form I | 200 |
| Microcrystalline cellulose | 67 |
| Mannitol | 45 |
| Croscarmellose Sodium | 7 |
| Polyvinylpyrrolidone | 10.4 |
| Sodium Lauryl Sulfate | 2.6 |
| Core Tablet Composition (200 mg dose, 400 mg image) | |
| High Shear Granule Blend | 332 |
| Microcrystalline cellulose | 56 |
| Croscarmellose Sodium | 8 |
| Magnesium Stearate | 4 |
| Film Coated Tablet (200 mg dose, 412 mg image) | |
| Core Tablet Composition | 400 |
| Film Coat | 12 |
| Wax | 0.04 |

A tablet was prepared with the components and amounts listed in Table 15 for Exemplary Tablet 1G comprising 100 mg of API, i.e. crystalline Compound 1 Form I. Exemplary Tablet 1G (formulated to have 100 mg of crystalline Compound 1 Form I) is prepared using a wet high shear granule formulation process. In Table 15, grades/brands were as follows. High Shear Granule Blend—microcrystalline cellulose: Avicel PH101; mannitol: Pearlitol C50; croscarmellose sodium: Acdisol; polyvinylpyrrolidone: Kollidon PVP K30; and in the Tablet Composition—croscarmellose sodium: Acdisol.

TABLE 15

| | (% w/w) |
|---|---|
| High Shear Granule Blend | |
| Compound 1 Form I | 70 |
| Microcrystalline cellulose | 12 |
| Mannitol | 11 |
| Croscarmellose Sodium | 2 |
| Polyvinylpyrrolidone | 4 |
| Sodium Lauryl Sulfate | 1 |
| Water (removed during drying) | 25-40% solids |
| Tablet Composition (100 mg dose, 147 mg image) | |
| High Shear Granule Blend | 97.5 |
| Croscarmellose Sodium | 2.0 |
| Magnesium Stearate | 0.5 |

A tablet was prepared with the components and amounts listed in Table 16 for Exemplary Tablet 1H comprising 100 mg of API, i.e. crystalline Compound 1 Form I or Form II. Exemplary Tablet 1H (formulated to have 100 mg of crystalline Compound 1 Form I or Form II) is prepared using a wet high shear granule formulation process. In Table 16, grades/brands were as follows. High Shear Granule Blend—microcrystalline cellulose: Avicel PH101; mannitol: Pearlitol C50; croscarmellose sodium: Acdisol; polyvinylpyrrolidone: Kollidon PVP K30; and in the Core Tablet Composition—microcrystalline cellulose: Avicel PH200; croscarmellose sodium: Acdisol; and magnesium stearate: 5712.

TABLE 16

| | (% w/w) |
|---|---|
| High Shear Granule Blend | |
| Compound 1 Form I or Form II | 61 |
| Microcrystalline cellulose | 20.3 |
| Mannitol | 13.2 |
| Croscarmellose Sodium | 2 |
| Polyvinylpyrrolidone | 2.7 |
| Sodium Lauryl Sulfate | 0.7 |
| Tablet Composition (100 mg dose, 197 mg image) | |
| High Shear Granule Blend | 83 |
| Microcrystalline cellulose | 14 |
| Croscarmellose Sodium | 2 |
| Magnesium Stearate | 1 |

A tablet was prepared with the components and amounts listed in Table 17 for Exemplary Tablet 1I comprising 100 mg of API, i.e. crystalline Compound 1 Form I or Form II. Exemplary Tablet 1I (formulated to have 100 mg of crystalline Compound 1 Form I or Form II) is prepared using a wet high shear granule formulation process. In Table 17, grades/brands were as follows. High Shear Granule Blend—microcrystalline cellulose: Avicel PH101; mannitol: Pearlitol C50; croscarmellose sodium: Acdisol; polyvinylpyrrolidone: Kollidon PVP K30; and in the Core Tablet Composition—microcrystalline cellulose: Avicel PH200; croscarmellose sodium: Acdisol; and magnesium stearate: 5712.

TABLE 17

| | mg |
|---|---|
| High Shear Granule Blend | |
| Compound 1 Form I or Form II | 100 |
| Microcrystalline cellulose | 33.3 |
| Mannitol | 21.7 |
| Croscarmellose Sodium | 3.3 |
| Polyvinylpyrrolidone | 4.4 |
| Sodium Lauryl Sulfate | 1.1 |
| Core Tablet Composition (100 mg dose, 197 mg image) | |
| High Shear Granule Blend | 163.9 |
| Microcrystalline cellulose | 27.6 |
| Croscarmellose Sodium | 3.9 |
| Magnesium Stearate | 2.0 |

Tablet Formation from Roller Compaction Granule Composition

Equipment/Process

Equipment

Roller Compactors: Alexanderwerk WP 120, Vector TF-Mini, or Vector TF-Labo.

Screening/Weighing

Compound 1 and excipients may be screened prior to or after weigh-out. Appropriate screen sizes are mesh 20, mesh 40, or mesh 60. Compound 1 may be pre-blended with one or more of the excipients to simplify screening.

Blending

Compound 1 and excipients may be added to the blender in different order. The blending may be performed in a Turbula blender or a v-shell blender. The components may be blended for 10 minutes without lubricant followed by additional blending with lubricant for 3 minutes.

Roller Compaction

The blend may be roller compacted in ribbons and milled into granules using an Alexanderwerk WP 120. The rolls used may be the 25 mm rolls using a compaction pressure of 18 to 50 bar, a roller speed of 3 to 12 RPM, and a screw feeder speed of 20 to 80 RPM. The screen sizes of the integrated mill may be 2 mm for the top screen and 0.8 mm for the bottom screen.

Blending

The roller compacted granules may be blended with extra-granular excipients such as fillers and lubricant using a V-shell blender. The blending time may be 5, 3 or 1 minute(s).

Compression

The compression blend has been compressed into tablets using a single station Riva MiniPress with 10 mm tooling. The weight of the tablets for a 100 mg dose may be about 200, 250, or 300 mg.

Film Coating

Tablets may be film coated using a pan coater, such as, for example an O'Hara Labcoat.

Printing

Film coated tablets may be printed with a monogram on one or both tablet faces with, for example, a Hartnett Delta printer.

Tablet Formation from High Shear Granule Composition

Equipment/Process

Equipment

Granulator: Procept MiPro with a 250 ml or 1 L granulation bowl.

Screening/Weighing

Compound 1 and excipients may be screened prior to or after weigh-out. Possible screen sizes are mesh 20, mesh 40, or mesh 60. Compound 1 may be pre-blended with one or more of the excipients to simplify screening.

Granulation Operation

Granulation Fluid—SLS and binder are added to purified water and mixed until dissolved. A suitable ratio is 2.5% w/w SLS and 10.0% w/w PVP K30 in water.

Granulation—The excipients and compound 1 are added to the granulation bowl. The order of addition may be Compound 1, disintegrant, diluent, and filler. The components may be mixed in the 250 ml bowl for 1 minute at impeller speed 1000 RPM and chopper speed 1000 RPM. Granulation may be performed at an impeller speed of 2000 RPM with a chopper speed of 4000 RPM while adding the granulation fluid with a syringe pump at 1.5 to 4.5 g/min. The fluid addition time may be 4 to 12 minutes. After the required binder fluid is added, the granules may be wet-massed for about 10 seconds to about 1 minute. One notable advantage of the present high shear granulation process is using a granulation fluid that comprises both a surfactant and the binder for better granulation through increased wettability. In one embodiment, the surfactant is SLS.

Drying

The granules may be dried using a vacuum oven, tray dryer, bi-conical dryer, or fluid bed drier. The granules have been dried using a vacuum oven with a nitrogen purge.

Blending

The granules may be blended with extra-granular excipients. The granules have been blended with extra-granular disintegrant, diluent, filler, and lubricant. The granules have been blended using the Turbula blender for 3 minutes pre-lubricant and 1 minute with lubricant. A larger scale blender such as a 4-quart V-shell blender may be used.

Compression

The compression blend has been compressed into tablets using a single station Riva MiniPress with 8 mm, or 10 mm tooling. The weight of the tablets for a 100 mg dose may be about 160, 200, or 250 mg.

Film Coating

Tablets may be film coated using a pan coater, such as, for example an O'Hara Labcoat.

Printing

Film coated tablets may be printed with a monogram on one or both tablet faces with, for example, a Hartnett Delta printer.

Dosing Administration Schedule

In another aspect, the invention relates to a method of treating a CFTR mediated disease in a subject comprising administering to a subject in need thereof an effective amount of the pharmaceutical composition provided by the invention. In another embodiment, the pharmaceutical composition is administered to the subject once every two weeks. In another embodiment, the pharmaceutical composition is administered to the subject once a week. In another embodiment, the pharmaceutical composition is administered to the subject once every three days. In another embodiment, the pharmaceutical composition is administered to the subject once a day. In one embodiment, when the pharmaceutical composition is a tablet according to Table 9, 10, 11, 12, 13, 14, 15, 16, or 17 dosing is once a day.

Assays

Assays for Detecting and Measuring ΔF508-CFTR Correction Properties of Compounds Membrane potential optical methods for assaying ΔF508-CFTR modulation properties of compounds.

The optical membrane potential assay utilized voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, $DiSBAC_2(3)$, and a fluorescent phospholipid, CC2-DMPE, which is attached to the outer leaflet of the plasma membrane and acts as a FRET donor. Changes in membrane potential ($V_m$) cause the negatively charged $DiSBAC_2(3)$ to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

1. Identification of Correction Compounds

To identify small molecules that correct the trafficking defect associated with ΔF508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ΔF508-CFTR. The cells were subsequently rinsed 3× with Krebs Ringers solution and loaded with the voltage-sensitive dyes. To activate ΔF508-CFTR, 10 μM forskolin and the CFTR potentiator, genistein (20 μM), were added along with $Cl^-$-free medium to each well. The addition of $Cl^-$-free medium promoted $Cl^-$ efflux in response to ΔF508-CFTR activation and the resulting membrane depolarization was optically monitored using the FRET-based voltage-sensor dyes.

2. Identification of Potentiator Compounds

To identify potentiators of ΔF508-CFTR, a double-addition HTS assay format was developed. During the first addition, a $Cl^-$-free medium with or without test compound was added to each well. After 22 sec, a second addition of $Cl^-$-free medium containing 2-10 μM forskolin was added to activate ΔF508-CFTR. The extracellular $Cl^-$ concentration following both additions was 28 mM, which promoted $Cl^-$ efflux in response to ΔF508-CFTR activation and the resulting membrane depolarization was optically monitored using the FRET-based voltage-sensor dyes.

3. Solutions

Bath Solution #1: (in mM) NaCl 160, KCl 4.5, $CaCl_2$ 2, $MgCl_2$ 1, HEPES 10, pH 7.4 with NaOH.

Chloride-free bath solution: Chloride salts in Bath Solution #1 are substituted with gluconate salts.

CC2-DMPE: Prepared as a 10 mM stock solution in DMSO and stored at −20° C. $DiSBAC_2(3)$: Prepared as a 10 mM stock in DMSO and stored at −20° C.

4. Cell Culture

NIH3T3 mouse fibroblasts stably expressing ΔF508-CFTR are used for optical measurements of membrane potential. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For all optical assays, the cells were seeded at 30,000/well in 384-well matrigel-coated plates and cultured for 2 hrs at 37° C. before culturing at 27° C. for 24 hrs for the potentiator assay. For the correction assays, the cells are cultured at 27° C. or 37° C. with and without compounds for 16-24 hours.

Electrophysiological Assays for Assaying ΔF508-CFTR Modulation Properties of Compounds 1. Using Chamber Assay Using chamber experiments were performed on polarized epithelial cells expressing ΔF508-CFTR to further characterize the ΔF508-CFTR modulators identified in the optical assays. $FRT^{\Delta F508-CFTR}$ epithelial cells grown on Costar Snapwell cell culture inserts were mounted in an Using chamber (Physiologic Instruments, Inc., San Diego, Calif.), and the monolayers were continuously short-circuited using a Voltage-clamp System (Department of Bioengineering, University of Iowa, Iowa, and, Physiologic Instruments, Inc., San Diego, Calif.). Transepithelial resistance was measured by applying a 2-mV pulse. Under these conditions, the FRT epithelia demonstrated resistances of 4 $K\Omega/cm^2$ or more. The solutions were maintained at 27° C. and bubbled with air. The electrode offset potential and fluid resistance were corrected using a cell-free insert. Under these conditions, the current reflects the flow of $Cl^-$ through ΔF508-CFTR expressed in the apical membrane. The $I_{SC}$ was digitally acquired using an MP100A-CE interface and Acq-Knowledge software (v3.2.6; BIOPAC Systems, Santa Barbara, Calif.).

2. Identification of Correction Compounds

Typical protocol utilized a basolateral to apical membrane $Cl^-$ concentration gradient. To set up this gradient, normal ringer was used on the basolateral membrane, whereas apical NaCl was replaced by equimolar sodium gluconate (titrated to pH 7.4 with NaOH) to give a large concentration gradient across the epithelium. All experiments were performed with intact monolayers. To fully activate ΔF508-CFTR, forskolin (10 μM) and the PDE inhibitor, IBMX (100 μM), were applied followed by the addition of the CFTR potentiator, genistein (50 μM).

As observed in other cell types, incubation at low temperatures of FRT cells stably expressing ΔF508-CFTR increases the functional density of CFTR in the plasma membrane. To determine the activity of correction compounds, the cells were incubated with 10 μM of the test compound for 24 hours at 37° C. and were subsequently washed 3× prior to recording. The cAMP- and genistein-mediated $I_{SC}$ in compound-treated cells was normalized to the 27° C. and 37° C. controls and expressed as percentage activity. Preincubation of the cells with the correction compound significantly increased the cAMP- and genistein-mediated $I_{SC}$ compared to the 37° C. controls.

3. Identification of Potentiator Compounds

Typical protocol utilized a basolateral to apical membrane $Cl^-$ concentration gradient. To set up this gradient, normal ringers was used on the basolateral membrane and was permeabilized with nystatin (360 μg/ml), whereas apical NaCl was replaced by equimolar sodium gluconate (titrated to pH 7.4 with NaOH) to give a large $Cl^-$ concentration gradient across the epithelium. All experiments were performed 30 min after nystatin permeabilization. Forskolin (10 μM) and all test compounds were added to both sides of the cell culture inserts. The efficacy of the putative ΔF508-CFTR potentiators was compared to that of the known potentiator, genistein.

4. Solutions

Basolateral solution (in mM): NaCl (135), $CaCl_2$ (1.2), $MgCl_2$ (1.2), $K_2HPO_4$ (2.4), $KHPO_4$ (0.6), N-2-hydroxyethylpiperazine-N'-2-ethanesulfonic acid (HEPES) (10), and dextrose (10). The solution was titrated to pH 7.4 with NaOH.

Apical solution (in mM): Same as basolateral solution with NaCl replaced with Na Gluconate (135).

5. Cell Culture

Fisher rat epithelial (FRT) cells expressing ΔF508-CFTR (FRT$^{\Delta F508\text{-}CFTR}$) were used for Using chamber experiments for the putative ΔF508-CFTR modulators identified from our optical assays. The cells were cultured on Costar Snapwell cell culture inserts and cultured for five days at 37° C. and 5% $CO_2$ in Coon's modified Ham's F-12 medium supplemented with 5% fetal calf serum, 100 U/ml penicillin, and 100 µg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

6. Whole-Cell Recordings

The macroscopic ΔF508-CFTR current ($I_{\Delta F508}$) in temperature- and test compound-corrected NIH3T3 cells stably expressing ΔF508-CFTR were monitored using the perforated-patch, whole-cell recording. Briefly, voltage-clamp recordings of $I_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl⁻ ($E_{Cl}$) at room temperature was −28 mV. All recordings had a seal resistance>20 GΩ and a series resistance<15 M. Pulse generation, data acquisition, and analysis were performed using a PC equipped with a Digidata 1320 A/D interface in conjunction with Clampex 8 (Axon Instruments Inc.). The bath contained<250 µl of saline and was continuously perifused at a rate of 2 ml/min using a gravity-driven perfusion system, 7. Identification of Correction Compounds To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 µM forskolin and 20 µM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 µM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 µM of correction compounds significantly increased the cAMP- and genistein-dependent current compared to the 37° C. controls.

8. Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

9. Solutions

Intracellular solution (in mM): Cs-aspartate (90), CsCl (50), $MgCl_2$ (1), HEPES (10), and 240 µg/ml amphotericin-B (pH adjusted to 7.35 with CsOH).

Extracellular solution (in mM): N-methyl-D-glucamine (NMDG)-Cl (150), $MgCl_2$ (2), $CaCl_2$ (2), HEPES (10) (pH adjusted to 7.35 with HCl).

10. Cell Culture

NIH3T3 mouse fibroblasts stably expressing ΔF508-CFTR are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

11. Single-Channel Recordings

The single-channel activities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1-2 sec. To maintain ΔF508-CFTR activity during the rapid perifusion, the nonspecific phosphatase inhibitor F⁻ (10 mM NaF) was added to the bath solution. Under these recording conditions, channel activity remained constant throughout the duration of the patch recording (up to 60 min). Currents produced by positive charge moving from the intra to extracellular solutions (anions moving in the opposite direction) are shown as positive currents. The pipette potential ($V_p$) was maintained at 80 mV.

Channel activity was analyzed from membrane patches containing ≤2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o = I/i(N)$, where I=mean current, i=single-channel current amplitude, and N=number of active channels in patch.

12. Solutions

Extracellular solution (in mM): NMDG (150), aspartic acid (150), $CaCl_2$ (5), $MgCl_2$ (2), and HEPES (10) (pH adjusted to 7.35 with Tris base).

Intracellular solution (in mM): NMDG-Cl (150), $MgCl_2$ (2), EGTA (5), TES (10), and Tris base (14) (pH adjusted to 7.35 with HCl).

13. Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

Using the procedures described above, the activity, i.e., EC50s, of Compound 1 has been measured and is shown in Table 18.

TABLE 18

| IC50/EC50 Bins: +++ <= 2.0 < ++ <= 5.0 < + | | |
| PercentActivity Bins: + <= 25.0 < ++ <= 100.0 < +++ | | |
|---|---|---|
| Cmpd. No. | BinnedEC50 | BinnedMaxEfficacy |
| 1 | +++ | +++ |

OTHER EMBODIMENTS

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the invention. One skilled in the art will readily recognize from such discussion and from the accompanying drawings and claims, that various changes, modifications and variations can be made therein without departing from the spirit and scope of the invention as defined in the following claims.

The invention claimed is:

1. A tablet for oral administration comprising:
   a. 3-(6-(1-(2,2-difluorobenzo[d][1,3]dioxol-5-yl)cyclopropanecarboxamido)-3-methylpyridin-2-yl)benzoic acid (Compound 1) Form I wherein the Compound 1 Form I is present in an amount ranging from 25 mg to 250 mg;
   b. a filler;
   c. a disintegrant;
   d. a surfactant;
   e. a lubricant; and
   f. a binder which is polyvinylpyrrolidone.

2. A tablet for oral administration comprising:
   a. 3-(6-(1-(2,2-difluorobenzo[d][1,3]dioxol-5-yl)cyclopropanecarboxamido)-3-methylpyridin-2-yl)benzoic acid (Compound 1) Form I wherein the Compound 1 Form I is present in an amount ranging from 25 mg to 250 mg;
   b. a filler;
   c. a disintegrant;
   d. a surfactant which is sodium lauryl sulfate and is present in an amount of 0.3 wt % to 2 wt % by weight of the tablet;
   e. a lubricant; and
   f. a binder.

3. A tablet for oral administration comprising:
   a. 3-(6-(1-(2,2-difluorobenzo[d][1,3]dioxol-5-yl)cyclopropanecarboxamido)-3-methylpyridin-2-yl)benzoic acid (Compound 1) Form I wherein the Compound 1 Form I is present in an amount ranging from 25 mg to 250 mg;
   b. a filler;
   c. a disintegrant;
   d. a surfactant;
   e. a lubricant; and
   f. a binder;
   wherein Compound 1 Form I is present in an amount of 30 wt % to 70 wt % by weight of the tablet.

4. The tablet of claim 1, wherein the disintegrant is selected from agar-agar, algins, calcium carbonate, carboxymethylcellulose, cellulose, hydroxypropylcellulose, low substituted hydroxypropylcellulose, clays, croscarmellose sodium, crospovidone, gums, magnesium aluminum silicate, methylcellulose, polacrilin potassium, sodium alginate, sodium starch glycolate, maize starch, potato starch, tapioca starch, and any combination thereof.

5. The tablet of claim 1, wherein the surfactant is selected from sodium lauryl sulfate, sodium stearyl fumarate, polyoxyethylene 20 sorbitan mono-oleate, and any combination thereof.

6. The tablet of claim 1, wherein the tablet comprises an additional therapeutic agent, which is a cystic fibrosis transmembrane conductance regulator potentiator.

7. The tablet of claim 6, wherein the additional therapeutic agent is N-(5-hydroxy-2,4-di-tert-butylphenyl)-4-oxo-1H-quinoline-3-carboxamide.

8. The tablet of claim 1, wherein Compound 1 Form I is present in an amount of 30 wt % to 70 wt % by weight of the tablet.

9. The tablet of claim 8, wherein Compound 1 Form I is present in the tablet in an amount of 30 wt % to 60 wt % by weight of the tablet.

10. The tablet of claim 1, wherein the Compound 1 Form I is present in the tablet in an amount of 200 mg.

11. The tablet of claim 1, wherein the Compound 1 Form I is present in the tablet in an amount of 100 mg.

12. The tablet of claim 1, wherein the filler is selected from cellulose, modified cellulose, sodium carboxymethyl cellulose, ethyl cellulose hydroxymethyl cellulose, hydroxypropylcellulose, cellulose acetate, microcrystalline cellulose, dibasic calcium phosphate, sucrose, lactose, corn starch, potato starch, and any combination thereof.

13. The tablet of claim 12, wherein the filler is microcrystalline cellulose (MCC) and is present in the tablet in an amount ranging from 20 wt % to 55 wt % by weight of the tablet.

14. The tablet of claim 1, wherein the polyvinylpyrrolidone is present at a concentration of 1 wt % to 8 wt % by weight of the tablet.

15. The tablet of claim 1, wherein the lubricant is selected from magnesium stearate, calcium stearate, zinc stearate, sodium stearate, stearic acid, aluminum stearate, leucine, glyceryl behenate, hydrogenated vegetable oil, and any combination thereof.

16. The tablet of claim 15, wherein the lubricant is magnesium stearate and is present at a concentration of 0.15 wt % to 4.5 wt % by weight of the tablet.

17. The tablet of claim 1,
wherein the surfactant is sodium lauryl sulfate and is present in an amount of 0.3 wt % to 2 wt % by weight of the tablet.

18. The tablet of claim 1,
wherein the disintegrant is croscarmellose sodium and is present in the tablet at a concentration of about 6 wt % to about 10 wt % by weight of the tablet; and
wherein the surfactant is sodium lauryl sulfate and is present in an amount of 0.3 wt % to 2 wt % by weight of the tablet.

19. The tablet of claim 1,
wherein the disintegrant is croscarmellose sodium and is present in the tablet at a concentration of about 6 wt % to about 10 wt % by weight of the tablet.

20. The tablet of claim 1,
wherein the filler is microcrystalline cellulose (MCC) and is present in the tablet in an amount of 25 wt % to 50 wt % by weight of the tablet;
wherein the disintegrant is croscarmellose sodium and is present in the tablet at a concentration of about 6 wt % to about 10 wt % by weight of the tablet;
wherein the surfactant is sodium lauryl sulfate at a concentration of 0.3 wt % to 2 wt % by weight of the tablet;
wherein the lubricant is magnesium stearate at a concentration of 0.15 wt % to 4.5 wt % by weight of the tablet; and
wherein the polyvinylpyrrolidone is present at a concentration of 2 wt % to 5 wt % by weight of the tablet.

21. The tablet of claim 1,
wherein the filler is microcrystalline cellulose (MCC) and is present in the tablet in an amount of 25 wt % by weight of the tablet;
wherein the disintegrant is croscarmellose sodium and is present in the tablet at a concentration of about 6 wt % by weight of the tablet;
wherein the surfactant is sodium lauryl sulfate at a concentration of 0.8 wt % by weight of the tablet;
wherein the lubricant is magnesium stearate at a concentration of 1 wt % by weight of the tablet; and
wherein the polyvinylpyrrolidone is present at a concentration of 3 wt % by weight of the tablet.

22. A method of treating or lessening the severity of cystic fibrosis in a subject, comprising administering to the subject a tablet of claim 1.

* * * * *